US010378005B2

(12) United States Patent
Schmidt et al.

(10) Patent No.: US 10,378,005 B2
(45) Date of Patent: Aug. 13, 2019

(54) RECOMBINANT FACTOR H AND VARIANTS AND CONJUGATES THEREOF

(71) Applicant: University Court of The University of Edinburgh, Edinburgh (GB)

(72) Inventors: Christoph Schmidt, Edinburgh (GB); Paul N. Barlow, Edinburgh (GB); Anna Richards, Edinburgh (GB)

(73) Assignee: UNIVERSITY COURT OF THE UNIVERSITY OF EDINBURGH, Edinburgh (GB)

( * ) Notice: Subject to any disclaimer, the term of this patent is extended or adjusted under 35 U.S.C. 154(b) by 0 days.

(21) Appl. No.: 15/483,814

(22) Filed: Apr. 10, 2017

(65) Prior Publication Data

US 2017/0335310 A1 Nov. 23, 2017

Related U.S. Application Data

(63) Continuation of application No. 14/541,834, filed on Nov. 14, 2014, now abandoned, which is a continuation of application No. 13/518,614, filed as application No. PCT/GB2010/002334 on Dec. 23, 2010, now Pat. No. 8,889,374.

(30) Foreign Application Priority Data

Dec. 24, 2009 (GB) .................................. 0922659.8

(51) Int. Cl.

| | |
|---|---|
| ***C07H 21/04*** | (2006.01) |
| ***C07K 14/47*** | (2006.01) |
| ***C12N 9/88*** | (2006.01) |
| *C12P 21/06* | (2006.01) |
| *C07H 21/02* | (2006.01) |
| *C12P 1/02* | (2006.01) |
| *C12P 1/04* | (2006.01) |
| *C12N 1/00* | (2006.01) |
| *C12N 5/04* | (2006.01) |
| *C12N 5/10* | (2006.01) |
| *C12N 15/00* | (2006.01) |

(52) U.S. Cl.

CPC .............. *C12N 9/88* (2013.01); *C07K 14/472* (2013.01); *C07K 14/4702* (2013.01); *C12Y 402/01002* (2013.01)

(58) Field of Classification Search

None

See application file for complete search history.

(56) References Cited

U.S. PATENT DOCUMENTS

| | | | |
|---|---|---|---|
| 7,745,389 | B2 | 6/2010 | Hageman et al. |
| 8,497,350 | B2 | 7/2013 | Hageman et al. |
| 8,889,374 | B2 | 11/2014 | Schmidt et al. |
| 9,540,626 | B2 | 1/2017 | Lambris et al. |
| 2007/0020647 | A1 | 1/2007 | Hageman et al. |
| 2008/0221011 | A1 | 9/2008 | Gilkeson et al. |
| 2013/0011857 | A1 | 1/2013 | Binder et al. |
| 2013/0296255 | A1 | 11/2013 | Hageman et al. |

FOREIGN PATENT DOCUMENTS

| | | |
|---|---|---|
| EP | 1336618 | 8/2003 |
| WO | WO20030040310 | 5/2003 |
| WO | WO-2007038995 A1 | 4/2007 |
| WO | WO-2008135237 A1 | 11/2008 |
| WO | WO20080135237 | 11/2008 |
| WO | WO20080139496 | 11/2008 |

OTHER PUBLICATIONS

"D'Anjou, Marc C., et al.," "A Rational Approach to Improving Productivity in Recombinant Pichia Pastoris Fermentation," Biotechnology and Bioengineering, vol. 72, No. 1. pp. 1-11 (2001).

Ferreira, et al., "Complement control protein factor H: the good, the bad and the inadequate," Mol. Immunol., 47(13) pp. 2187-2197 (2010).

Hebecker, et al., "An Engineered Construct Combining Complement Regulatory and Surface-Recognition Domains Represents a Minimal-Size Functional Factor H," Journal of Immunology 191, pp. 912-921 (2013).

Herbert et al., "Structural and functional studies of C-terminal domains of complement factor H," Molecular Immunology, 41, pp. 243-244 (2004).

Kavenagh et al., "The decay accelerating factor mutation I197V found in hemolytic uraemic syndrome does not impair complement regulation,", Molecular Immunology, 44, pp. 3162-3167 (2007).

Lau et al., "Dense deposit disease and the factor H H402 allele," Clinical and Experimental Nephrology, 12, pp. 228- 232 (2008).

Lorimer, et al., "Gene Composer: Database Software for Protein Construct Design, Codon Engineering, and Gene Synthesis," BMC Biotechnology, vol. 9, No. 36, pp. 1-22 (2009).

Ormsby, R. J., et al., "Expression of Human Factor H in the Methyltrophic Yeast *Pichia pastoris*," Abstract, Molecular Immunology, vol. 35, No. 6-7, pp. 353 (1988).

PCT International Search Report/Written Opinion prepared for PCT/GB2010/002334, dated Jun. 6, 2011.

Rabhi-Essafi, et al., "Codon Optimization to Improve the Production Yield of Recombinant Human Interferon α Alpha by Pichia Pastoris," 2007, Abstract, Journal of Biotechnology, vol. 131, No. 2, pp. S7 (2007).

Schmidt et al., "A New Map of Glycosaminoglycan and C3b Binding Sites on Factor H," The Journal of Immunology, 181, 2610-2619 (2008).

Schmidt, et al., "Production of Biologically Active Complement Factor H in Therapeutically Useful Quantities," Protein Expression and Purification, No. 76, pp. 254-263 (2011).

(Continued)

*Primary Examiner* — Nancy J Leith

(74) *Attorney, Agent, or Firm* — White & Case LLP

(57) ABSTRACT

The present invention relates to recombinant factor H and variants and conjugates thereof and methods of their production, as well as uses and methods of treatment involving the materials.

3 Claims, 16 Drawing Sheets

Specification includes a Sequence Listing.

(56) References Cited

OTHER PUBLICATIONS

Schmidt, et al., "Rational Engineering of a Minimized Immune Inhibitor with Unique Triple-Targeting Properties," The Journal of Immunology, 190, pp. 5712-5721 (2013).
Sharma et al., "Identification of three physically and functionally distinct binding sites for C3b in human complement factor H by deletion mutagenesis," 93 Proceedings of the National Academy of Sciences USA, pp. 10996-11001 (1996).
Sinclair, et al., "Synonymous Codon Usage Bias and the Expression of Human Glucocerebrosidase in the Methylotrophic Yeast, *Pichia pastoris*," Protein Expression and Purification, Academic Press, vol. 26, pp. 96-105 (2002).
Tedeschi-Blok et al., "Population-Based Study of Early Age-Related Macular Degeneration," Ophthalmology, 114(1), pp. 99-103 (2007).
Tsai, et al., "Overproduction of Pichia Pastoris or Plasmodium Falciparum Protein Disulfide Isomerase Affects Expression, Folding and 0-Linked Glycosylation of a Malaria Vaccine Candidate Expressed in P. Pastoris," Journal of Biotechnology, vol. 121. pp. 458-470 (2006).
Schutter, et al., "Genome Sequence of the Recombinant Protein Production Host Pichia Pastoris", Nature Biotechnology, 27, 6, pp. 561-566, 2009.
Yadava, et al, "Effect of Codon Optimization on Expression Levels of a Functionally Folded Malaria Vaccine Candidate in Prokaryotic and Eukaryotic Expression Systems", Infection and Immunity, vol. 71, No. 9, pp. 4961-4969, Sep. 2003.
Li, P., et al., "Expression of Recombinant Proteins in Pichia Pastoris", Appl. Biochem Biotechnol, Aug. 2007: 142(2); 105-24.
Noguchi, S., et al., "Purification of human beta2-adrenergic receptor expressed in methylotrophic yeast Pichia pastoris",. J. Biochem, Dec. 2006; 140(6): 799-804.
Ormsby, R. J., et al., "Expression of Human Factor H in the Methyltrophic Yeast Pichia Pastoris," Abstract, Molecular Immunology, vol. 35, No. 6-7, pp. 353 (1998).
Ripoche, J., et al, "The complete amino acid sequence of human complement factor H", Biochem Journal, vol. 249, 1988, pp. 593-602.
Wang, H., et al, "Protein expression and purification of human Zbtb7A in Pichia pastoris via gene codon optimization and synthesis", Protein Expr Purif, Aug. 2008;60(2): 97-102.

Figure 1A: SEQ ID NOS: 1 (Wild-type) and 2 (Codon-opt)

```
Wild-type       GGAGATTGCAATGAACTTCCTCCAAGAAGAAATACAGAAATTCTGACAGGTTCCTGGTCT 60
Codon-opt       GAGGATTGTAACGAGTTGCCACCAAGAAGAAACACTGAGATCTTGACTGGTTCTTGGAGT 60
                *  ***** ** **  * ** *********** ** ** **  **** ***** ***  *

Wild-type       GACCAAACATATCCAGAAGGCACCCAGGCTATCTATAAATGCCGCCCTGGATATAGATCT 120
Codon-opt       GATCAAACTTACCCAGAGGGTACTCAGGCTATCTACAAGTGTAGACCAGGTTACAGATCC 120
                ** ***** ** ***** ** ** *********** ** **  * ** ** ** *****

Wild-type       CTTGGAAATGTAATAATGGTATGCAGGAAGGGAGAATGGGTTGCTCTTAATCCATTAAGG 180
Codon-opt       TTGGGTAACGTTATCATGGTTTGTAGAAAGGGTGAGTGGGTTGCATTGAACCCATTGAGA 180
                 * ** ** ** ** ***** ** ** ***** ** ********  * ** ***** **

Wild-type       AAATGTCAGAAAAGGCCCTGTGGACATCCTGGAGATACTCCTTTTGGTACTTTTACCCTT 240
Codon-opt       AAGTGTCAGAAAAGACCATGTGGTCACCCAGGTGATACTCCATTCGGTACTTTCACTTTG 240
                ** *********** ** ***** ** ** ** ******** ** ******** **  *

Wild-type       ACAGGAGGAAATGTGTTTGAATATGGTGTAAAAGCTGTGTATACATGTAATGAGGGGTAT 300
Codon-opt       ACTGGTGGTAACGTTTTCGAGTACGGTGTTAAGGCTGTTTACACTTGTAACGAGGGTTAC 300
                ** ** ** ** ** ** ** ** ***** ** ***** ** ** ***** ***** **

Wild-type       CAATTGCTAGGTGAGATTAATTACCGTGAATGTGACACAGATGGATGGACCAATGATATT 360
Codon-opt       CAGTTGTTGGGAGAGATCAACTACAGAGAGTGTGATACTGACGGATGGACTAACGACATT 360
                ** *** * ** ***** ** *** * ** ***** ** ** ******** ** ** ***

Wild-type       CCTATATGTGAAGTTGTGAAGTGTTTACCAGTGACAGCACCAGAGAATGGAAAAATTGTC 420
Codon-opt       CCAATCTGTGAAGTTGTTAAGTGTTTGCCAGTTACTGCTCCAGAGAACGGAAAGATTGTT 420
                ** ** *********** ******** ***** ** ** ******** ***** *****

Wild-type       AGTAGTGCAATGGAACCAGATCGGGAATACCATTTTGGACAAGCAGTACGGTTTGTATGT 480
Codon-opt       TCCTCCGCTATGGAACCAGATAGAGAGTACCACTTCGGACAGGCTGTTAGATTCGTTTGT 480
                      ** ************ * ** ***** ** ***** ** **  * ** ** ***

Wild-type       AACTCAGGCTACAAGATTGAAGGAGATGAAGAAATGCATTGTTCAGACGATGGTTTTTGG 540
Codon-opt       AACTCCGGTTACAAGATTGAAGGTGACGAAGAGATGCACTGTTCTGATGACGGTTTCTGG 540
                ***** ** ************** ** ***** ***** ***** ** ** ***** ***

Wild-type       AGTAAAGAGAAACCAAAGTGTGTGGAAATTTCATGCAAATCCCCAGATGTTATAAATGGA 600
Codon-opt       TCCAAAGAAAAGCCAAAGTGTGTTGAGATCTCCTGTAAGTCCCCAGACGTTATTAACGGT 600
                   ***** ** *********** ** ** ** ** ** ******** ***** ** **

Wild-type       TCTCCTATATCTCAGAAGATTATTTATAAGGAGAATGAACGATTTCAATATAAATGTAAC 660
Codon-opt       TCCCCAATCTCCCAAAAGATCATCTACAAAGAGAACGAGAGATTCCAGTACAAGTGTAAC 660
                ** ** ** ** ** ***** ** ** ** ***** **  **** ** ** ** ******

Wild-type       ATGGGTTATGAATACAGTGAAAGAGGAGATGCTGTATGCACTGAATCTGGATGGCGTCCG 720
Codon-opt       ATGGGTTACGAGTACTCTGAAAGAGGTGACGCTGTTTGTACTGAATCTGGATGGAGACCA 720
                ******** ** ***  ********* ** ***** ** *************** * **

Wild-type       TTGCCTTCATGTGAAGAAAAATCATGTGATAATCCTTATATTCCAAATGGTGACTACTCA 780
Codon-opt       TTGCCATCCTGTGAAGAGAAGTCCTGTGACAACCCATACATTCCAAACGGTGACTACTCC 780
                ***** ** ******** ** ** ***** ** ** ** ******** ***********
```

Figure 1B

```
Wild-type     CCTTTAAGGATTAAACACAGAACTGGAGATGAAATCACGTACCAGTGTAGAAATGGTTTT 840
Codon-opt     CCATTGAGAATCAAGCACAGAACTGGTGACGAGATCACTTACCAGTGTAGAAATGGTTTC 840
              ** ** ** ** ** *********** ** ** ***** ********************

Wild-type     TATCCTGCAACCCGGGGAAATACAGCCAAATGCACAAGTACTGGCTGGATACCTGCTCCG 900
Codon-opt     TACCCAGCTACTAGAGGTAACACTGCTAAGTGTACTTCCACTGGATGGATTCCAGCTCCA 900
              ** ** ** **  * ** ** ** ** ** ** **    ***** ***** ** *****

Wild-type     AGATGTACCTTGAAACCTTGTGATTATCCAGACATTAAACATGGAGGTCTATATCATGAG 960
Codon-opt     AGATGTACTTTGAAGCCATGTGACTACCCAGATATCAAGCACGGTGGTTTGTACCACGAG 960
              ******** ***** ** ***** ** ***** ** ** ** ** *** * ** ** ***

Wild-type     AATATGCGTAGACCATACTTTCCAGTAGCTGTAGGAAAATATTACTCCTATTACTGTGAT 1020
Codon-opt     AACATGAGAAGGCCATACTTCCCAGTTGCTGTTGGAAAGTACTACTCCTACTACTGTGAC 1020
              ** *** * ** ******** ***** ***** ***** ** ******** ********

Wild-type     GAACACTTTGAGACTCCGTCAGGAAGTTACTGGGATCACATTCATTGCACACAAGATGGA 1080
Codon-opt     GAACACTTCGAAACTCCATCTGGTTCTTACTGGGACCACATCCACTGTACTCAAGATGGT 1080
              ******** ** ***** ** **   ********* ***** ** ** ** ********

Wild-type     TGGTCGCCAGCAGTACCATGCCTCAGAAAATGTTATTTTCCTTATTTGGAAAATGGATAT 1140
Codon-opt     TGGTCCCCAGCTGTTCCATGTTTGAGAAAATGTTACTTCCCATACTTGGAGAACGGTTAC 1140
              ***** ***** ** *****  * *********** ** ** ** ***** ** ** **

Wild-type     AATCAAAATTATGGAAGAAAGTTTGTACAGGGTAAATCTATAGACGTTGCCTGCCATCCT 1200
Codon-opt     AACCAGAACTACGGTAGAAAGTTCGTTCAGGGAAAGTCCATTGACGTTGCTTGTCATCCA 1200
              ** ** ** ** ** ******** ** ***** ** ** ** ******** ** *****

Wild-type     GGCTACGCTCTTCCAAAAGCGCAGACCACAGTTACATGTATGGAGAATGGCTGGTCTCCT 1260
Codon-opt     GGTTACGCTTTGCCAAAGGCTCAGACTACTGTTACTTGTATGGAAAACGGTTGGTCCCCT 1260
              ** ****** * ***** ** ***** ** ***** ******** ** ** ***** ***

Wild-type     ACTCCCAGATGCATCCGTGTCAAAACATGTTCCAAATCAAGTATAGATATTGAGAATGGG 1320
Codon-opt     ACTCCTAGATGTATCAGAGTTAAGACTTGTTCCAAGTCCTCCATCGACATTGAGAACGGT 1320
              ***** ***** *** * ** ** ** ******** **    ** ** ******** **

Wild-type     TTTATTTCTGAATCTCAGTATACATATGCCTTAAAAGAAAAAGCGAAATATCAATGCAAA 1380
Codon-opt     TTCATTTCCGAGTCCCAGTACACTTACGCTTTGAAAGAGAAGGCTAAGTACCAGTGTAAA 1380
              ** ***** ** ** ***** ** ** ** ** ***** ** ** ** ** ** ** ***

Wild-type     CTAGGATATGTAACAGCAGATGGTGAAACATCAGGATCAATTACATGTGGGAAAGATGGA 1440
Codon-opt     TTGGGATACGTTACTGCTGACGGTGAAACTTCCGGATCAATCACATGTGGAAAAGACGGA 1440
               * ***** ** ** ** ** ******** ** ******** ******** ***** ***

Wild-type     TGGTCAGCTCAACCCACGTGCATTAAATCTTGTGATATCCCAGTATTTATGAATGCCAGA 1500
Codon-opt     TGGAGTGCTCAACCAACTTGTATCAAGTCTTGTGACATCCCAGTTTTCATGAACGCTAGA 1500
              ***   ******** ** ** ** ** ******** ******** ** ***** ** ***

Wild-type     ACTAAAAATGACTTCACATGGTTTAAGCTGAATGACACATTGGACTATGAATGCCATGAT 1560
Codon-opt     ACTAAGAACGACTTCACATGGTTCAAGTTGAACGACACTTTGGACTACGAATGTCACGAC 1560
              ***** ** ************** *** **** ***** ******** ***** ** **
```

Figure 1C

```
Wild-type       GGTTATGAAAGCAATACTGGAAGCACCACTGGTTCCATAGTGTGTGGTTACAATGGTTGG 1620
Codon-opt       GGTTACGAATCTAACACTGGTTCCACTACTGGTTCCATCGTTTGTGGTTACAATGGATGG 1620
                ***** ***   ** *****   *** *********** ** ************** ***

Wild-type       TCTGATTTACCCATATGTTATGAAAGAGAATGCGAACTTCCTAAAATAGATGTACACTTA 1680
Codon-opt       AGTGACTTGCCAATCTGTTACGAGAGAGAGTGCGAGTTGCCAAAGATCGACGTTCATTTG 1680
                  *** ** ** ** ***** ** ***** *****  * ** ** ** ** ** ** **

Wild-type       GTTCCTGATCGCAAGAAAGACCAGTATAAAGTTGGAGAGGTGTTGAAATTCTCCTGCAAA 1740
Codon-opt       GTTCCAGACAGAAAGAAGGACCAGTACAAAGTTGGAGAGGTTTTGAAGTTCTCCTGTAAG 1740
                ***** **  * ***** ******** ************** ***** ******** **

Wild-type       CCAGGATTTACAATAGTTGGACCTAATTCCGTTCAGTGCTACCACTTTGGATTGTCTCCT 1800
Codon-opt       CCAGGTTTCACTATCGTTGGTCCAAACTCCGTTCAGTGTTACCACTTCGGTTTGTCTCCA 1800
                ***** ** ** ** ***** ** ** *********** ******** ** ********

Wild-type       GACCTCCCAATATGTAAAGAGCAAGTACAATCATGTGGTCCACCTCCTGAACTCCTCAAT 1860
Codon-opt       GACTTGCCTATCTGTAAAGAGCAGGTTCAATCCTGCGGACCACCACCAGAATTGTTGAAC 1860
                *** * ** ** *********** ** ***** ** ** ***** ** *** *  * **

Wild-type       GGGAATGTTAAGGAAAAAACGAAAGAAGAATATGGACACAGTGAAGTGGTGGAATATTAT 1920
Codon-opt       GGTAACGTTAAAGAAAAGACTAAAGAAGAGTACGGTCACTCCGAAGTTGTTGAGTACTAC 1920
                ** ** ***** ***** ** ******** ** ** ***   ***** ** ** ** **

Wild-type       TGCAATCCTGGATTTCTAATGAAGGGACCTAATAAAATTCAATGTGTTGATGGAGAGTGG 1980
Codon-opt       TGTAACCCAAGATTCTTGATGAAGGGTCCAAACAAGATCCAATGTGTTGACGGTGAGTGG 1980
                ** ** **  ****  * ******** ** ** ** ** *********** ** ******

Wild-type       ACAACTTTACCAGTGTGTATTGTGGAGGAGAGTACCTGTGGAGATATACCTGAACTTGAA 2040
Codon-opt       ACTACTTTGCCAGTTTGTATCGTTGAAGAGTCCACTTGTGGTGACATTCCAGAATTGGAA 2040
                ** ***** ***** ***** ** ** ***   ** ***** ** ** ** *** * ***

Wild-type       CATGGCTGGGCCCAGCTTTCTTCCCCTCCTTATTACTATGGAGATTCAGTGGAATTCAAT 2100
Codon-opt       CACGGATGGGCTCAATTGTCATCCCCACCATACTACTACGGTGACTCCGTTGAATTCAAC 2100
                ** ** ***** **  * ** ***** ** ** ***** ** ** ** ** ********

Wild-type       TGCTCAGAATCATTTACAATGATTGGACACAGATCAATTACGTGTATTCATGGAGTATGG 2160
Codon-opt       TGTTCCGAGTCCTTCACTATGATTGGTCACAGATCCATCACATGTATCCACGGTGTTTGG 2160
                ** ** ** ** ** ** ******** ******** ** ** ***** ** ** ** ***

Wild-type       ACCCAACTTCCCCAGTGTGTGGCAATAGATAAACTTAAGAAGTGCAAATCATCAAATTTA 2220
Codon-opt       ACTCAATTGCCACAGTGTGTTGCTATCGACAAGTTGAAGAAGTGTAAATCATCCAACCTT 2220
                ** *** * ** ******** ** ** ** **  * ******** ******** **  *

Wild-type       ATTATACTTGAGGAACATTTAAAAAACAAGAAGGAATTCGATCATAATTCTAACATAAGG 2280
Codon-opt       ATCATCTTGGAGGAACACTTGAAGAACAAGAAAGAGTTCGACCACAACTCCAACATCAGA 2280
                ** **  * ******** ** ** ******** ** ***** ** ** ** ***** **

Wild-type       TACAGATGTAGAGGAAAAGAAGGATGGATACACACAGTCTGCATAAATGGAAGATGGGAT 2340
Codon-opt       TACAGATGTAGAGGTAAAGAGGGATGGATCCACACTGTTTGTATCAACGGTAGATGGGAC 2340
                ************** ***** ******** ***** ** ** ** ** ** ********
```

Figure 1D

```
Wild-type     CCAGAAGTGAACTGCTCAATGGCACAAATACAATTATGCCCACCTCCACCTCAGATTCCC 2400
Codon-opt     CCTGAAGTTAACTGTTCCATGGCTCAGATTCAGTTGTGTCCACCACCACCACAAATTCCA 2400
              ** ***** ***** ** ***** ** ** ** ** ** ***** ***** ** *****

Wild-type     AATTCTCACAATATGACAACCACACTGAATTATCGGGATGGAGAAAAAGTATCTGTTCTT 2460
Codon-opt     AACTCCCACAACATGACTACTACTTTGAACTACAGAGATGGTGAAAAGGTTTCCGTTTTG 2460
              ** ** ***** ***** ** **  **** **  * ***** ***** ** ** *** *

Wild-type     TGCCAAGAAAATTATCTAATTCAGGAAGGAGAAGAAATTACATGCAAAGATGGAAGATGG 2520
Codon-opt     TGTCAAGAGAACTACTTGATCCAAGAGGGTGAAGAGATCACATGTAAGGACGGTAGATGG 2520
              ** ***** ** **  * ** ** ** ** ***** ** ***** ** ** ** ******

Wild-type     CAGTCAATACCACTCTGTGTTGAAAAAATTCCATGTTCACAACCACCTCAGATAGAACAC 2580
Codon-opt     CAGTCCATCCCTTTGTGTGTTGAGAAGATCCCATGTTCCCAACCACCTCAAATTGAGCAC 2580
              ***** ** **  * ******** ** ** ******** *********** ** ** ***

Wild-type     GGAACCATTAATTCATCCAGGTCTTCACAAGAAAGTTATGCACATGGGACTAAATTGAGT 2640
Codon-opt     GGTACTATCAACTCTTCCAGATCCTCTCAAGAGTCTTACGCTCACGGTACTAAGTTGTCC 2640
              ** ** ** ** ** ***** ** ** *****   *** ** ** ** ***** ***

Wild-type     TATACTTGTGAGGGTGGTTTCAGGATATCTGAAGAAAATGAAACAACATGCTACATGGGA 2700
Codon-opt     TACACTTGTGAGGGAGGTTTCAGAATCTCTGAGGAAAACGAGACTACTTGTTACATGGGA 2700
              ** *********** ******** ** ***** ***** ** ** ** ** *********

Wild-type     AAATGGAGTTCTCCACCTCAGTGTGAAGGCCTTCCTTGTAAATCTCCACCTGAGATTTCT 2760
Codon-opt     AAGTGGTCATCTCCACCACAATGTGAAGGATTGCCTTGTAAGTCTCCACCAGAGATTTCT 2760
              ** ***   ******** ** ********  * ******** ******** *********

Wild-type     CATGGTGTTGTAGCTCACATGTCAGACAGTTATCAGTATGGAGAAGAAGTTACGTACAAA 2820
Codon-opt     CACGGTGTTGTTGCTCACATGTCCGACTCTTACCAATACGGAGAAGAGGTTACCTACAAG 2820
              ** ******** *********** ***  *** ** ** ******** ***** *****

Wild-type     TGTTTTGAAGGTTTTGGAATTGATGGGCCTGCAATTGCAAAATGCTTAGGAGAAAAATGG 2880
Codon-opt     TGTTTCGAGGGTTTCGGTATTGATGGTCCAGCTATCGCTAAGTGTTTGGGAGAAAAGTGG 2880
              ***** ** ***** ** ******** ** ** ** ** ** ** ** ******** ***

Wild-type     TCTCACCCTCCATCATGCATAAAAACAGATTGTCTCAGTTTACCTAGCTTTGAAAATGCC 2940
Codon-opt     TCCCATCCTCCATCCTGTATCAAGACTGATTGTTTGTCCTTGCCATCCTTCGAAAACGCT 2940
              ** ** ******** ** ** ** ** ****** *    ** **   *** ***** **

Wild-type     ATACCCATGGGAGAGAAGAAGGATGTGTATAAGGCGGGTGAGCAAGTGACTTACACTTGT 3000
Codon-opt     ATCCCAATGGGAGAAAAGAAGGACGTTTACAAGGCTGGTGAACAAGTTACTTATACTTGT 3000
              ** ** ******** ******** ** ** ***** ***** ***** ***** ******

Wild-type     GCAACATATTACAAAATGGATGGAGCCAGTAATGTAACATGCATTAATAGCAGATGGACA 3060
Codon-opt     GCTACTTACTACAAGATGGACGGTGCTTCCAACGTTACTTGTATCAACTCCAGATGGACT 3060
              ** ** ** ***** ***** ** **    ** ** ** ** ** **   *********

Wild-type     GGAAGGCCAACATGCAGAGACACCTCCTGTGTGAATCCGCCCACAGTACAAAATGCTTAT 3120
Codon-opt     GGTAGACCAACTTGTAGAGACACTTCCTGTGTTAACCCACCAACTGTTCAGAACGCTTAC 3120
              ** ** ***** ** ******** ******** ** ** ** ** ** ** ** *****
```

Figure 1E

```
Wild-type     ATAGTGTCGAGACAGATGAGTAAATATCCATCTGGTGAGAGAGTACGTTATCAATGTAGG 3180
Codon-opt     ATCGTTTCCAGACAGATGTCTAAGTACCCATCCGGAGAACGTGTTAGATACCAATGTAGA 3180
              ** ** ** *********  *** ** ***** ** **  * **  * ** ********

Wild-type     AGCCCTTATGAAATGTTTGGGGATGAAGAAGTGATGTGTTTAAATGGAAACTGGACGGAA 3240
Codon-opt     TCCCCATACGAGATGTTCGGTGACGAAGAGGTTATGTGTTTGAACGGTAATTGGACTGAA 3240
                *** ** ** ***** ** ** ***** ** ******** ** ** ** ***** ***

Wild-type     CCACCTCAATGCAAAGATTCTACAGGAAAATGTGGGCCCCCTCCACCTATTGACAATGGG 3300
Codon-opt     CCACCACAGTGTAAGGACTCCACTGGTAAGTGTGGTCCACCTCCACCAATTGACAACGGT 3300
              ***** ** ** ** ** ** ** ** ** ***** ** ******** ******** **

Wild-type     GACATTACTTCATTCCCGTTGTCAGTATATGCTCCAGCTTCATCAGTTGAGTACCAATGC 3360
Codon-opt     GACATCACTTCTTTCCCTTTGTCCGTTTACGCTCCAGCTTCTTCCGTTGAGTACCAGTGT 3360
              ***** ***** ***** ***** ** ** *********** ** *********** **

Wild-type     CAGAACTTGTATCAACTTGAGGGTAACAAGCGAATAACATGTAGAAATGGACAATGGTCA 3420
Codon-opt     CAGAACTTGTACCAGTTGGAGGGTAACAAGAGAATCACTTGTAGAAACGGACAATGGAGT 3420
              *********** **  * ************ **** ** ******** *********

Wild-type     GAACCACCAAAATGCTTACATCCGTGTGTAATATCCCGAGAAATTATGGAAAATTATAAC 3480
Codon-opt     GAGCCACCAAAGTGTTTGCACCCATGTGTTATCTCCAGAGAAATCATGGAAAACTACAAC 3480
              ** ******** ** ** ** ** ***** ** *** ******* ******** ** ***

Wild-type     ATAGCATTAAGGTGGACAGCCAAACAGAAGCTTTATTCGAGAACAGGTGAATCAGTTGAA 3540
Codon-opt     ATTGCTTTGAGATGGACTGCTAAACAGAAGTTGTACTCCAGAACTGGTGAATCCGTTGAG 3540
              ** ** ** ** ***** ** ********* * ** ** ***** ******** *****

Wild-type     TTTGTGTGTAAACGGGGATATCGTCTTTCATCACGTTCTCACACATTGCGAACAACATGT 3600
Codon-opt     TTCGTTTGTAAGAGAGGTTACAGATTGTCCTCCAGATCCCACACTTTGAGAACTACATGT 3600
              ** ** *****  * ** **  *  * ** **  * ** ***** *** **** ******

Wild-type     TGGGATGGGAAACTGGAGTATCCAACTTGTGCAAAAAGATAG--- 3642
Codon-opt     TGGGACGGAAAATTGGAGTACCCAACTTGTGCTAAGAGATAGTAG 3645
              ***** ** *** ******* *********** ** ******
```

Figure 2: Trial for expression of recombinant human fH using DNA that was not optimised for codon usage

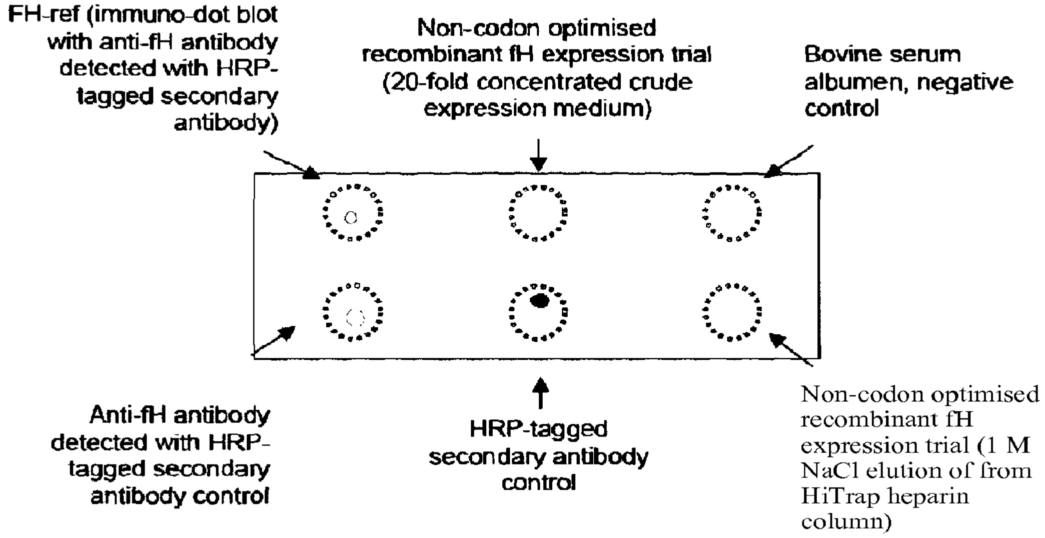

Legend to Figure 2: An attempted expression of recombinant fH in a three-litre fermentor trial was monitored using a standard immuno-blotting technique with a commercial polyclonal anti-fH antibody and secondary antibody coupled to horse radish peroxidase. A portion of the supernatant (after spinning out cells) was concentrated 20-fold while the remainder was diluted (to reduce salt concentration) and loaded onto a HiTrap (GE Healthcare) heparin column at 20 mM potassium phosphate, pH 6, and step eluted with 1 M NaCl in the same buffer. FH-ref is a reference sample of purchased from Comptech (Texas, USA).

*Schematic of human factor H (fH) showing SNPs and N-glycans*

*Set of vectors designed for production of human and mouse fH variants*

Figure 5A (part one of two): SEQ ID NOS:

| 3 | 4 | 5 | 6 | 7 | 8 | 13 | |
|---|---|---|---|---|---|---|---|
| Human: construct no. 1 | 2 | 3 | 4 | 5 | 6 | 11 | * |
| GGCGCG**CCGGATCCAAAAATGAGATTGTTGGCTAAGATCATCTGTTTGATGTTGTGGGCT** | | | a | b | | | |
| **ATCTGTGTTGCT**GAGGACTGTAACGAATTGCCACCGCGGAGAAACACTGAGATTTTGACT | | | | | | | |
| GGTTCCTGGTCCGATCAAACTTACCCAGAGGGTACTCAGGCTATCTAC**A**AGTGTAGACCA | | | | | | | |
| GGTTACAGATCCTTGGGTAAC**ATC**ATCATGGTTTGTAGAAAGGGTGAGTGGGTTGCTTTG | | | | **GTT** | **ATT** | | I-V |
| AACCCATTGAGAAAGTGTCAGAAAAGACCATGTGGTCACCCAGGTGATACTCCATTCGGT | | | | | | | |
| ACTTTCACTTTGACTGGTGGTAACGTTTTCGAGTACGGTGTTAAGGCTGTTTACACTTGT | | | | | | | |
| AACGAGGGTTACCAGTTGTTGGGTGAGATCAACTACAGAGAGTGTGATACTGACGGTTGG | | | | | | | |
| ACTAACGACATTCCAATCTGTGAGGTTGTTAAGTGTTTGCCAGTTACTGCTCCAGAGAAC | | | | | | | |
| GGTAAGATTGTTTCCTCCGCTATGGAACCAGATAGAGAGTACCACTTCGGTCAGGCTGTT | | | | | | | |
| AGATTCGTTTGTAACTCCGGTTACAAGATTGAAGGTGACGAAGAGATGCACTGTTCTGAT | | | | | | | |
| GACGGTTTCTGGTCCAAAGAAAAGCCAAAGTGTGTTGAGATTTCCTGTAAGTCCCCAGAC | | | | | | | |
| GTTATTAACGGTTCCCCAATCTCCCAAAAGATCATCTACAAAGAGAACGAGAGATTCCAG | | | | | | | |
| TACAAGTGTAACATGGGTTACGAGTACTCTGAAAGAGGTGACGCTGTTTGTACTGAATCT | | | | | | | |
| GGTTGGAGACCATTGCCATCCTGTGAAGAGAAGTCCTGTGACAACCCATACATTCCAAAC | | | | | | | |
| GGTGACTACTCCCCATTGAGAATCAAGCACAGAACTGGTGACGAGATCACTTACCAGTGT | | | | | | | |
| AG**A**AACGGTTTCTACCCAGCTACTAGAGGTAACACTGCTAAGTGTACTTCCACTGGTTGG | | | | | | | |
| ATTCCAGCTCCAAGATGTACTTTGAAGCCATGTGACTACCCAGATATCAAGCACGGTGGT | | | | | | | |
| TTGTACCACGAGAACATGAGAAGACCATACTTCCCAGTTGCTGTTGGAAAGTACTACTCC | | | | | | | |
| TACTACTGTGACGAACACTTCGAAACTCCATCTGGTTCTTACTGGGACCACATCCACTGT | | | | | | | |
| ACTCAAGATGGTTGGTCCCCAGCTGTTCCATGTTTGAGAAAATGTTACTTCCCATACTTG | | | | | | | |
| GAGAACGGTTACAACCAG**A**AC**TAC**GGTAGAAAGTTCGTTCAGGGAAAGTCCATTGACGTT | | | | **CAT** | | | Y-H |
| GCTTGTCATCCAGGTTACGCTTTGCCAAAGGCTCAGACTACTGTTACTTGTATGGAAAAC | | | | | | | |
| GGTTGGTCCCCTACTCCTAGATGTATCAGAGTTAAGACTTGTTCCAAGTCCTCCATCGAC | | | | | | | |
| ATTGAGAACGGTTTCATTTCCGAGTCCCAGTACACTTACGCTTTGAAAGAGAAGGCTAAG | | | | | | | |
| TACCAGTGTAAATTGGGATACGTTACTGCTGACGGTGAAACTTCCGGTTCCATCACTTGT | | | | | | | |
| GGTAAGGATGGTTGGTCTGCTCAACCAACTTGTATCAAGTCTTGTGACATCCCAGTTTTC | | | | | | | |
| ATGAACGCTAGAACTAAGAACGACTTCACATGGTTCAAGTTG**AAC**GACACTTTGGACTAC | **CAA** | **CAA** | | | | | N-Q |
| GAATGTCACGACGGTTACGAATCTAACACTGGTTCCACTACTGGTTCCATCGTTTGTGGT | | | | | | | |
| TACAACGGTTGGTCTGACTTGCCAATCTGTTACGAGAGAGAGTGCGAGTTGCCAAAGATC | | | | | c | | |
| GACGTTCATTTGGTTCCAGACAGAAAGAAGGACCAGTACAAGGTTGGTGAGGTTTTGAAG | | | | | | | |
| TTCTCCTGTAAGCCAGGTTTCACTATCGTTGGTCCAAACTCCGTTCAGTGTTACCATTTC | | | | | | | |
| GGTTTGTCCCCAGACTTGCCTATTTGTAAAGAGCAGGTTCAGTCTTGCGGTCCACCACCA | | | | | | | |
| GAATTGTTGAACGGTAACGTTAAAGAAAAGACTAAAGAAGAGTACGGTCACTCTGAGGTT | | | | | | | |
| GTTGAGTACTACTGTAACCCAAGATTCTTGATGAAGGGTCCAAACAAGATCCAATGTGTT | | | | | | | |
| GACGGTGAGTGGACTACTTTGCCAGTTTGTATCGTTGAAGAGTCCACTTGTGGTGACATT | | | | | | | |
| CCAGAATTGGAACACGGTTGGGCTCAATTGTCATCCCCACCATACTACTACGGTGACTCC | | | | | | | |
| GTTGAGTTC**AAC**TGTTCCGAGTCCTTCACTATGATTGGTCACAGATCCATCACATGTATC | **CAA** | **CAA** | **TAG** | | | | N-Q |
| CACGGTGTTTGGACTCAATTGCCACAGTGTGTTGCTATCGACAAGTTG**AAGAAG**TGT**AAA** | | | | | | **CAA** | K-Q |
| TCCTCCAACTTGATCATCTTGGAGGAACACTTGAAGAACAAG**AAA**GAGTTCGACCACAAC | | | | | | **CAA** | K-Q |
| TCCAACATC**AGA**TAC**AGA**TGT**AGA**GGT**AAA**GAGGGTTGGATTCACACTGTTTGTATCAAC | | | | | | **CAA** | X-Q |
| GGT**AGA**TGGGACCCTGAAGTT**AAC**TGTTCCATGGCTCAGATTCAGTTGTGTCCACCACCT | **CAA** | **CAA** | | | | **CAA** | d |
| CCACAAATTCCAAACTCCCAC**AAC**ATGACTACTACTTTGAACTACAGAGATGGTGAGAAG | **CAA** | **CAA** | | | | | N-Q |
| GTTTCCGTTTTGTGTCAAGAGAACTACTTGATCCAAGAGGGTGAGGAAATCACTTGTAAG | | | | | | | |
| GACGGTAGATGGCAATCCATCCCATTGTGTGTTGAGAAGATCCCATGTTCCCAACCACCA | | | | | | | |
| CAAATTGAGCACGGTACTATC**AACTCTTCC**AGATCCTCTCAAGAGTCTTACGCTCACGGT | **CAA** | CAA<br>*TCT*<br>*AGT* | | | | | e |
| ACTAAGTTGTCCTACACTTGTGAGGGTGGTTTCAG**A**ATCTCTGAGGAA**AAC**GAGACTACT | **CAA** | **TAG** | **TAG** | | | | N-Z |
| TGTTACATGGGAAAGTGGTCCTCTCCACCACAATGTGAAGGTTTGCCTTGTAAGTCTCCA | | | | | | | |
| CCAGAGATTTCTCACGGTGTTGTTGCTCACATGTCCGACTCTTACCAATACGGTGAAGAG | | | | | | | |
| GTTACTTACAAGTGTTTCGAGGGTTTCGGTATTGATGGTCCAGCTATCGCTAAGTGTTTG | | | | | | | |
| GGTGAAAAGTGGTCCCATCCTCCATCCTGTATCAAGACTGACTGTTTGTCCTTGCCATCT | | | | | | | |
| TTCGAGAACGCTATCCCAATGGGTGAAAAGAAGGACGTTTACAAGGCTGGTGAACAGGTT | | | | | | | |
| ACATACACTTGTGCTACTTACTACAAGATGGACGGTGCTTCC**AAC**GTTACTTGTATCAAC | **CAA** | **CAA** | | | | | N-Z |
| TCCAGATGGACTGGTAGACCAACTTGTAGAGACACTTCCTGTGTTAACCCACCAACTGTT | | | | | | | |
| CAGAACGCTTACATCGTTTCCAGACAGATGTCTAAGTACCCATCCGGTGAGAGAGTTAGA | | | | | | | |
| TACCAATGTAGATCCCCATACGAGATGTTCGGTGACGAAGAGGTTATGTGTTTGAACGGT | | | | | | | |
| **AAT**TGGACTGAACCACCACAGTGTAAGGACTCCACTGGTAAGTGTGGTCCACCTCCACCA | **CAA** | **CAA** | | | | | N-Z |
| ATTGACAACGGTGACATCACTTCTTTCCCATTGTCCGTTTACGCTCCAGCTTCTTCGGTT | | | | | | | |
| GAGTACCAGTGTCAGAACTTGTACCAGTTGGAGGGTAACAGAGAATCACTTGTAGAAAC | | | | | | | |
| GGACAATGGTCTGAGCCACCAAAGTGTTTGCACCCATGTGTTATCTCCAGAGAAATCATG | | | | | | | |
| GAAAACTACAACATTGCTTTGAGATGGACTGCTAAGCAGAAGTTGTACTCCAGAACAGGT | | | | | | | |
| GAGTCTGTTGAGTTTGTTTGTAAGAGAGGTTACAGATTGTCCTCCAGATCCCACACTTTG | | | | | | | |
| AGAACTACATGTTGGGACGGAAAGTTGGAGTACCCAACTTGTGCTAAGAGATAATGAGCG | | | | | | | |
| GCCGCTTAATTAA | | | | | | | |

* Resultant changes in amino acid residue sequence; Z = Q or amber codon; X = Lys or Arg

[a] Entire sequence in bold on these two lines is replaced with the following sequence: CCTGCAGGT

[b] Entire underlined sequence replaced with the following sequence: TTCCCATCCCATCTTCACTGCTGTTTTGTTCGCTGCTTCTTCTGCTTTGGCTGCTCCAGTTAACACTACTACTGAGGACGAGACTGCTCAAATTCCAGCTGAGGCTG TTATTGGTTACTCTGACTTGGAAGGTGATTTCGACGTTGCTGTTTTGCCATTCTCCAACTCCACTAACAACGGTTTGTTGTTCATCAACACTACTATCGCTTCCAT TGCTGCTAAAGAAGAGGGAGTTTCCCTCGAGAAGAGA

[c] entire underlined sequence (corresponding to CCPs 10-15) deleted

[d] *R-Q* or N-Q/amber

[e] N-Q in construct 2, or N S S - Q S S in construct 3

Figure 5B (Part two of two): SEQ ID NOS: 9 10 11 12

| Mouse: construct no. 7 | 8 | 9 | 10 | * |
|---|---|---|---|---|
| GGCGCGCCGGATCCAAAAATGAGATTGTCCGCTAGAATCATCTGGTTGATCTTGTGGACT<br>GTTTGTGCTGCTGAGGATTGTAAAGGTCCACCACCGCGGGAAAACTCCGAGATTTTGTCT | a | | | Alpha-factor, no EA |
| GGTTCTTGGTCCGAACAATTGTACCCAGAGGGTACTCAAGCTACTTACAAGTGTAGACCA | | | | |
| GGTTACAGAACTTTGGGTACTATCGTTAAGGTTTGTAAGAACGGAAAGTGGGTTGCTTCT | | | | |
| **AAC**CCATCCAGAATCTGTAGAAAGAAACCATGTGGTCACCCAGGTGATACTCCATTCGGT | **CAA** | **CAA** | CAA | N – Q |
| TCCTTCAGATTGGCTGTTGGTTCCCAATTCGACTTCGGTGCTAAGGTTGTTTACACTTGT | | | | |
| GACGACGGTTACCAATTGTTGGGTGAGATCGACTACAGAGAATGTGGTGCTGACGGTTGG | | | | |
| ATTAACGACATCCCATTGTGTGAGGTTGTTAAGTGTTTGCCAGTTACTGAGTTGGAGAAC | | | | |
| GGTAGAATTGTTTCTGGTGCTGCTGAAACTGACCAAGAGTACTACTTCGGACAGGTTGTT | | | | |
| AGATTCGAGTGTAACTCCGGTTTCAAGATCGAAGGTCACAAAGAGATTCACTGTTCCGAG | | | | |
| AACGGTTTGTGGTCTAACGAGAAGCCAAGATGTGTTGAGATTTTGTGTACTCCACCAAGA | | | | |
| GTTGAAAACGGTGACGGTATCAACGTTAAGCCAGTTTACAAAGAGAACGAGAGATACCAC | | | | |
| TACAAGTGTAACCACGGTTACGTTCCAAAAGAAAGAGGTCACCCTCTTTCTACTGGTTCT | | | | |
| GGTTGGTCCTCTCAACCATTCTGTGAAGAGAAGAGATGTTCCCCACCATACATCTTGAAC | | | | |
| GGTATCTACACTCCACACAGAATCATTCACAGATCCGACGACGAGATTAGATACGAATGT | | | | |
| AACTACGGATTCTACCCAGTTACTGGTTCCACTGTTTCCAAGTGTACTCCAACTGGTTGG | | | | |
| ATTCCAGTTCCAAGATGTACTTTGAAGCCATGTGAGTTCCCACAATTCAAGTACGGTAGA | | | | |
| TTGTACTACGAAGAGTCCTTGAGACCAAACTTCCCAGTTTCCATCGGTAACAAGTACTCC | | | | |
| TACAAGTGTGACAACGGTTTCTCTCCACCATCTGGTTACTCTTGGGACTACTTGAGATGT | | | | |
| ACTGCTCAAGGTTGGGAACCAGAGGTTCCATGTGTTAGAAAGTGTGTTTTCCACTACGTT | | | | |
| GAGAACGGTGATTCTGCTTACTGGGAGAAGGTTTACGTTCAAGGTCAGTCCTTGAAGGTT | | | | |
| CAGTGTTACAACGGTTACTCCTTGCAAAACGGTCAGGACACTATGACTTGTACTGAGAAC | | | | |
| GGTTGGTCACCACCACCAAAGTGTATCAGAATCAAGACTTGTTCCGCTTCCGACATTCAC | | | | |
| ATCGACAACGGATTCTTGTCTGAGTCCTCCTCCATTTACGCTTTGAACAGAGAGACTTCC | | | | |
| TACAGATGTAAGCAGGGATACGTTACAAACACTGGTGAGATTTCCGGTTCCATCACTTGT | | | | |
| TTGCAGAATGGTTGGTCCCCACAGCCATCTTGTATTAAGTCCTGTGACATGCCAGTTTTC | | | | |
| GAGAACTCCATCACTAAGAACACTAGAACATGGTTCAAGTTGAACGACAAGTTGGACTAC | | | | |
| GAGTGTTTGGTTGGTTTCGAGAACGAGTACAAGCACACTAAGGGTTCCATCACATGTACT | | | | |
| TACTACGGTTGGTCTGACACTCCATCCTGTTACGAAAGACAGTGTTCCGTTCCAACTTTG | | | | |
| GACAGAAAGTTGGTTGTTTCCCCAAGAAAAGAGAAGTACAGAGTTGGAGACTTGTTGGAG | | | | |
| TTCTCTTGTCACTCTGGTCATAGAGTTGGTCCAGACTCCGTTCAATGTTACCACTTTGGA | | | | |
| TGGTCCCCAGGTTTTCCAACTTGTAAGGGTCAGGTTGCTTCTTGTGCTCCACCATTGGAG | | | | |
| ATTTTGAACGGTGAGATCAACGGTGCTAAGAAGGTTGAATACTCCCACGGTGAAGTTGTT | | | | |
| AAGTACGACTGTAAGCCAAGATTCTTGTTGAAGGGTCCAAACAAGATCCAATGTGTTGAC | | | | |
| GGT**AAC**TGGACTACTTTGCCAGTTTGTATCGAGGAAGAAAGAACTTGCGGAGACATCCCA | **CAA** | CAA | CAA | N–Q |
| GAATTGGAACACGGTTCCGCTAAGTGTTCTGTTCCACCATACCACCATGGTGATTCCGTT | | | | |
| GAGTTCATCTGTGAG**GAAAAC**TTCACTATGATCGGTCACGGTTCCGTTTCTTGTATTTCC | CAA | *GAGTAG* | ***GAGTAG*** | *EN*–*EQ* or *E*Amb |
| GGTAAGTGGACTCAGTTGCCAAAGTGTGTTGCTACTGACCAGTTGGAGAAGTGTAGAGTT | | | | |
| TTGA**A**GTCCACTGGTATCGAGGCTATCAAGCCAAAGTTGACTGAGTTCACTCAC**AACTCC** | ***CAG*** | *CAG*TCT | CAG | *N*S–*Q*S |
| ACTATGGACTACAAATGTAGAGACAAGCAAGAGTACGAGAGATCCATCTGTATCAACGGT | | | | |
| AAATGGGACCCAGAACCA**AAC**TGTACTTCCAAGACTTCTTGTCCACCACCACCACAAATT | CAA | **CAA** | CAA | N–Q |
| CCAAAC**A**CTCAGGTTATCGAGACTACTGTTAAGTACTTGGACGGTGAGAAGTTGTCCGTT | | | | |
| TTGTGTCAGGACAACTACTTGACTCAAGACTCCGAAGAGATGGTTTGTAAGGACGGTAGA | | | | |
| TGGCAATCTTTGCCAAGATGTATCGAGAAGATCCCATGTTCTCAGCCACCAACTATTGAG | | | | |
| CACGGTTCCATTAACTTGCCAAGATCCTCCGAAGAAAGAAGAGACTCCATCGAATCCTCT | | | | |
| TCTCACGAACACGGTACTACTTTCTCTTACGTTTGTGATGACGGTTTCAGAATCCCAGAA | | | | |
| GAGAAC**A**GAATCACTTGTTACATGGGAAAGTGGTCCACTCCACCTAGATGTGTTGGTTTG | | | | |
| CCATGTGGTCCACCACCTTCTATTCCATTGGGTACTGTTTCTTTGGAGTTGGAGTCCTAC | | | | |
| CAACACGGTGAAGAGGTTACTTACCACTGTTCCACTGGTTTCGGTATTGATGGTCCAGCT | | | | |
| TTCATTATCTGTGAGGGTGGTAAGTGGTCTGATCCACCTAAGTGTATTAAGACTGACTGT | | | | |
| GACGTTTTGCCAACTGTTAAGAACGCTATCATCAGAGGTAAGTCCAAGAAGTCCTACAGA | | | | |
| ACTGGAGAGCAGGTTACTTTCAGATGTCAGTCCCCATACCAAATG**AAC**GGTTCCGACACT | CAA | CAA | TAG | N–Q or Amber |
| GTTACTTGTGTTAACTCCAGATGGATCGGTCAACCAGTTTGTAAGGATAACTCCTGTGTT | | | | |
| GATCCACCACATGTTCCA**AAC**GCTACTATCGTTACTAGAACTAAGAACAAGTACTTGCAT | **CAA** | **CAA** | CAA | N Q |
| GGTGACAGAGTTAGATATGAGTGTAACAAGCCATTGGAGTTGTTCGGTCAAGTTGAGGTT | | | | |
| ATGTGTGAGAACGGTATCTGGACTGAGAAGCCAAAGTGTAGAGACTCCACTGGTAAGTGT | | | | |
| GGTCCTCCACCACCAATTGACAACGGTGACATCACTTCTTTGTCCTTGCCAGTTTACGAA | | | | |
| CCTTTGTCCTCCGTTGAGTACCAATGTCAGAAGTACTACTTGTTGAAAGGTAAGAAAACT | | | | |
| ATCACTTGTACTAATGGTAAATGGTCCGAGCCACAACTTGTTTGCACGCTTGTGTTATC | | | | |
| CCAGAGAACATCATGGAATCCCACAACATCATCTTGAAGTGGAGACACACTGAGAAGATT | | | | |
| TACTCTCACTCCGGTGAGGACATTGAGTTCGGTTGTAAGTACGGTTACTACAAGGCTAGA | | | | |
| GACTCTCCACCATTCAGAACTAAGTGTATC**AAC**GGAACTATCAACTACCCAACTTGTGTT | CAA | CAA | CAA | N–Q |
| TAATGAGCGGCCGCTTAATTAA | | | | |

Constructs 8, 9 and 10 are identical to 7 except where indicated by bold, *italic* or underline in which case the replacement codon is indicated by a footnote or by letters in matching format (bold or italics).

* Resultant changes in amino acid residue sequence

[a] Entire underlined sequence replaced with the following sequence:

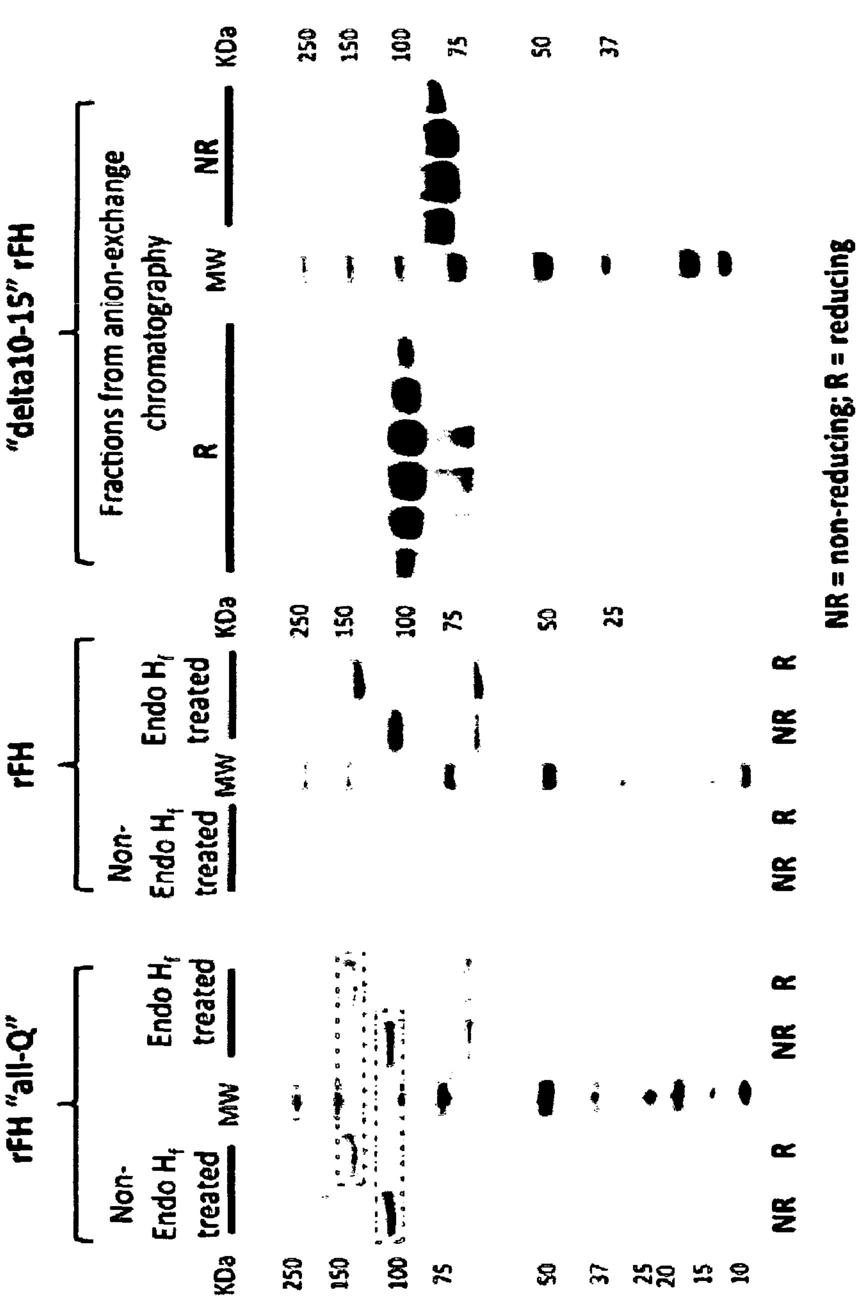
Figure 6: Polyacrylamide gel electrophoresis illustrating production of "all Q" and "delta10-15" mutants of rFH

Figure 7: A schematic summary of a route to therapeutic versions of FH
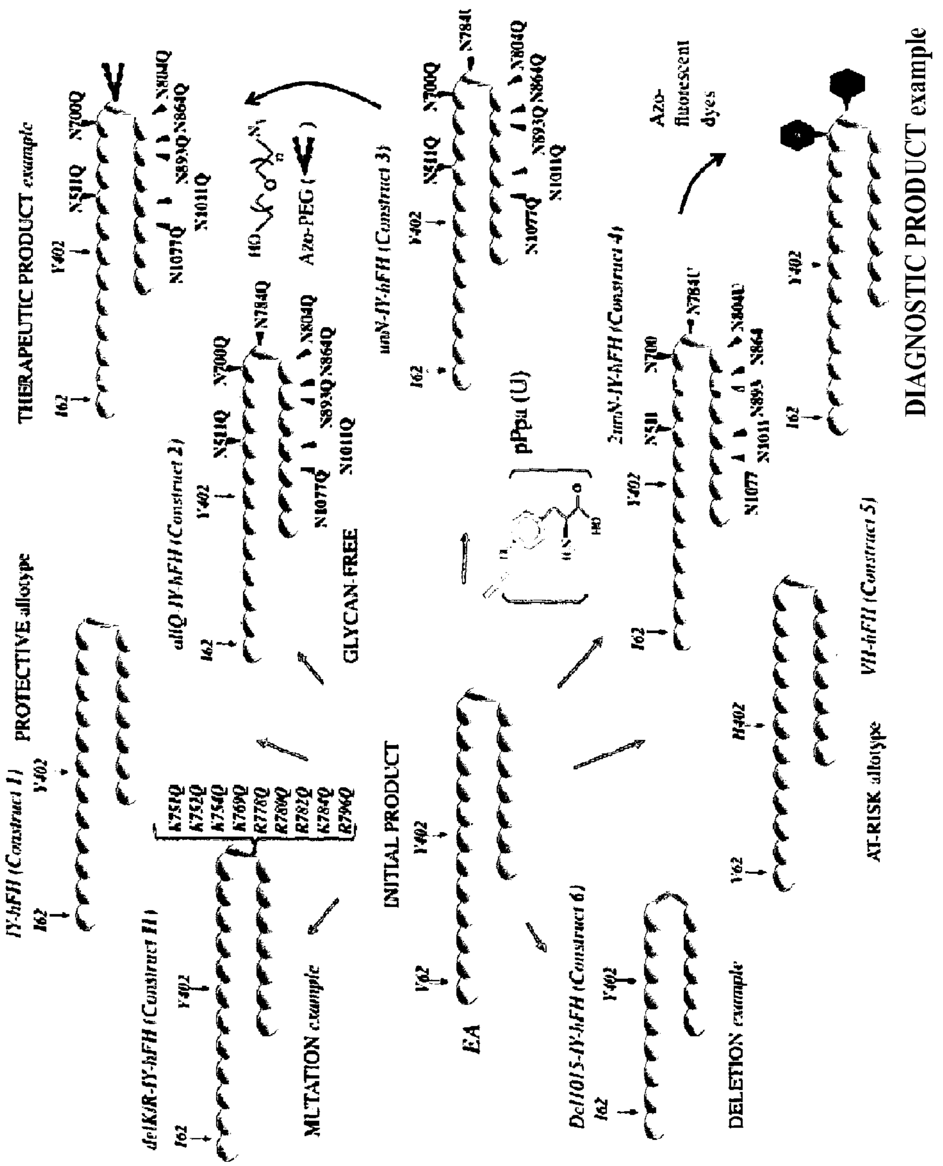

RECOMBINANT FACTOR H AND VARIANTS AND CONJUGATES THEREOF

CROSS-REFERENCE TO RELATED APPLICATIONS

This application is a continuation of U.S. patent application Ser. No. 14/541,834 (now abandoned), which was filed on Nov. 14, 2014 and is a continuation of U.S. patent application Ser. No. 13/518,614 (now U.S. Pat. No. 8,889,374), which entered the national stage on Sep. 28, 2012, and which is a United States National Stage filing under 35 U.S.C. § 371 of International Application No. PCT/GB2010/002334, filed Dec. 23, 2010, which claims the benefit of United Kingdom Patent Application No. 0922659.8, filed Dec. 24, 2009, the contents of all of which are incorporated by reference herein in their entirety. International Application No. PCT/GB2010/002334 was published under PCT Article 21(2) in English.

FIELD OF THE INVENTION

The present invention relates to recombinant factor H and variants and conjugates thereof and methods of their production, as well as uses and methods of treatment involving said materials.

BACKGROUND OF THE INVENTION

An increasing body of evidence suggests that the complement system regulatory glycoprotein, factor H (FH), if produced in sufficient quantities and endowed with appropriate pharmacokinetic and pharmacodynamic properties, would serve as a new biotherapeutic agent. This agent could prevent development of age-related macular degeneration (AMD) in genetically susceptible individuals and facilitate treatment in those with AMD and two life-threatening kidney conditions known as atypical haemolytic uraemic syndrome (aHUS) and dense deposit disease (DDD). More speculatively, this agent could have beneficial effects in the treatment or prevention of numerous other diseases in which inadequate complement regulation contributes to aetiology or symptoms.

However current attempts to produce FH through over-expression of a gene in recombinant cells have failed to yield the quantities that would be required for therapy, while purification from human plasma of sufficient quantities of the appropriate variants of FH has logistical and technical difficulties and carries health risks. There are urgent unmet clinical and commercial needs for multiple-gram quantities of biotherapeutic-grade recombinant versions of FH with minimal immunogenicity, an extended half-life and maximal efficacy.

Links between polymorphisms in FH and susceptibility to disease have been well documented and are reviewed, for example in: Opportunities for new therapies based on the natural regulators of complement activation. Brook E, Herbert A P, Jenkins H T, Soares D C, Barlow P N. *Ann N Y Acad Sci* 2005 1056:176-88; Complement factor H: using atomic resolution structure to illuminate disease mechanisms. Barlow P N, Hageman G S, Lea S M. *Adv Exp Med Biol.* 2008 632:117-42; Translational mini-review series on complement factor H: renal diseases associated with complement factor H: novel insights from humans and animals. Pickering M C, Cook H T. *Clin Exp Immunol* 2008 151:210-30; Translational mini-review series on complement factor H:

genetics and disease associations of human complement factor H. de Cordoba S R, de Jorge E G. *Clin Exp Immunol.* 2008 151:1-13.

Since these reviews were published numerous further published findings have broadened the scope of potential targets for FH-based therapies. Two recent examples establish an association between the FH gene (CFH) polymorphism (Y402H) and susceptibility to cardiovascular disease (CVD). Koeijvoets et al. (Complement factor H Y402H decreases cardiovascular disease risk in patients with familial hypercholesterolaemia. Koeijvoets K C, Mooijaart S P, Dallinga-Thie G M, Defesche J C, Steyerberg E W, Westendorp R G, Kastelein J J, van Hagen P M, Sijbrands E J. *Eur Heart J.* 2009 30:618-23. showed that amongst patients with severely increased risk of early-onset CVD due to hypercholestrolaemia, the Y402 CFH variant was inversely associated with susceptibility to CVD suggesting that CFH modifies the risk of CVD. In a study by Buraczynska et al. (Complement factor H gene polymorphism and risk of cardiovascular disease in end-stage renal disease patients. Buraczynska M, Ksiazek P, Zukowski P, Benedyk-Lorens E, Orlowska-Kowalik G. *Clin Immunol.* 2009; 132:285-90) of end-stage renal failure in patients on dialysis, multivariate logistic regression analysis showed that the Y402H genotype is independently associated with cardiovascular comorbidity; with homozygosity for the H402 allelebeing associated with an odds ratio of 7.28 (95% CI 5.32-9.95). In another recent development, Moreno-Navarrete et al. (Complement Factor H is expressed in adipose tissue in association with insulin resistance. Moreno-Navarrete J M, Martinez-Barricade R, Catalan V, Sabater M, Gomez-Ambrosi J, Ortega F J, Ricart W, Bliiher M, Frilhbeck G, de Cordoba S R, Fernandez-Real M J. *Diabetes* 2009: Epub October 15) showed that FH is expressed in adipose tissue in association with insulin resistance, suggesting a link between the alternative pathway of the complement system, obesity and metabolic disorders.

Data for the likely efficacy of FH in treatment is already very strong, and has precipitated numerous disclosures, patent applications and company start-ups. US2007/0020647 discusses the expression of human CFH in a variety of eukaryotic and prokaryotic protein-overproduction vectors and in mammalian cell lines, but only explicitly exemplifies expression in the human lung carcinoma cell line A549. The quantities of recombinant protein obtained from this cell line are not disclosed, but based on precedent and in the absence of any evidence to the contrary the amounts are expected to be inadequate for therapeutic purposes. WO2007/038995 describes the use of human factor H to treat aHUS. The patent application mentions the use of recombinant FH without providing significant details about the methods of production of recombinant FH, but is focused on purification of FH from human plasma.

Thus although the above two documents disclose the idea of using recombinant FH therapeutically, neither document actually teaches the large-scale production of recombinant FH that is absolutely essential for its therapeutic application; as shown herein, this is not a straightforward task.

Successful manufacture of larger amounts (greater than 10 mg) of pure recombinant full-length FH with preserved functional activities has not previously been reported in the scientific or patent literature. Indeed, in the limited data supporting the patents discussed above, the authors demonstrated capability of producing only minute quantities (less than about 1 mg) of recombinant FH and did not provide evidence that they had purified or characterised this material. Furthermore, literature reports likewise allude to sub-milligram quantities of recombinant FH from insect and mammalian cells (e.g. Biologically active recombinant human complement factor H: synthesis and secretion by the baculovirus system. Sharma A K, Pangburn M K. *Gene* 1994 143:301-2; Structural and functional characterization of factor H mutations associated with atypical hemolytic uremic syndrome. Sanchez-Corral P, Perez-Caballero D, Huarte O, Simckes A M, Goicoechea E, LOpez-Trascasa M, de Cordoba S R. *Am J Hum Genet* 2002 71:1285-95.) or to expression of fragments, only, of the FH molecule (e.g. Structure of the N-terminal region of complement factor H and conformational implications of disease-linked sequence variations. Hocking H G, Herbert A P, Kavanagh D, Soares D C, Ferreira V P, Pang burn M K, Uhrin D, Barlow P N.J *Biol Chem* 2008 283:9475-87).

Ormsby, R. J. et al., Expression of human factor H in the methylotrophic yeast *Pichia Pastoris*. Molecular Immunology Vol 35, p. 353, 1998 Abstract 92. This paper uses a *Pichia pastoris* production system to express a FIVE (5) complement control protein (CCP) fragment of Factor H, not the full length TWENTY (20) CCP Factor H protein, which is the subject of present patent application.

Ripoche, J. et al., The complete amino acid sequence of human complement Factor H. Biochemical Journal, Vol 249: 593-602, 1988. This paper describes the full length human factor H nucleotide sequence (and hence the amino acid sequence) and was obtained by sequencing three overlapping cDNA clones spanning the Factor H gene. However, it does not describe how to clone the gene such that it is possible to express functional human Factor H protein.

EP1336618 describes using full length or fragments of porcine Factor H as a soluble complement regulator, for use as a therapeutic. It is suggested that porcine factor H could be purified from pig plasma or as exemplified in this patent, made recombinantly using Baculovirus. However, no quantification of the amount of full length porcine factor H from a standard fermentation nor any functional data for the full length protein (rather than only fragments) is shown. However, there is no disclosure or teaching of how to express functional human Factor H.

The use of porcine Factor H naturally carries the risk of infection with cross-species zoonotic infections. Moreover, there is not complete DNA sequence or amino acid homology between human factor H and porcine factor H (62% homology Hegasy G. A. et al., Pig complement regulator factor H: molecular cloning and functional characterization. Immunogenetics. 2003 October; 55(7):462-71). It is therefore very likely autoantibodies to porcine Factor H would be made, which would again limit therapeutic usage.

WO 2008/135237 describes use of a therapeutic which combines a short consensus repeat (SCR) of Factor H with a pathogen recognition binding molecule e.g. an antibody. It specifically mentions use of fragments/peptide chains of less than 100 amino acids (<2 SCRs). It does not suggest use of a full length Factor H molecule with a pathogen recognition binding molecule. Also, its focus is for the use of treating infections or for cancer, not renal or opthalmological diseases.

Currently, FH-replacement clinical therapy is achieved by means of infusing donated pooled plasma, of which FH is only one of many protein components. It is not possible clinically to routinely obtain plasma containing only the FH Y402 allotype (which is protective against AMD); when purified in bulk from pooled plasma, FH is heterogeneous in terms of both its heterotypic and glycoform variations and hence this material is ill-suited for therapy; antibody-affinity based purification methods generally yield only small amounts (a few mg at most) of material that can be enriched only for a single variant at a specific site of variation (e.g. for Y402) but will be heterogeneous with respect to other polymorphic sites (e.g. V62I). Any use of plasma-purified human proteins would in any case may carry unacceptable risks, of infection with both unknown viral and prion proteins, and of sensitisation to contaminating plasma components, when used on the repetitive basis proposed for AMD, aHUS and DDD therapies.

It is therefore amongst the objectives of the present invention to obviate and/or mitigate at least one of the aforementioned obstacles to therapeutic use of FH.

SUMMARY OF THE INVENTION

The invention is based on work carried out by the present inventors towards providing high-yield production of versions of FH tailored for animal and human trials and therapeutic applications, which is based on the use of codon-optimised chemically synthesised genes that are transfected into, for example and preferably, *Pichia pastoris* followed by expression in a fermentor and purification using a sequence of chromatographic procedures.

In a first aspect there is provided a process for making recombinant mammalian FH, said process comprising the steps of:

expressing in a chosen host organism a codon-optimised nucleic acid sequence which encodes said mammalian FH or variants thereof and which nucleic acid sequence has been codon optimised for expression in a chosen host organism and inserted into an appropriately designed vector; in order to obtain said mammalian FH or variants thereof.

Conveniently, the codon-optimised nucleic acid sequence can initially be chemically synthesised rather than cloned and mutagenised in order to generate the necessary codon optimisation. In accordance with the present invention it is possible to produce large quantities of recombinant mammalian FH and its variants hitherto not possible using the previously described techniques. Typically the methods of the present invention may produce protein yields of at least 0.5 mg of recombinant FH (or its variants) per liter of culture medium, such as at least 1 mg, 5 mg, 10 mg, 50 mg, 100 mg, 200 mg or 500 mg per liter of culture medium. It will therefore be appreciated that it is possible following the methods of the present invention, when using industrial-scale fermentors, to produce hundreds of milligrams or grams or even kilogram-quantities of recombinant FH and variants thereof, which was simply not possible using conventionally cloned recombinantly expressed FH.

The above process may further comprise purifying said proteins from the cell and/or culture medium in which the cell is grown. Purification may typically involve the use of chromatographic methodologies, such as fast-protein liquid chromatographic or high-performance (pressure) liquid chromatographic techniques known in the art. For example, the nucleic-acid sequence may be designed to encode a secretion-signal sequence of amino-acid residues fused to the N-terminus of FH so that FH is secreted into the media (whereupon said signal-sequence peptide is cleaved off) and thereby it is separated from intracellular *P. pastoris* proteins at the outset. In a subsequent purification step, crude material may, for example, be loaded onto an affinity chromatography column, such as a heparin-sepharose column equilibrated in phosphate-buffered saline (PBS), and eluted by application of a gradient, over multiple column volumes, to PBS substituted with high salt (e.g. 1 M NaCl); in a further step, FH-containing fractions from the previous step may be loaded onto, for example, an ion-exchange resin-containing column, such as a GEHealthcare-supplied MonoQ column that has been equilibrated in 20 mM glycine buffer (typically pH 9.5, 150 mM NaCl), and then eluted with a gradient, over many column volumes, with the equilibration buffer at the same pH but substituted with high salt (e.g. 1 M NaCl).

The preferred choice of host organism is *Pichia pestoris* on the grounds that no re-folding of the expressed protein is required, the protein may be secreted into the media and therefore easily accessible, and specific glycoconjugates or non-natural amino acid residues may be incorporated into the recombinant product; but other prokaryotic (e.g. *Escherichia cols*) and eukaryotic (e.g. *Sacchyromyces cerevisiae*) host organisms may also be envisaged.

The mammalian FH referred to may be human FH or FH from another primate or other mammalian FH, such as that from mouse, rat, hamster, rabbit, dog, horse, cow, pig, sheep, camel, cat, guinea pig, or the like.

The deoxyribonucleic nucleic acid (DNA) sequence may comprise unique restriction endonuclease sites at the 5' and 3' ends of the nucleic acid, to facilitate cloning into an appropriately restricted expression vector. Preferred restriction sites are Pstl, BamHl, Notl and Xbal, although others may easily be envisaged by the skilled addressee.

The nucleic acid sequence encoding FH may relate to one of a number of wild-type sequences (known in the art as polymorphic variants) or may be a mutant sequence. The sequence may comprise one or more single-nucleotide polymorphisms known in the art. US 2007/0020647, for example, describes many polymorphisms that have hitherto been identified in the human CFH (the contents of which are hereby incorporated by way of reference) and more such polymorphic variants may be discovered in the future; one or more of these may readily be incorporated into the codon-optimised nucleic acid sequence. Preferred single-nucleotide polymorphisms that may be incorporated, individually or in combination, into the codon-optimised nucleic acid sequence could code for the following variations in the protein sequence: 11e62 (rather than Val), Tyr402 (rather than His), Glu936 (rather than Asp) and/or Arg1210 (rather than Cys) (all numbers refer to the sequence of the encoded protein prior to cleavage of the signal sequence (Swiss-Prot: P08603.4)). Such single-nucleotide polymorphisms and haplotypes have been reported to be associated with a lower-than-average risk of developing AMD (Hageman G S et al. A common haplotype in the complement regulatory gene factor H (HF1/CFH) predisposes individuals to age-related macular degeneration. *Proc Nat/Acad Sci USA* 2005 102:7227-32; Klein R J et al. Complement factor H polymorphism in age-related macular degeneration. *Science.* 2005 308:385-9; Edwards A O et al. Complement factor H polymorphism and age-related macular degeneration. *Science* 2005 308:421-4; Haines J L et al. Complement factor H variant increases the risk of age-related macular degeneration. *Science* 2005 308:419-21; Hageman G S et al. Extended haplotypes in the complement factor H (CFH) and CFH-related (CFFIR) family of genes protect against age-related macular degeneration: characterization, ethnic distribution and evolutionary implications. *Ann Med* 2006 38:592-604). Alternatively or additionally, mutant sequences may be designed to specifically alter the FH polypeptide sequence, for example to include one or more natural (encoded) or non-naturally encoded variant amino acids as described in more detail herein below.

The conjugate refers to a molecule that consists of a polypeptide corresponding to FH or a variant of FH to which is covalently attached, normally via one or more amino-acid residue side-chains, to a chemical moiety or moieties intended to improve the biotherapeutic properties of said molecule. The attached moieties could include: natural polymers such as glycosaminoglycans and their derivatives or polysialic acids, dextran (−1,6 polyglucose), dextran (−1,4 polyglucose), hyaluronic acid, and chitosans; unnatural polymers such as any of a large family of linear or branched polyethylene glycols, polyether polyols, N-(2-hydroxypropyl) methacrylamide copolymers, poly(vinylpyrrolidone), poly(ethyleneimine), or linear polyamidoamines; or pseudosynthetic polymers, such as poly(L-lysine), poly(glutamic acid), poly(malic acid) and poly(aspartamides) (see for example The dawning era of polymer therapeutics. Duncan R. *Nature Reviews Drug Discovery* 2003 2:347-360).

Rather than conventional gene cloning and expression, the present invention is based on an initial chemical synthesis of the codon-optimised DNA molecules encoding said FH (and variants thereof), using gene design and synthesis techniques in the art (e.g. Gene composer: database software for protein construct design, codon engineering, and gene synthesis. Lorimer D, Raymond A, Walchli J, Mixon M, Barrow A, Wallace E, Grice R, Burgin A, Stewart L. *BMC Biotechnol.* 2009 9:36). In this manner, the codon-optimised nucleic acid is synthesised de novo prior to cloning into a suitable expression vector. Conventional site-directed mutagenesis techniques known in the art to carry out codon optimisation of the FH gene would be unfeasibly time-consuming, if not impossible due to the high risk of introducing additional mutational variations during the requisite repeated rounds of site-directed mutagenesis. However, site-directed mutagenesis may be used following cloning of the synthetic codon-optimised CFH, in order to accomplish one or a combination of site-specific mutations in the product Codon optimisation is carried out in order to enhance the expression levels of the mammalian FH and its variants in the desired host organism, such as *P. pastoris*. Said optimisation involves one or more of the following: adapting codon bias to match that of the chosen host organism; avoiding regions of high (>80%) or low (<30%) GC content; minimising any potential internal TATA boxes, chi-sites and ribosome-entry sites; minimising AT-rich or GC-rich stretches of sequence, avoiding repeat sequence and RNA secondary structures, minimising any (cryptic) splice-donor and/or splice-acceptor sites; and ensuring any desired restriction endonuclease sites are only found at the extreme 5' and 3' ends of the nucleic acid to facilitate cloning. Preferably all of the above considerations are taken into account when optimising the nucleic acid sequence. The skilled addressee is able to make such modifications to the original FH sequence based on prior knowledge in the art in relation to the codon bias of the chosen host and other teachings (e.g. Codon bias and heterologous protein expression. Gustafsson C, Govindarajan S, Minshull J. *Trends Biotechnol* 2004 22:346-53). Certain companies such as Geneart (Regensburg, Germany), GeneScript (Piscataway, N.J., USA) and DNA2.0 (Menlo Park, Calif., USA) provide a service for optimising and synthesising nucleic acid sequences that are tailored for expression in a specified host organism.

In a preferred embodiment, the DNA sequence encoding mammalian FH is a CFH sequence which has been optimised for expression in the host, *P. pastoris*. A *P. pastoris* codon-optimised human CFH sequence (encoding for Y at position 402, I at position 62 and E at position 936) is compared to the wild-type cDNA sequence in FIGS. 1A-1E. It will be appreciated that this codon-optimised sequence may be varied in order to still further optimise the sequence for overproduction in *P. pastoris*. Moreover, the sequence may be easily varied in order to allow for expression of various allotypes. Moreover, certain nucleotide bases may be changed in order to specifically alter the amino-acid residue sequence of the FH protein. For instance, certain amino-acid residues may be replaced with, for example, alternative amino-acid residues that may be rare or non-naturally occurring amino-acid residues, so as to allow for the generation of recombinant FH proteins with one or even a combination of modifications leading to: altered glycosylation patterns; reduced immunogenicity; enhanced plasma half-life; and/or site-specific conjugation with moieties designed to improve pharmacokinetic and/or pharmacodynamic properties. It will be appreciated that all such modifications can be carried out whilst taking account of any codon optimisation considerations.

Thus, in a further aspect, the present invention provides a nucleic acid sequence capable of expressing a FH polypeptide or variant thereof, the nucleic acid sequence being codon optimised for expression in a host organism, such as *P. pastoris*. There is also provided a mammalian FH polypeptide or variant thereof, obtained from a nucleic acid sequence according to the present invention.

Preferably the sequence is codon optimised for expression by *P. pastoris*, in which case the nucleic acid sequence may be the codon-optimised human sequence shown in FIGS. 1A-1E or any of the sequences represented in FIGS. 5A-5B, or be substantially similar to them. By substantially similar is understood that the sequence is greater than 70%, 75%, 80%, 85%, 90%, 95% or even 99% identical to the sequence shown in FIGS. 1A-1E or 5A-5B.

The present invention also relates to vectors which include a codon-optimised FH-encoding DNA sequence of the present invention, host cells which are genetically engineered with said recombinant vectors, and the production and purification of the encoded FH and FH-like polypeptides by recombinant techniques, and the conjugated products of said polypeptides.

Recombinant constructs may be introduced into host cells using well-known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides of interest may be contained within a vector containing a selectable marker for propagation in a host. Generally, a plasmid vector is introduced in the form of a precipitate, such as a calcium phosphate precipitate, or in a complex with a charged lipid. If the vector is a virus, it may be packaged in vitro using an appropriate packaging cell line and then transduced into host cells.

Preferred, are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression and may be inducible and/or cell type-specific. Suitable vectors include those inducible by environmental factors that are easy to manipulate, such as temperature and nutrient additives.

Expression vectors useful in the present invention include chromosomal-, episomal- and virus-derived vectors, for example vectors derived from bacterial plasmids, bacteriophages, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter. Known bacterial promoters suitable for use in the present invention include the *E. coli* lacl and lacZ promoters, the T3 and T7 promoters, the gpt promoter, the phage lambda $P_R$ and $P_L$ promoters and the tac and trp promoter. Suitable eukaryotic promoters include the cytomegalovirus immediate early promoter, the herpes simplex virus thymidine kinase promoter, the early and late SV40 promoters, the promoters of retroviral long terminal repeats (LTRs), such as those of the Rous sarcoma virus and metallothionein promoters, such as the mouse metallothionein-I promoter. Promoters specific to *P. pastoris* include alcohol oxidase 1 (AOX1), AOX2 (both methanol inducible), CUP1 (copper inducible), GAP (glycerol inducuble, constitutively active on various carbon sources), FLD1 (formaldehyde dehydrogenase gene), PEX8 (moderate promoter), YPT1 (moderate promoter, constitutively active on various carbon sources), DAS1 (dihydroxyacetone synthase), ADH1 (alcohol dehydrogenase) and PGK1 (3-phosphoglycerate kinase). Other suitable promoters will be known to the skilled artisan, see for example Cereghino and Cregg, 1999, Current Opinion in Biotechnology, 10, p 422-427.

The expression constructs will further contain sites for transcription initiation, termination and, in the transcribed region, a ribosome-binding site for translation. The coding portion of the mature transcripts expressed by the constructs will include a translation-initiating AUG at the beginning and a termination codon appropriately positioned at the end of the nucleic acid sequence to be translated. It is facile, using synthetic genes, to optimise all of these features of the insert to maximise gene-expression levels and recombinant-protein yields.

As indicated, the expression vectors will preferably include at least one selectable marker. Such markers include e.g. dihydrofolate reductase or neomycin or zeocin resistance for eukaryotic cell culture and e.g. tetracycline or ampicillin-resistance genes for culturing in *E. coli* and other bacteria.

Representative examples of appropriate hosts include bacterial cells, such as *E. coli, Streptomyces* and *Salmonella typhimurium* cells; fungal cells, such as yeast cells like *P. pastoris, Kluyveromyceslactis* and *Sacchyromyces cerevisiae*; insect cells such as *Drosophila melanogastor* S2 and *Spodoptera frugiperda* 9 cells; animal cells such as Chinese hamster ovary, COS and Bowes melanoma cells; and plant cells. Appropriate culture media and conditions for the above-described host cells are known in the art. Most preferably the host organism is the methylotropic yeast *P. pastoris*. Strains of *P. pastoris* that have been metabolically engineered so that they attach mammalian or human-like N-glycans may be preferred, see Wildt and Gerngross, 2005, Nature Reviews, 3, p 119-128, Li et al, 2006, Nature Biotechnology, 24, p 210-215, Cereghino, et al, 2002, Current Oinion in Biotechnology, 13, p 329-332.

Vectors preferred for use in bacteria include pA2, pQE70, p0E60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWL-NEO, pSV2CAT, pOG44, pXT1 and pSG available from Stratagene; and pSVK3, pBPV, pMSG and pSVL available from Pharmacia. Vectors preferred for use in *P. pastoris* include pPIC9K, pHIL-D2, pHIL-S1, pPIC3.5K, pGAPZ, pGAPZalpha, pPICZalpha-A, pPICZalpha-B, pPICZalpha-C, pPICZalpha-E, pPICZalpha-E/Uni, pPIC3.5, pPIC9, pPICZ-A, pPICZ-B, pPICZ-C, pPICZ-E from Invitrogen. Other suitable vectors will be readily apparent to the skilled artisan.

As indicated, introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis L G G et al., Basic Methods in Molecular Biology, ($2^{nd}$ Ed., McGraw-Hill, 1995).

As indicated, transcription of the DNA encoding the polypeptides of the present invention by higher eukaryotes may be increased by inserting an enhancer sequence into the vector Enhancers are cis-acting elements of DNA, usually from about 10 to about 300 bp that act to increase transcriptional activity of a promoter in a given host cell-type. Examples of enhancers include the SV40 enhancer, which is located on the late side of the replication origin at bp 100 to 270, the cytomegalovirus early-promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous. Examples of such sequences that may be used in *P. pastoris* include the native human or mouse (or other mammalian) FH-secretion signals and the yeast alpha-mating factor.

The polypeptide of interest may be expressed in a modified form, such as a fusion protein, and may include not only secretion signals, but also additional heterologous functional regions. Thus, for instance, a region of additional amino-acid residues, particularly charged amino-acid residues, may be added to the N terminus of the polypeptide to improve stability and persistence in the host cell, during purification, or during subsequent handling and storage. Also, peptide moieties may be fused to the polypeptide to facilitate purification. Such regions may be removed prior to final preparation of the polypeptide. Additions of peptide moieties to polypeptides in order to engender secretion or excretion, to improve stability and to facilitate purification, amongst others, are familiar and routine techniques in the art.

The FH protein can be recovered and purified from recombinant cell cultures by well-known methods including ammonium sulphate or ethanol precipitation, acid extraction, anion-exchange or cation-exchange chromatography, phosphocellulose chromatography, hydrophobic-interaction chromatography, affinity chromatography, hydroxylapatite chromatography, reverse-phase chromatography, size-exclusion chromatography and lectin chromatography. Most preferably, heparin-affinity is followed by ion-exchange chromatography.

It will be recognised in the art that the amino-acid residue sequence of aFH polypeptide may be selectively varied without having a significantly detrimental effect on the structural integrity or functional properties of the protein. If such differences in sequence are contemplated, it should be remembered that there are regions of the protein that are critical to its biological activity. There will also be residues that are critical to the folding of the protein or for stabilisation of its folded structure. Some residues serve as glycosylation sites, recognised by enzymes that covalently attach glycans to, for example, Asn side-chains. In general, it may be possible to safely replace residues that contribute directly or indirectly to structure or function by other residues that are chemically similar (this is known as a conservative substitution). In the cases of amino-acid residues that contribute neither to structural integrity nor to functional sites, it may be possible to safely replace such a residue with an amino-acid residue of a different chemical nature (a non-conservative replacement).

Thus, the invention further includes variations of the FH polypeptide which variants show substantially FH-like biological activity. Variants might include conservative substitutions (for example, substituting one hydrophilic residue for another, or one hydrophobic residue for another), but would be unlikely to include replacements of strongly hydrophilic residues for strongly hydrophobic ones (or vice versa). Variants might include conservative substitutions within N-glycosylation sites that result in loss of such sites. Variants may also include deletions of one or more of the 20 protein domains within the FH molecule. For example, deletion of one or a combination of domains [such as 2, 3, 4, 5, 6, 7, 8, 9, 10 or 11 domains] between and including domains 8 and 18 would be unlikely to have a detrimental effect on the functionally critical individual binding sites located in domains 1-4, 6-7 (or 6-8) and 19-20. Variants could also include deletions of one or a combination of domains from the region of FH between and including domains 5-18 since this would preserve C3b-binding sites (1-4, and 19-20) and one (in 19-20) of two cell surface-recognition sites within FH (see e.g. A new map of glycosaminoglycan and C3b-binding sites on factor H_ Schmidt C O, Herbert A P, Kavanagh D, Gandy C, Fenton C J, Blaum B S, Lyon M, Uhrin D, Barlow P N. *J Immunol,* 2008, 181:2610-9) and might enhance functional activity by optimising the spatial positioning, or flexibility of the connection, between these binding sites. Variants might also include hybrids, in which, for example one or more deleted domains from the domains 8-18, or 5-18, regions of FH are replaced with one or more similar domains derived from other proteins, for example from complement receptor type I or type II; alternatively they might be replaced by one or more dissimilar domains derived from a wide range of other proteins such as proteins of the extracellular matrix or the clotting or complement cascades.

Typically seen as conservative substitutions are the replacements, one for another, amongst the aliphatic amino-acids Ala, Val, Leu and Ile; interchange of the hydroxyl residues Ser and Thr; exchange of the acidic residues Asp and Glu; substitution between the amide residues Asn and Gln; exchange of the basic residues Lys and Arg; and replacements amongst the aromatic residues Phe and Tyr. Non-conservative substitutions could include substitutions with both naturally encoded amino-acid residues and a non-naturally encoded (unnatural) amino-acid residue. The unnatural amino-acid residue could be one that serves as a site-specific attachment sites for conjugation with chemical moieties (such as polyethylene glycols (PEGs) and other polymers), or with biochemical groups (such as glycans) that enhance the therapeutic efficacy of FH.

As indicated in detail above, further guidance concerning which aminoacid changes are likely to be phenotypically silent (i.e. are not likely to have a significant deleterious effect on a function) can be found in Bowie, et al., "Deciphering the Message in Protein Sequences: Tolerance to Amino Acid Substitutions," *Science* 247:1306-1310 (1990).

Also of interest are substitutions that prevent aggregation or minimise proteolysis. Aggregation of proteins not only results in a loss of activity but can also be problematic when preparing pharmaceutical formulations, because aggregates can be immunogenic (see, e.g. Pinckard et al., *Clin Exp. lmmunol,* 1967, 2:331-340; Robbins et al., *Diabetes,* 1987, 36:838-845; Cleland et al., *Crit. Rev. Therapeutic Drug Carrier Systems,* 1993, 10:307-377). Aggregation may be minimised by changing surface residues, for example removing hydrophobic patches (by substituting hydrophobic residues with polar ones) or by changing the electrostatics at the surface by charge-reversal (e.g. by substituting Asp for Arg or Glu for Lys) or deletion (e.g. substituting Ser for Asp). Proteolysis results in a loss of the target protein thus lowering yield and also makes purification more difficult. Proteolysis may be reduced by recognition of proteolytic sites via computational prediction or empirical means and conservative substitutions therein.

Possible modifications of particular relevance to mammalian FH include mutating one or more Asn residues to Gln residues in order to minimise glycosylation of the FH protein. Alternatively one or even two Asn residues of the FH protein may be replaced by any of a large number of unnatural amino-acid residues, such as p-(propargoxy)-phenylalamine (pPpa) residues (Expanding the genetic repertoire of the methylotrophic yeast *Pichia pastoris*. Young T S, Ahmad I, Brock A, Schultz P G. *Biochemistry* 2009 48:2643-53). Such an unnatural residue could be further modified by PEGylation or sialylation techniques known in the art.

Thus, in a further aspect, the present invention provides a recombinantly expressed variant of mammalian, especially human, FH obtained from a codon-optimised nucleic acid wherein the variation comprises one or more amino-acid residue substitutions designed to modulate one or more biological properties of said FH variant as compared to a native FH.

It will be understood that said amino acid substitution(s) do not relate to polymorphic changes to the FH protein, as known in the art. Said substitution(s) may result in modulation of, for example, immunogenicity and/or a physiological property of said FH variant as compared to a native FH. Exemplar modifications include substituting one or more Asn residues for another amino acid residue, such as Gln, or a non-naturally occurring amino acid residue, such as pPpa, in order to vary the glycosylation state of said FH variant and/or allow further modification of said FH variant using chemistry known in the art in order to allow the variant to be specifically modified at said substituted sites by a molecule such as PEG or polysialyl chains.

Thus, the target FH-like polypeptide may be: (i) one in which one or more of the amino acid residues are substituted with a conserved or non-conserved amino acid residue and such substituted amino acid residue may or may not be one encoded by the genetic code; or (ii) one in which one or more of the amino acid residues is conjugated with another molecule or includes a substituent group; or (iii) one in which the mature polypeptide may be covalently linked to another compound or compounds, such as a compound to increase the half-life of the polypeptide (for example, PEG or polysialic acid); or (iv) one in which additional amino acid residues are fused to the mature polypeptide, such as an IgG Fc fusion-region peptide or leader or secretion-signal sequence or a sequence which is employed for purification of the mature polypeptide or a pro-protein sequence; or (v) one with an altered (compared to the native glycoforms of FH) pattern of attached glycans due to substitutions within glycosylation sites or introduction of new glycosylation sites (or unnatural amino acids suitable for chemical conjugation with glycans) or employment of strains of *P. pastoris* with engineered glycosylation pathways; or (vi) domain-deletion or hybrid variants in which domains have been removed from the central portion of FH and may or may not have been substituted with homologous or other domains from other proteins. Such fragments, derivatives, conjugates and analogues are deemed to be within the scope of those skilled in the art from the teachings herein.

The recombinantly expressed mammalian FH polypeptides and variants of the present invention may find a variety of applications. For example the polypeptides/variants may be used therapeutically to treat or prevent age-related macular degeneration (AMD) or to prevent or slow the progression of this disease, in genetically susceptible individuals and facilitate treatment in those with AMD, as well as in the treatment/prevention of two life-threatening kidney conditions known as atypical haemolytic uraemic syndrome (aHUS) and dense deposit disease (DDD). The recombinantly expressed mammalian FH of the present invention could have beneficial effects in the treatment or prevention of numerous other diseases or pathologies in which inadequate complement regulation contributes to aetiology or symptoms, for example Alzheimer's disease, ischemia, pre-eclampsia, early pregnancy loss, sepsis, multiple sclerosis, system lupus erythematosus and transplant rejection. See for example, lschaemia-Reperfusion Injury: (Shah K G et al, *J Surg Res.* 2010 163 1:110-117; Yang J et al, *Ann Surg.* 2009 249 2:310-317; Zhang F et al, *Regul Pept.* 2009 8 52(1-3): 82-87, Organ Transplantation: Atkinson C, et al, *J Immunol.* 2010 185 11:7007-7013, Early Pregnancy Loss: Lynch A M, et al, *Obstet Gynecol.* 2011 117 1:75-83 and Pre-eclampsia Qing X et al, *Kidney Int.* 2010 Oct. 13. [Epub ahead of print].

The recombinant FH polypeptides and variants in accordance with the present invention may also find application in research and also in kits and the like.

Particularly preferred FH molecules and variants according to the present invention are described in detail below.

DETAILED DESCRIPTION

The present invention will now be further described by way of example and with reference to the figures which show:

FIGS. 1A-1E show DNA sequence (Swiss-Prot: P08603.4) of native human FH; Sequence of *P. pastoris* codon-optimised human FH of the present invention; and an alignment of the wild-type (cDNA-derived) and codon-optimised FH gene sequences.

FIG. 2 shows western-dot-blot results from non-codon optimised FH gene expression.

Figure 3A:
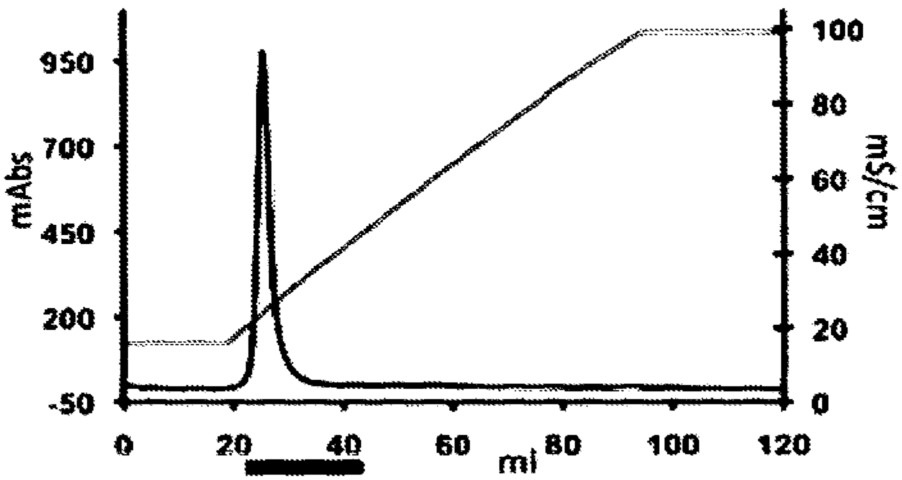
FIGS. 3A-3J shows production and characterisation of recombinant complement factor H.

FIG. 3A—Elution from an anion-exchange column (MonoQ) ($A^{280}$ in milli-absorbance units on left-hand y-axis) with a salt gradient (20 mM glycine buffer, pH 9.5, 0.12-1 M NaCl; conductivity on right-hand y-axis).

Figure 3B:
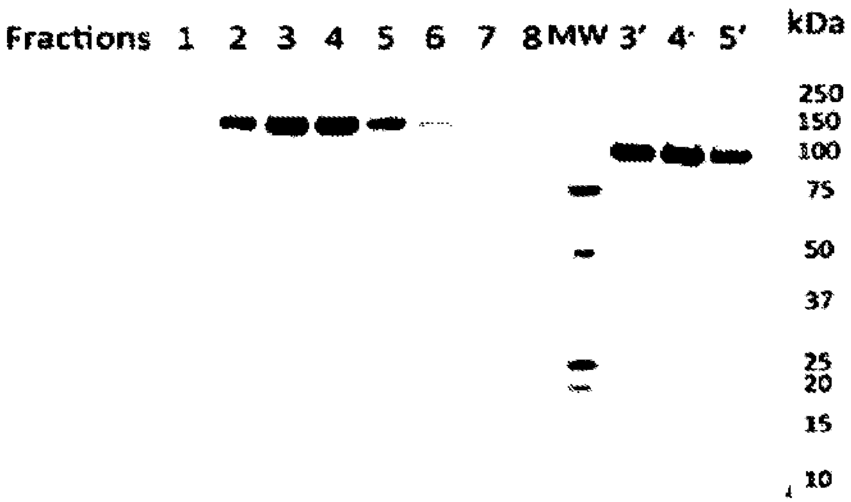

FIG. 3B—Fractions eluted from the MonoQ column (see FIG. 3A) were subjected to SDS-PAGE and protein bands were visualised with Coomassie blue. Lanes 1-8 (reducing conditions—i.e. no disulfides present) correspond to elution volumes 23-30. No significant "clipping" of the polypeptide chain is evident. Lane 9 contains molecular weight markers (MW) as indicated on the right-hand side. Lanes 3', 4' and 5' correspond to lanes 3, 4 and 5 but were run under non-reducing conditions; the faster migration of bands in lanes 3', 4', and 5' (compared to lanes 3, 4 and 5) is typical for proteins that contain disulfide bonds.

Figure 3C:
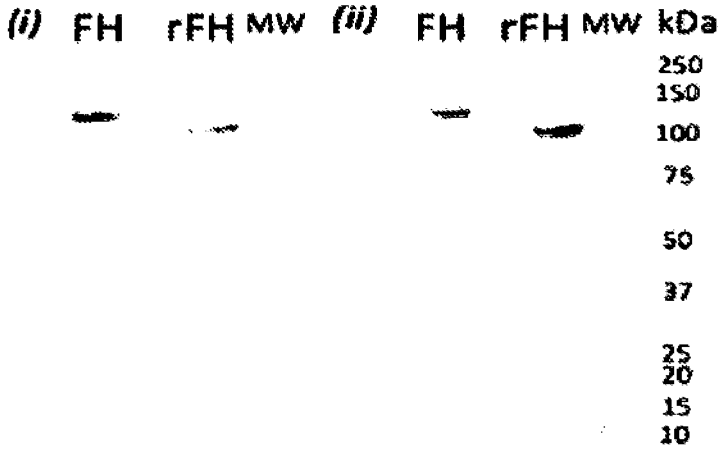

FIG. 3C—Two antibodies that recognise epitopes within the C-terminal CCP modules (domains) of FH, were used in western blots. Plasma FH (left lane) and recombinant rFH (middle lane) were detected with (i) MAb-SC47686_L20/3 or Mab-Abnova-0167. MW=molecular weight markers—see right-hand side of gel (ii).

Figure 3D:
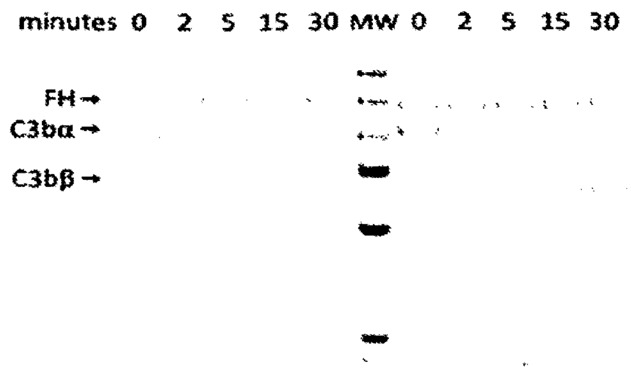

FIG. 3D—The abilities of FH (lanes 1-5) and rFH (lanes 7-11) to act as cofactors for factor I-catalysed cleavage of C3b to iC3b were assessed by visualising the 43-kDa and 68-kDa proteolytic fragments of the a'-chain using SDS-PAGE followed by Coomassie blue staining. Incubation times were 0 to 30 minutes, as indicated. Both versions of FH have similar activities in this semi-quantitative assay such that the a'-chain of C3b is completely processed within five minutes. MW=molecular weight markers of (from top) 250, 150, 100, 75, 50, 37, 25 and 20 kDa.

Figure 3E:
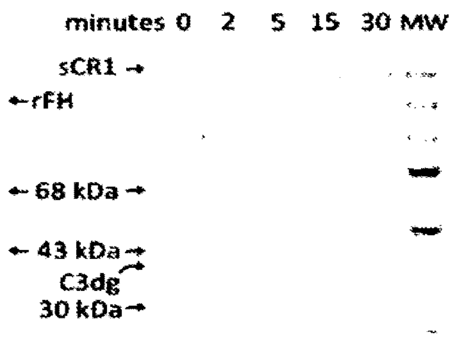

FIG. 3E—For comparison with FIG. 3D, the cofactor activity of soluble complement receptor type 1 (sCR1), at the same concentration was followed over the same time intervals. Note that (in agreement with literature) sCR1, but (from FIG. 3D) neither rFH nor plasma-purified FH, promoted the further degradation of the a'-chain to C3dg and a 30-kDa fragment. MW, as in FIG. 3D.

Figure 3F:
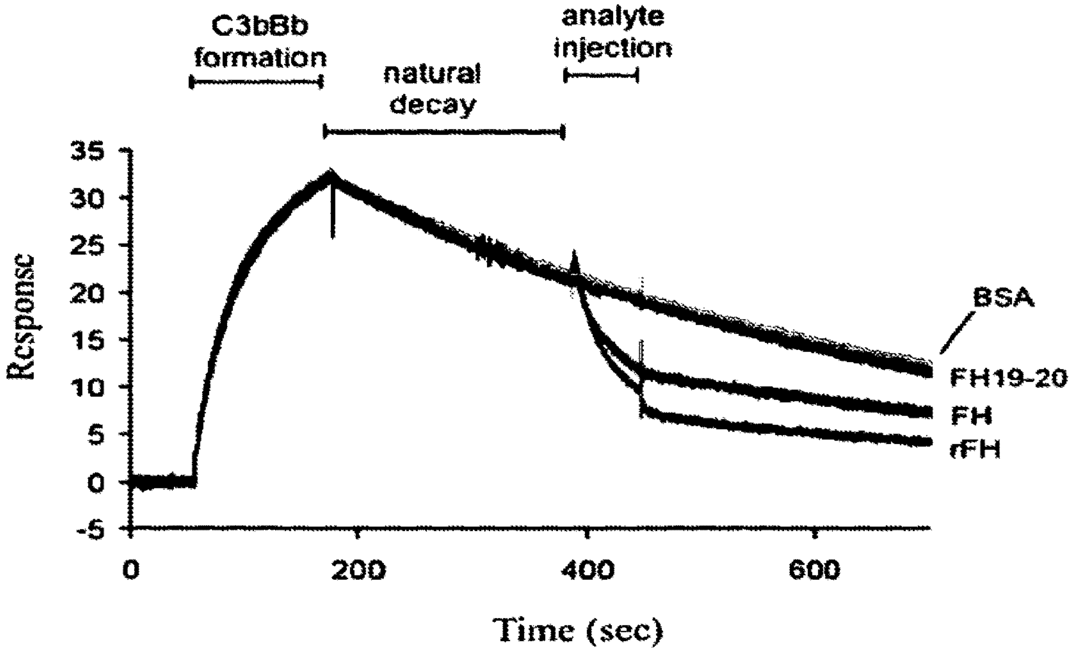

FIG. 3F—Surface plasmon resonance was used to monitor formation of the C3bBb (convertase) complex as factor D and factor B were flowed together over C3b that was amine-coupled to a CMS (Biacore) sensor chip. The subsequent decline in response reflects decay of the complex as Bb is released from the chip surface. The rate of decay is accelerated by initiating (in this case 210 s into the natural decay process) a flow of reference FH or rFH. At similar concentrations (0.5 1 AM), rFH is a more effective decay accelerator in this assay than plasma-purified FH. The control proteins, BSA and FH modules 19-20, have no effect on decay.

Figure 3G:
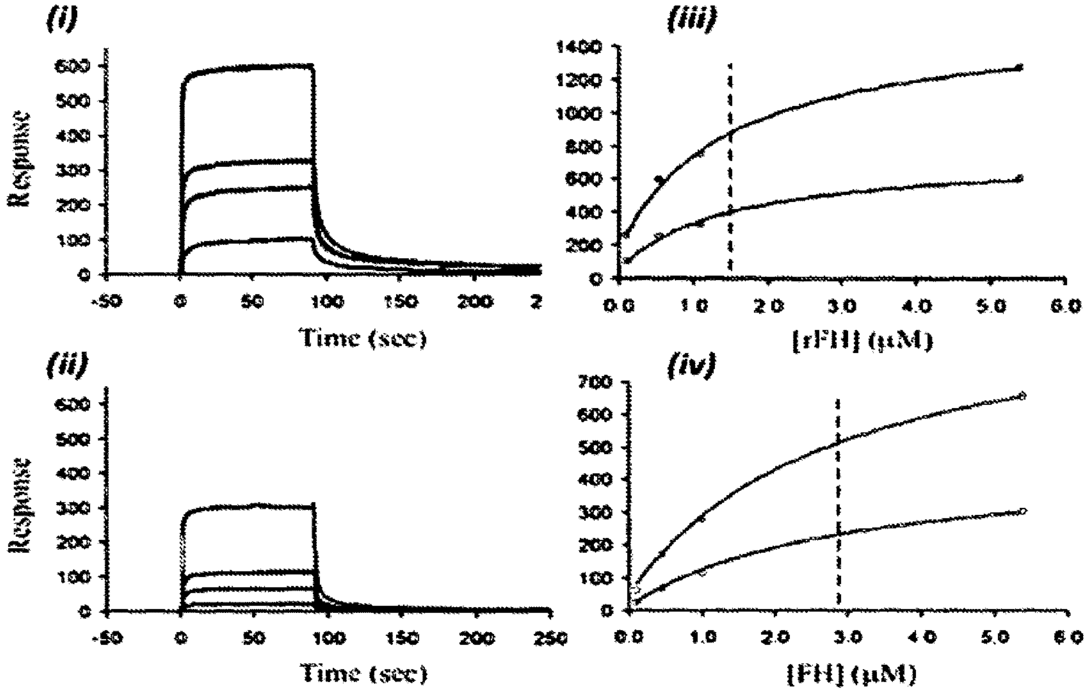
Figure 3H:
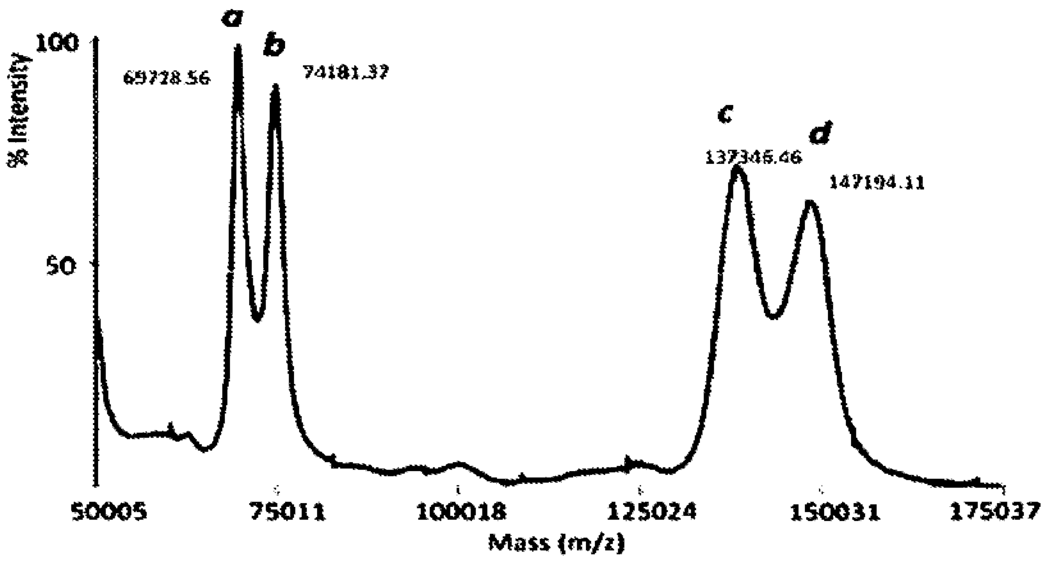
Figure 3I:
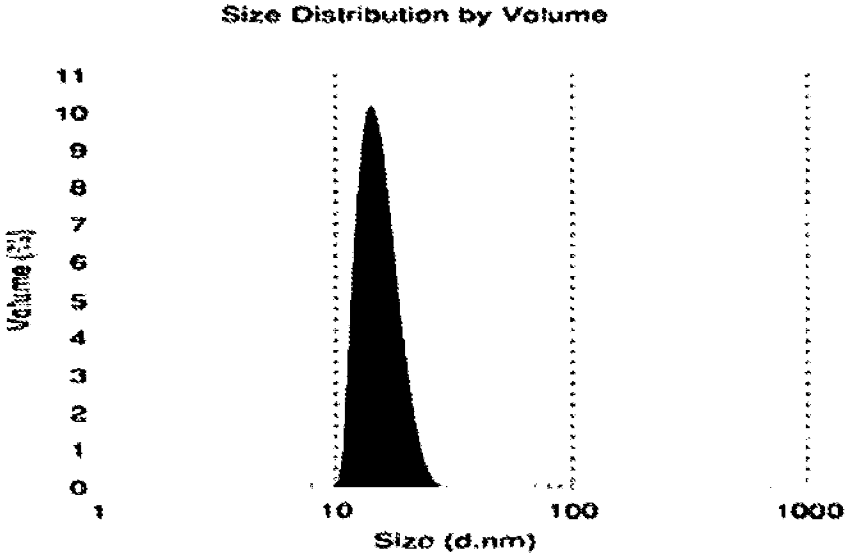

FIG. 3G—(i) and (ii)—Use of SPR to measure affinity of (i) rFH and (ii) plasma-purified FH for C3b coupled to aCM5 sensor chip (Biacore). Duplicate sensorgrams are shown for a concentration series (5.4 μM, 1.0 TIM, 0.5 JAM, 0.1 μM) flowed over 1540 response units of immobilised C3b.

(iii) and (iv)—Plots of response units versus (iii) rFH or (iv) plasma-purified FH concentrations for two different flow cells with either 1540 RUs (lower curve in each plot) or 3030 RUs (upper curve in each plot) of C3b. The dashed vertical line indicates the KD fitted in each case to both plots simultaneously, and yielding 1.4 μM for rFH and 2.9 μM for plasma-purified FH.

FIG. 3H—The candidate recombinant FH (peaks a and c correspond to double-charged and single-charged species, respectively) and an internal standard ($IgG_I$; peaks b and d correspond to double-charged and single-charged species, respectively) were analysed on a MALDI-ToF mass spectrometer.

FIG. 3I—Dynamic light scattering was performed on rFH in PBS at a concentration of 1 mg/ml.

Figure 3J:
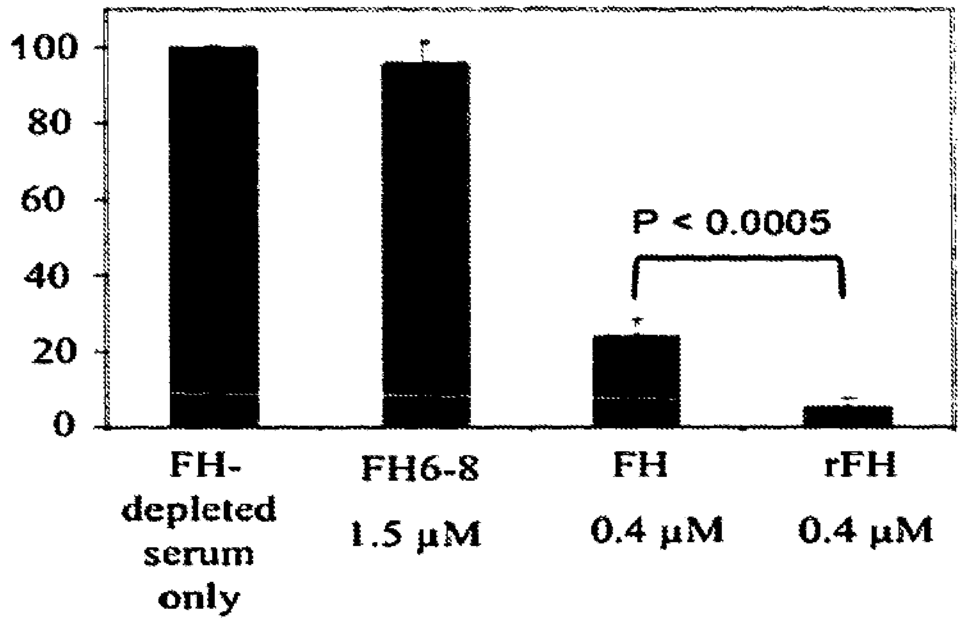

FIG. 3J—Sheep erythrocytes were incubated in physiological buffer, with 1.5 1 AM FH modules 6-8 (negative control), 0.4 FLM plasma-purified FH or 0.4 mM rFH prior to exposure (for 20 minutes at 37° C.) to human serum that had been depleted of FH. The reaction was quenched and A412 was measured. The results shown were the average (plus or minus standard deviation) of four experiments.

Figure 4A:
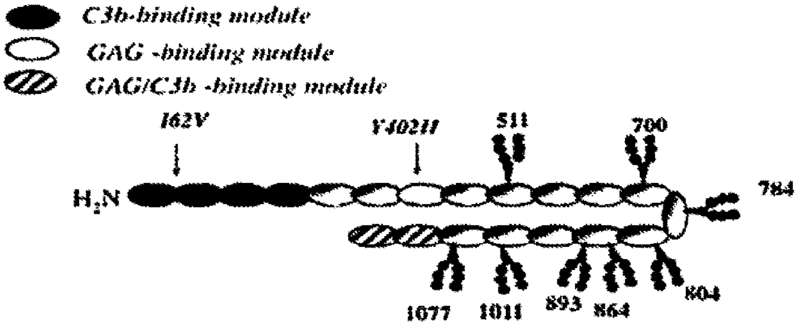
Figure 4B:
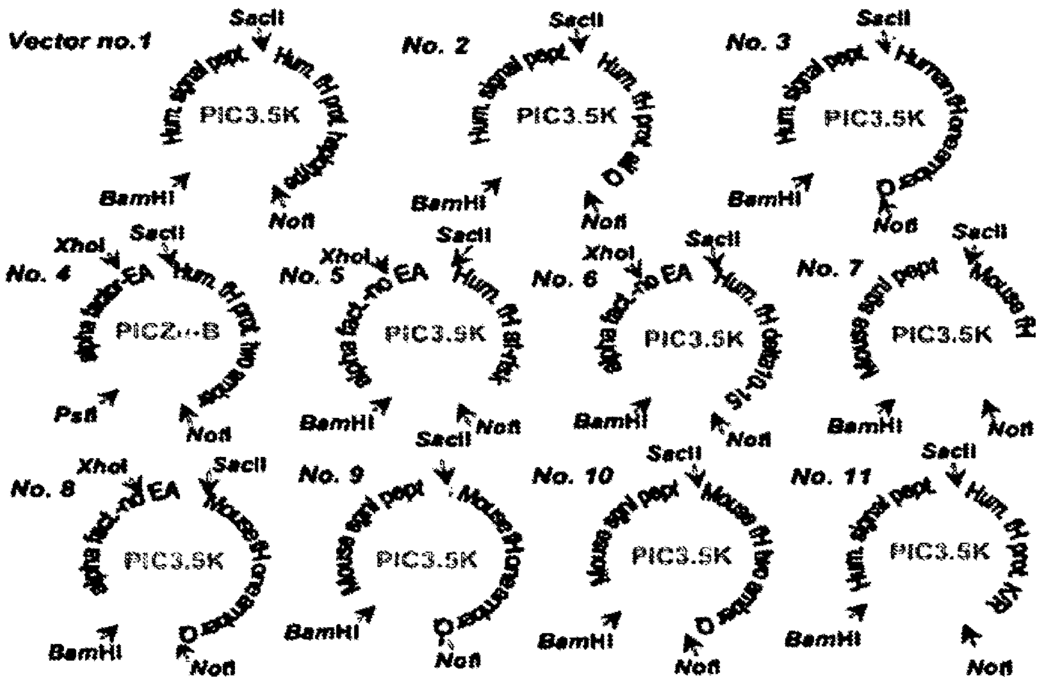

FIG. 4A shows a schematic representation of human factor H (FH) showing certain SNP's and the eight N-linked glycans. FIG. 4B shows schematic representations of vector (plasmid) maps designed such that various FH molecules and variants can be prepared in accordance with the present invention. All except vector 4 (based on pPICZα-B) are based on pPIC3.5K. Vector numbers 1-3 and 11 incorporate DNA for the human secretion signal peptide (hum. signal pept.) while vector numbers 7, 9 and 10 incorporate the mouse equivalent. The other four vectors incorporate DNA for the yeast alpha-factor peptide with (vector number 4) or without (vectors 5, 6 and 8) EA dipeptides. The encoded variants of FH (sequences in FIGS. 5A-5B) are indicated—the protective (prot.) and at-risk haplotypes are detailed in the text; "all-Q" and "one amber Q" or "two amber 0" refer to substitutions of Asn residues for Gln and one or two pPa residues (for example), respectively, as described in the text; "delta 10-15" indicates removal of FH domains 10-15 as described in the text; K/R indicates substitution of lysines and arginines with glutamines as described in the text.

FIGS. 5A and 5B are a summary of DNA sequences encoding (a) human and (b) mouse FH variants that have been inserted into vector numbers 1-11.

FIG. 6 illustrates the expression of two recombinant variants of FH. The sample of "all-Q" mutant of rhFH (left-hand gel) migrates as a single band during SDS-PAGE under reducing (R) and non-reducing (NR) conditions (stained by Coomassie blue). Endo Hf (77 kDa) treatment causes no change in migration rate. This is consistent with the "all-Q" mutant having no N-glycosylation sites and being glycan-free. For comparison (middle gel), rhFH (prior to purification) migrates as a fuzzy band until it is Endo Hf treated (right-hand gel). The sample of "delta10-15" rFH was eluted from an anion-exchange column and six peak fractions collected and run on SDS-PAGE under reducing (R) or (for four fractions) non-reducing (NR) conditions (right-hand gel), then stained with Coomassie blue. MW=molecular weight markers as indicated to left and right of the gels.

FIG. 7 is a schematic summary of a route to therapeutic versions of FH.

EXAMPLE 1—ATTEMPTED EXPRESSION OF NON-CODON-OPTIMISED DNA ENCODING FH

Human FH-encoding DNA was amplified from cDNA, and inserted into the yeast expression vector pPICZalphaB, and KM71 H *P. pastoris* cells were duly transformed. Cell colonies grew on high antibiotic-containing plates, consistent with the presence of multiple copies of the gene in the transformed cells. We failed, however, to detect (on SDS-PAGE, stained with Coomassie Blue) any evidence of FH expression in mini-scale cultures. Nor was any detectable recombinant FH produced in shaker-flask cultures. We next checked to see if protein expression by transformed cells could be detected under ideal expression conditions (as may be achieved in a one-liter fermentor in which oxygen and nutrient levels are maintained at near-optimal levels) and by using more sensitive detection methods (Western-dot-blot, see FIG. 2); notwithstanding these steps and even with the additional use of a larger-scale (three-liter) fermentation, no recombinant FH product could be detected.

In further attempts to find evidence for the expression of even small amounts of recombinant FH, a portion of the supernatant was concentrated (for Western-dot-blot) while the remainder was diluted (to reduce salt concentration) and loaded onto a HiTrap (GE Healthcare) heparin-affinity chromatography column at pH 6. A sample from a one-step elution (expected to wash all of the protein off in a small volume) with 1 M NaCl (in the equilibration buffer used for the HiTrap heparin column) was also assayed in a Western-dot-blot.

Detection was attempted using a standard Western-blotting technique with both a commercial polyclonal anti-FH antibody and secondary antibody coupled to horseradish peroxidase. With the exception of the positive controls (consisting of the primary anti-FH antibody, the secondary antibody, and human plasma-derived FH purchased from Complement Technology, Texas) no positive signal was detectable (see FIG. 2).

Thus, we demonstrated that provision of multiple-milligram, let alone multiple-gram, quantities of recombinant FH from wt FH-encoding DNA, despite the use of a heterologous expression system that is known to be particularly suitable for extracellular proteins containing disulfides and that has been used for expression of shorter segments of FH, is far from a straightforward matter.

EXAMPLE 2—DEVELOPMENT. PURIFICATION AND CHARACTERISATION OF CODON-OPTIMISED HUMAN FACTOR H

Codon optimisation aimed at human FH expression in *P. pastoris* was carried out by consultation between the inventors and Geneart (Regensburg, Germany) using their proprietary techniques and Gene Optimizer® software.

The nucleic acid sequence of a codon-optimised form of human FH, for expression in *P. pastoris*, is significantly different (it has 76% sequence identity) to the native DNA sequence (see FIGS. 1A-1E).

The codon-optimised DNA sequence was synthesised by Geneart and then cloned into an Invitrogen-purchased *P. pastoris*-based expression vector, pPICZ alpha B-vector, which had been restricted using appropriate restriction enzymes.

The vector was transformed into *E. coli* in order to amplify the DNA, yielding several 10 s of pg of plasmid DNA. This was purified, linearised (to enhance homologous recombination) and then transformed (using electroporation) into *P. pastoris* strain, KM71 H. Selection of *P. pastoris* clones containing the expression plasmid was achieved by streaking transformed yeast onto rich-media plates containing a range of concentrations of an antibiotic marker. Colonies that grew on high antibiotic-containing plates were screened for protein expression.

After filtration to remove cells, the supernatant from the fermentor was diluted one-in-five with distilled water and applied to a self-poured XK-Heparin column (Heparin Fast-Flow resin—from GE Healthcare). Elution was accomplished with a linear gradient, over six column volumes, from 20 mM potassium phosphate buffer (pH 6.0) to the same buffer substituted with 1 M NaCl. Fractions containing protein were pooled and the glycans were removed by incubating the sample with Endoglycosidase H-mannose binding protein fusion protein (Endo Hf, New England Biolabs) at 37° C. Protein was then applied to a Concanavalin A (GE Healthcare) column and then to mannose-binding-resin (New England Biolabs) to remove *P. pastoris*-derived glycans and the Endo $H_f$. As an alternative to Endo $H_f$, an exoglycosydase may be utilised so as to retain more of the glycans on the recombinant product, which might enhance solubility.

The sample was further purified on a self-poured Poros-Heparin chromatography column and eluted, over 20 column volumes, with a linear gradient from PBS to PBS plus 1 M NaCl. The final purification step involved anion exchange on a MonoQ column. The protein was eluted by a gradient, over 20 column volumes, from 20 mM glycine buffer (pH 9.5) to the same buffer supplemented with 1 M NaCl.

Exemplary results of such a purification, followed by extensive biophysical and functional characterisation and validation, are shown in FIGS. 3A-3J. The yield of protein from this procedure, that had not been optimised, was about 1.5-2.5 mg of protein from one liter.

EXAMPLE 3—FURTHER DEVELOPMENT OF HUMAN AND MOUSE FH VARIANTS USING CODON-OPTIMISED DNA; ELABORATION TO ENHANCE THERAPEUTIC EFFICACY

In a first step, a set of 11 plasmid vectors (vector numbers 1 through 11) was designed by the inventors (FIGS. 4A-4B) in order to further exemplify the utility and versatility of expression of a synthetic codon-optimised gene in *P. pastoris*. This set of vectors was designed so as to allow "cutting and pasting" of DNA encoding FH between vectors so as to maximise the number of secretion pathways that could be easily explored for each of the targeted FH variants. The aim was to produce mouse FH in addition to human FH, since mouse FH is needed for trials in mice.

In a second step, the 11 DNA inserts (see FIGS. 5A-5B for sequence information) intended for codon optimisation were designed by the inventors based on (i) the desired amino acid residue sequences, (ii) the requirement for suitable endonuclease restriction sites, (iii) the incorporation of appropriate secretion signal sequences (peptides) at the N termini of the target proteins to promote secretion into the growth media, (iv) pursuit of the strategies summarised in FIG. 7 aimed at amassing the information required to optimise a biotherapeutic product derived from FH.

In a third step, codon optimisation and gene synthesis to create construct numbers 1 through 11 (summarised in FIGS. 5A-5B) were carried out by Geneart (Regensburg, Germany) using their proprietary techniques and GeneOptimizer® software. Geneart were also contracted to incorporate the 11 constructs into inventor-supplied plasmids to generate vector numbers 1 through 11 (FIGS. 4A-4B).

In the production of recombinant human (rhFH) described in Example 2 we employed a pre-pro leader (signal) sequence to direct secretion of rhFH, thereby facilitating purification. In that work, the pro-region was separated from the target sequence by an endopeptidase (kex2 protease)-cleavage site followed by two Glu-Ala dipeptides introduced to enhance cleavage-site accessibility. Native sequence generation relied upon kex2 protease to remove the pro-region, followed by dipeptidyl aminopeptidase action of the stel 3-gene product to perform Glu-Ala removal. Incomplete cleavage by ste 13 sometimes resulted in potentially immunogenic N-terminal Glu-Ala pairs. To eliminate this possibility, codons encoding one or both of said Glu-Ala dipeptides were avoided during creation of vector number 1 and additionally construct 1 was designed to exploit the native secretion signal sequence of hFH and processing by yeast secretion-pathway enzymes. Hence, using vector number 1 the N-terminal expression artefact ($NH_2$-Glu-Ala) that was included in our initial recombinant hFH is absent, and the presence of a previously present cloning artefact (Ala-Gly)

is circumvented; in addition, using vector number 1, rhFH is in effect mutated to yield the protective haplotype (162, Y402) (creating IY-hFH).

*Pichia pastoris* normally introduces high mannose-type N-glycans at Asn-Xaa-Thr/Ser sequons resulting in heterogenous, potentially immunogenic, products. These glycans lack terminal sialic acids and are probably susceptible to rapid clearance via hepatic asialoglycoprotein receptors. On the other hand, glycosylation may assist folding and stability of the recombinant protein and in the original study we removed *P. pastoris* N-glycans from rhFH enzymatically after expression and before purification or after the first purification step. Construct number 2 was designed so that Asn residues at N-glycosylation sites are replaced with Gln residues (FIGS. 5A-5B) (to create allQ-IY-hFH). Thus vector number 2 allows assessment of the consequences of producing FH lacking eight normally occupied (out of nine potential) N-glycosylation sequons by mutating the relevant Asn residues to GIn residues. Thus using vector number 2 we produced, secreted (relying on the human-FH secretion signal sequence) and purified allQ-IY-hFH corresponding to the protective haplotype but with no N-glycosylation sites (see FIG. 6). We demonstrated that this material was glycan-free on the basis that no difference was observed in migration on SDS-PAGE before and after treatment with Endo Hf.

Construct 3 exploits the amber codon to allow replacement of a potentially N-glycosylated Asn residues in/Y-hFH with an unnatural amino acid such as p-(propargoxy)phenylalanine (pPpa) (to create unN-IY-hFH) (see FIGS. 5A-5B). Low long-term immunogenicity and enhanced half-life are essential properties in biotherapeutics suitable for supplementation of human FH function in patients. Attachment of poly(ethylene) glycols (PEGs) is a proven strategy in this respect (see e.g. PEGylation, successful approach to drug delivery. Veronese F M, Pasut G. *Drug Discov Today.* 2005; 10:1451-8). Alternatives to PEGylation include conjugation with biodegradable polysialic acid chains that may have advantages over PEGs where high and repeated doses are involved (see e.g. Improving the therapeutic efficacy of peptides and proteins: a role for polysialic acids. Gregoriadis G, Jain S, Papaioannou I, Laing P. *Int J Pharm* 2005 300:125-30). It will be understood that numerous other polymers could be conjugated to hFH to improve its biotherapeutic potential. Randomly placed PEGylation or polysialylation for example, on primary amines is straightforward but frequently results in a heterogenous product and steric interference with binding regions on the protein. Far more desirable is site-specific modification. We are able to exploit this desirable option thanks to our use of *P. pastoris* as our preferred expression system. Indeed, a very significant advantage of *P. pastoris* over a non-yeast eukaryotic expression system is the possibility of easily replacing one or possibly two relevant Asn residues with non-naturally encoded amino acid residues (this is possible with other eukaryotic expression systems but is less straightforward and would not be expected to produce protein in the required yields).

Thus by transfecting *P. pastoris* with vector number 3, along with a plasmid carrying the requisite tRNAs and aminoacyl tRNA transferase, we introduce the option of site-specific covalent modification with a chemically synthesised polymer that should mask the altered residue and eliminate a glycosylation site while potentially enhancing other biotherapeutic properties of the protein. It should be noted that these residues are not directly involved in binding to other proteins since they are normally N-glycosylated and they lie within modules of FH that we have previously shown not to be involved in C3b or GAG-binding. The system for incorporation of an unnatural amino acid used is the one developed by Schultz (Expanding the genetic repertoire of the methylotrophic meast *Pichia pastoris*. Young T S, Ahmad I, Brock A, Schultz P G. *Biochemistry* 2009 48:2643-2653) for incorporation of pPpa that is suitable for side-chain modification using "click" chemistry. This utilises an orthogonal tRNA/tRNA and aminoacyl-tRNA synthetase pair developed in *E. coli* using directed evolution. This allows, in the first place, the biological and biophysical properties of unN-IY-hFH to be compared to those of /Y-FH (after enzymatic deglycosylation) and allQ-IY-hFH. It will be understood that another unnatural amino acid could be incorporated instead of pPpa, which would provide alternative chemical routes to conjugation; for example, we could incorporate an unnatural amino acid with an azo-group or other reactive group. Many such possibilities are discussed in the above-cited paper by Young et al the contents of which are hereby incorporated in its entirety by reference. It will also be understood that other residues besides the Asn residues in N-glycosylation sites, for example the Ser or Thr residue that is found two residues after the Asn residue, could be replaced with unnatural amino acids.

Subsequently, click chemistry is utilised to PEGylate unN-IY-hFH creating our candidate therapeutic product, PEGylated-hFH (FIG. 7); for comparison, we non-specifically PEGylate Lys residues within allQ-IY-hFH (to create $PEG^x$-hFH). The creation of these proteins is as follows. Azo-derivitised PEGs are available commercially and these react with the propargyl group of pPpa in a Cu(I)-catalysed azide-alkyne cycloaddition to give a high yield of the 1,2,3-triazole. It will be understood that it is possible to incorporate azo-amino acid residues instead of pPpa and then to use propargyl-PEG as a conjugate. It will also be understood that conjugations with other polymers would be equally feasible. In this way we create site-specifically PEGylated versions of FH. It is possible to explore different chain lengths, and the use of branched chains. For comparison with the products of site-specific conjugation, we use well-established protocols that randomly conjugate succinamide-ester activated PEGs to primary amines of the recombinant protein (see Peptide and protein PEGylation: a review of problems and solutions. Veronese F M. *Biomaterials.* 2001, 22:405-17 and references therein). Using homogenous preparations of activated PEGs at appropriate stochiometric ratios and by fractionating and characterising the products, one obtains well-defined positional isomers of mono/di-PEGylated protein. These operations are performed on IY-hFH creating PEG"-IY-hFH. Thus it is possible to compare the relative merits of site-specific and random PEGylation. It will be understood that a similar approach may readily be extended to polysialylation instead of PEGylation.

With regard to comparisons of the various products—e.g. hFH, FY-hFH, allQ-IY-hFH, unN-IY-hFH, PEG-hFH and $PEG^x$-hFH—we explore their C3b- and GAG-binding properties and their bioactivities. Thus, pure and authenticated samples are tested for the following: (i) Ability to act as a cofactor for factor I-catalysed cleavage of C3b (see FIG. 3D) (Enzymic assay of C3b receptor on intact cells and solubilised cells. Sim E, Sim R B. *Biochem* 1 1983, 210: 567-76); (ii) Ability to promote acceleration of decay of C3bBb assembled on a surface plasmon resonance (SPR) sensor chip (Decay-accelerating factor must bind both components of the complement alternative pathway C3 convertase to mediate efficient decay. Harris C L, Pettigrew D M, Lea S M, Morgan B P. *J Immunol.* 2007 178:352-9)(see FIG. 3F); (iii) Affinity for C3b immobilised on a sensor chip as measured by SPR (A new map of glycosaminoglycan and C3b-binding sites on factor H. Schmidt C Q, Herbert A P, Kavanagh D, Gandy C, Fenton C J, Blaum B S, Lyon M, Uhrin D, Barlow P N. *J Immunol.* 2008 181:2610-9)(see FIG. 3G; (iv) Affinity for GAGs as measured by heparin-affinity chromatography or gel-mobility shift assay (Disease-associated sequence variations congregate in a polyanion recognition patch on human factor H revealed in three-dimensional structure. Herbert A P, Uhrin D, Lyon M, Pangburn M K, Barlow P N. *J Biol Chem.* 2006 281:16512-20); (v) Ability to protect sheep erythrocytes from complement-mediated haemolysis by FH-depleted human sera (available from Complement Technology)—a standard biological assay for human FH (Critical role of the C-terminal domains of factor H in regulating complement activation at cell surfaces. Ferreira V P, Herbert A P, Hocking H G, Barlow P N, Pangburn M K. *J Immunol.* 2006 177:6308-16)(see FIG. 3J); (vi) Ability to protect human cells from complement-mediated injury (Role of membrane cofactor protein (CD46) in regulation of C4b and C3b deposited on cells. Barilla-LaBarca M K, Liszewski M K, Lambris J D, Hourcade D, Atkinson J P. *J Immunol.* 2002 168:6298-304; Inhibiting complement activation on cells at the step of C3 cleavage. Liszewski M K, Fang C J, Atkinson J P. *Vaccine.* 2008, 26 Suppl 8:122-7__

In construct number 4 two amber codons have been incorporated and the protein product is suitable for site-specific placement of a pair of conjugates. With this construct it will be possible to explore the feasibility of introducing a second PEGylation site although it is expected that there may be a decrease in yield that generally accompanies each unnatural amino acid-residue incorporation. In this example, we have chosen conjugation sites on adjacent modules (modules 12 and 13) in the middle of the protein. Not only could these sites by PEGylated without compromising binding sites lying elsewhere in the FH molecule, they could be used for attachment of fluorescent probes resulting in fluorescent versions of human FH with potential applications in fluorescent microscopy and histology as well as diagnostics. Alternatively these sites could be used for conjugation with paramagnetic moieties that can be exploited in electron paramagnetic resonance spectroscopy to provide distance measurements between probes and, by inference, structural information that will help to generate hypotheses and the design of protein engineering approaches aimed at optimising FH efficacy.

Vectors 4 and 5 incorporate DNA encoding the yeast alpha-factor secretion signal peptide since it is potentially advantageous to explore secretion pathways other then the pathway that deals with the natural human FH secretion signal peptide. Vector 4 incorporates the codons for $NH_2$-Glu-Ala, while vector 5 does not, thereby providing opportunities to examine the role of the Glu-Ala spacer in terms of efficiency of proteolytic processing of the secretion signal peptide.

Vector 6 (utilising the alpha-factor/no-EA strategy) incorporates a construct encoding an example of a FH deletion. This term refers to versions of FH that are missing one or more central domains (or modules) within the region that connects together the two main C3b and GAG-binding sites proximal to the N and C termini. Such deletions represent an opportunity to create more compact version of hFH for research and therapeutic applications. In the current example (vector 6) modules 10-15 are deleted (for result, see FIG. 6). It will be appreciated that given the modularity of the FH structure it is possible to delete any number or combinations of modules (or to truncate FH at either end to create FH truncations). It is also facile to replace any of these deleted domains with homologous or non-homologous domains from other proteins. Vector 11 has been designed for production of an example of a FH mutant that can readily be produced in useful amounts using our strategy. In this example, nine basic amino acid residues have been replaced with Gln (neutral) residues. The basic amino acids selected in this case form a striking electropositive patch on module 13 of human FH (The central portion of factor H (modules 10-15) is compact and contains a structurally deviant CCP module. Schmidt C Q, Herbert A P, Mertens H D, Guariento M, Soares D C, Uhrin D, Rowe A J, Svergun D I, Barlow P N. *J Mol Biol.* 2009 Epub. October 14.) which seems unlikely to have evolved by chance and may have an as yet unrecognised binding role in the biological mechanism of action of FH. Thus we exploit our protein production strategy both to make therapeutic proteins and to make versions of FH for assay that shed light on structure-function relationships and hence on engineering of designer versions of FH with superior therapeutic efficacy.

The subset of vectors numbered 7 through 10 were designed for production of mouse FH (mFH) in *P. pastoris* using codon-optimised DNA. These protein products assist in the assessment of FH as a biotherapeutic in mouse-based models of disease. The natural mFH secretion signal sequence is exploited in vectors 7, 9 and 10 while vector 8 contains DNA for the yeast alpha-factor secretion signal (no Glu-Ala). Construct 7 encodes wild-type mFH and constructs 8 and 9 encode the mouse equivalents of the allQ- and unN- (i.e. amber) versions of human FH (i.e. as in the human versions, one or two of the N-glycosylation sites of mFH are re-engineered as sites of site-specific conjugation) (allQ-mFH and unN-mFH). PEGylated (or polysialylated proteins) are constructed as described for hFH. Construct 10 encodes a two-amber-codon version of mFH in which the remaining glycosylation sites (except those in modules 1-4 and 19-20) have been substituted, Asn to Gln.

To evaluate clinical potential of the protein products of vectors 1-11, we begin with the products of vectors 7-10 and test these in (i) the FH-knockout mouse ($FH^{-/-}$) that has uncontrolled plasma C3 activation and develops DDD (Uncontrolled C3 activation causes membranoproliferative glomerulonephritis in mice deficient in complement factor H. Pickering M C, Cook H T, Warren J, Bygrave A E, Moss J, Walport M J, Botto M. *Nat Genet* 2002 31:424-8) and retinal abnormalities (Complement factor H deficiency in aged mice causes retinal abnormalities and visual dysfunction. Coffey P J, Gias C, McDermott C J, Lundh P, Pickering M C, Sethi C, Bird A, Fitzke F W, Maass A, Chen L L, Holder G E, Luthert P J, Salt T E, Moss S E, Greenwood J. *Proc Natl Acad Sci USA.* 2007 104:16651-6), and (ii) the FH transgenic mouse (CFH-/-delta16-20 (in which, effectively, the truncated FH consisting of modules 1-15 replaces full-length FH) that develops aHUS (Spontaneous hemolytic uremic syndrome triggered by complement factor H lacking surface recognition domains. Pickering M C, de Jorge E G, Martinez-Barricarte R, Recalde S, Garcia-Layana A, Rose K L, Moss J, Walport M J, Cook H T, de Córdoba S R, Botto M. *J Exp Med* 2007 204:1249-56.). We select the best candidate(s) based on a range of considerations including yield of protein, bioassays and standard toxicology studies. For example, allQ-mFH, PEG-mFH and/or $PEG^x$-mFH (likely to have low immunogenicity) will be injected i.v./i.p. into the $FH^{-/--}$ mouse. Levels of complement components C3, factor B and naturally expressed mouse FH (as well as the recombinant mFH) are measured by ELISA to titrate optimal doses of mFH needed to achieve maximal complement regulation in the serum and to assess mFH half-lives. With the dosing schedule optimised we evaluate the efficacy of mFH against DDD and retinal abnormalities. Survival, renal function (urinary albumin, serum urea) and retinal abnormalities (behavioural and electrophysiological studies) of the $FH^{-/-}$ mice over a period of eight months (kidney)/24 months (retina) will be assessed and compared to untreated $FH^{-/-}$ mice. Histological studies (light microscopy, immunofluoresence and fluorescent and electron microscopy) are used to assess differences in glomerular and retinal pathology in the two groups. Any generation of antibodies against mFH in these FH-deficient mice is assessed by ELISA-based assays. The utility of our product(s) in aHUS is determined in analogous experiments in the $CFH^{-/-}$ delta 16-20 mouse.

We are continuing to improve the yields of hFH by further DNA manipulation and optimisation of fermentation technology, aiming to achieve production levels in the region of grams of protein per 10-liter fermentation. In the literature on *P. pastoris*, expression levels of 100-500 mg or more protein per liter have been reported. Numerous strategies available for the improvement of yield include: further enhancements of DNA sequence to decrease RNA secondary structure; elimination of potential proteolytic sites where possible; wider screening and selection for high copy-number transformants arising from multiple integration events; choice of culture conditions e.g. agitation, oxygen supply, pH, temperature, and addition of reagents (e.g. EDTA, amine salts, casamino acids) to minimize proteolysis; timing and rates of glycerol/methanol feeds (reviewed in for example Expression of recombinant proteins in *Pichia pastoris*. Li P, Anumanthan A, Gao X G, Ilangovan K, Suzara V V, Duzgune N, Renugopalakrishnan *V. Appl Biochem Biotechnol.* 2007 142:105-24).

The invention claimed is:

1. A nucleic acid encoding a mammalian factor H (FH) polypeptide, wherein the nucleic acid comprises the nucleic acid sequence of SEQ ID NO: 2, wherein the polypeptide is capable of binding C3b.

2. The nucleic acid of claim 1, wherein the nucleic acid is in a vector.

3. The nucleic acid of claim 1, wherein the nucleic acid is operatively linked to a promoter.

* * * * *

SEQUENCE LISTING

```
<160> NUMBER OF SEQ ID NOS: 13

<210> SEQ ID NO 1
<211> LENGTH: 3642
<212> TYPE: DNA
<213> ORGANISM: Homo sapiens

<400> SEQUENCE: 1

ggagattgca atgaacttcc tccaagaaga aatacagaaa ttctgacagg ttcctggtct     60

gaccaaacat atccagaagg cacccaggct atctataaat gccgccctgg atatagatct    120

cttggaaatg taataatggt atgcaggaag ggagaatggg ttgctcttaa tccattaagg    180

aaatgtcaga aaaggccctg tggacatcct ggagatactc cttttggtac ttttaccctt    240

acaggaggaa atgtgtttga atatggtgta aaagctgtgt atacatgtaa tgaggggtat    300

caattgctag gtgagattaa ttaccgtgaa tgtgacacag atggatggac caatgatatt    360

cctatatgtg aagttgtgaa gtgtttacca gtgacagcac cagagaatgg aaaaattgtc    420

agtagtgcaa tggaaccaga tcgggaatac cattttggac aagcagtacg gtttgtatgt    480

aactcaggct acaagattga aggagatgaa gaaatgcatt gttcagacga tggtttttgg    540

agtaaagaga aaccaaagtg tgtggaaatt tcatgcaaat ccccagatgt tataaatgga    600

tctcctatat ctcagaagat tatttataag gagaatgaac gatttcaata taaatgtaac    660

atgggttatg aatacagtga aagaggagat gctgtatgca ctgaatctgg atggcgtccg    720

ttgccttcat gtgaagaaaa atcatgtgat aatccttata ttccaaatgg tgactactca    780

cctttaagga ttaaacacag aactggagat gaaatcacgt accagtgtag aaatggtttt    840

tatcctgcaa cccggggaaa tacagccaaa tgcacaagta ctggctggat acctgctccg    900

agatgtacct tgaaaccttg tgattatcca gacattaaac atggaggtct atatcatgag    960

aatatgcgta gaccatactt tccagtagct gtaggaaaat attactccta ttactgtgat   1020

gaacactttg agactccgtc aggaagttac tgggatcaca ttcattgcac acaagatgga   1080

tggtcgccag cagtaccatg cctcagaaaa tgttattttc cttatttgga aaatggatat   1140

aatcaaaatt atggaagaaa gtttgtacag ggtaaatcta tagacgttgc ctgccatcct   1200

ggctacgctc ttccaaaagc gcagaccaca gttacatgta tggagaatgg ctggtctcct   1260

actcccagat gcatccgtgt caaaacatgt tccaaatcaa gtatagatat tgagaatggg   1320

tttatttctg aatctcagta tacatatgcc ttaaaagaaa aagcgaaata tcaatgcaaa   1380

ctaggatatg taacagcaga tggtgaaaca tcaggatcaa ttacatgtgg gaaagatgga   1440
```

-continued

```
tggtcagctc aacccacgtg cattaaatct tgtgatatcc cagtatttat gaatgccaga   1500

actaaaaatg acttcacatg gtttaagctg aatgacacat tggactatga atgccatgat   1560

ggttatgaaa gcaatactgg aagcaccact ggttccatag tgtgtggtta caatggttgg   1620

tctgatttac ccatatgtta tgaaagagaa tgcgaacttc ctaaaataga tgtacactta   1680

gttcctgatc gcaagaaaga ccagtataaa gttggagagg tgttgaaatt ctcctgcaaa   1740

ccaggattta caatagttgg acctaattcc gttcagtgct accactttgg attgtctcct   1800

gacctcccaa tatgtaaaga gcaagtacaa tcatgtggtc cacctcctga actcctcaat   1860

gggaatgtta aggaaaaaac gaaagaagaa tatggacaca gtgaagtggt ggaatattat   1920

tgcaatcctg gatttctaat gaagggacct aataaaattc aatgtgttga tggagagtgg   1980

acaactttac cagtgtgtat tgtggaggag agtacctgtg gagatatacc tgaacttgaa   2040

catggctggg cccagctttc ttcccctcct tattactatg gagattcagt ggaattcaat   2100

tgctcagaat catttacaat gattggacac agatcaatta cgtgtattca tggagtatgg   2160

acccaacttc cccagtgtgt ggcaatagat aaacttaaga agtgcaaatc atcaaattta   2220

attatacttg aggaacattt aaaaaacaag aaggaattcg atcataattc taacataagg   2280

tacagatgta gaggaaaaga aggatggata cacacagtct gcataaatgg aagatgggat   2340

ccagaagtga actgctcaat ggcacaaata caattatgcc cacctccacc tcagattccc   2400

aattctcaca atatgacaac cacactgaat tatcgggatg gagaaaaagt atctgttctt   2460

tgccaagaaa attatctaat tcaggaagga gaagaaatta catgcaaaga tggaagatgg   2520

cagtcaatac cactctgtgt tgaaaaaatt ccatgttcac aaccacctca gatagaacac   2580

ggaaccatta attcatccag gtcttcacaa gaaagttatg cacatgggac taaattgagt   2640

tatacttgtg agggtggttt caggatatct gaagaaaatg aaacaacatg ctacatggga   2700

aaatggagtt ctccacctca gtgtgaaggc cttccttgta aatctccacc tgagatttct   2760

catggtgttg tagctcacat gtcagacagt tatcagtatg gagaagaagt tacgtacaaa   2820

tgttttgaag gttttggaat tgatgggcct gcaattgcaa aatgcttagg agaaaaatgg   2880

tctcaccctc catcatgcat aaaaacagat tgtctcagtt tacctagctt tgaaaatgcc   2940

atacccatgg gagagaagaa ggatgtgtat aaggcgggtg agcaagtgac ttacacttgt   3000

gcaacatatt acaaaatgga tggagccagt aatgtaacat gcattaatag cagatggaca   3060

ggaaggccaa catgcagaga cacctcctgt gtgaatccgc ccacagtaca aaatgcttat   3120

atagtgtcga gacagatgag taaatatcca tctggtgaga gagtacgtta tcaatgtagg   3180

agcccttatg aaatgtttgg ggatgaagaa gtgatgtgtt taaatggaaa ctggacggaa   3240

ccacctcaat gcaaagattc tacaggaaaa tgtgggcccc ctccacctat tgacaatggg   3300

gacattactt cattcccgtt gtcagtatat gctccagctt catcagttga gtaccaatgc   3360

cagaacttgt atcaacttga gggtaacaag cgaataacat gtagaaatgg acaatggtca   3420

gaaccaccaa aatgcttaca tccgtgtgta atatcccgag aaattatgga aaattataac   3480

atagcattaa ggtggacagc caaacagaag ctttattcga gaacaggtga atcagttgaa   3540

tttgtgtgta aacggggata tcgtctttca tcacgttctc acacattgcg aacaacatgt   3600

tgggatggga aactggagta tccaacttgt gcaaaaagat ag                      3642
```

<210> SEQ ID NO 2
<211> LENGTH: 3645
<212> TYPE: DNA

-continued

```
<213> ORGANISM: Artificial
<220> FEATURE:
<223> OTHER INFORMATION: Codon Optimised sequence for P. pastoris
      expression of human factor H

<400> SEQUENCE: 2

gaggattgta acgagttgcc accaagaaga aacactgaga tcttgactgg ttcttggagt     60

gatcaaactt acccagaggg tactcaggct atctacaagt gtagaccagg ttacagatcc    120

ttgggtaacg ttatcatggt ttgtagaaag ggtgagtggg ttgcattgaa cccattgaga    180

aagtgtcaga aaagaccatg tggtcaccca ggtgatactc cattcggtac tttcactttg    240

actggtggta acgttttcga gtacggtgtt aaggctgttt acacttgtaa cgagggttac    300

cagttgttgg gagagatcaa ctacagagag tgtgatactg acggatggac taacgacatt    360

ccaatctgtg aagttgttaa gtgtttgcca gttactgctc cagagaacgg aaagattgtt    420

tcctccgcta tggaaccaga tagagagtac cacttcggac aggctgttag attcgtttgt    480

aactccggtt acaagattga aggtgacgaa gagatgcact gttctgatga cggtttctgg    540

tccaaagaaa agccaaagtg tgttgagatc tcctgtaagt ccccagacgt tattaacggt    600

tccccaatct cccaaaagat catctacaaa gagaacgaga gattccagta caagtgtaac    660

atgggttacg agtactctga aagaggtgac gctgtttgta ctgaatctgg atggagacca    720

ttgccatcct gtgaagagaa gtcctgtgac aacccataca ttccaaacgg tgactactcc    780

ccattgagaa tcaagcacag aactggtgac gagatcactt accagtgtag aaatggtttc    840

tacccagcta ctagaggtaa cactgctaag tgtacttcca ctggatggat tccagctcca    900

agatgtactt tgaagccatg tgactaccca gatatcaagc acggtggttt gtaccacgag    960

aacatgagaa ggccatactt cccagttgct gttggaaagt actactccta ctactgtgac   1020

gaacacttcg aaactccatc tggttcttac tgggaccaca tccactgtac tcaagatggt   1080

tggtccccag ctgttccatg tttgagaaaa tgttacttcc catacttgga gaacggttac   1140

aaccagaact acggtagaaa gttcgttcag ggaaagtcca ttgacgttgc ttgtcatcca   1200

ggttacgctt tgccaaaggc tcagactact gttacttgta tggaaaacgg ttggtcccct   1260

actcctagat gtatcagagt taagacttgt tccaagtcct ccatcgacat tgagaacggt   1320

ttcatttccg agtcccagta cacttacgct ttgaaagaga aggctaagta ccagtgtaaa   1380

ttgggatacg ttactgctga cggtgaaact tccggatcaa tcacatgtgg aaaagacgga   1440

tggagtgctc aaccaacttg tatcaagtct tgtgacatcc cagttttcat gaacgctaga   1500

actaagaacg acttcacatg gttcaagttg aacgacactt tggactacga atgtcacgac   1560

ggttacgaat ctaacactgg ttccactact ggttccatcg tttgtggtta caatggatgg   1620

agtgacttgc caatctgtta cgagagagag tgcgagttgc caaagatcga cgttcatttg   1680

gttccagaca gaaagaagga ccagtacaaa gttggagagg ttttgaagtt ctcctgtaag   1740

ccaggtttca ctatcgttgg tccaaactcc gttcagtgtt accacttcgg tttgtctcca   1800

gacttgccta tctgtaaaga gcaggttcaa tcctgcggac caccaccaga attgttgaac   1860

ggtaacgtta aagaaaagac taaagaagag tacggtcact ccgaagttgt tgagtactac   1920

tgtaacccaa gattcttgat gaagggtcca aacaagatcc aatgtgttga cggtgagtgg   1980

actactttgc cagtttgtat cgttgaagag tccacttgtg gtgacattcc agaattggaa   2040

cacggatggg ctcaattgtc atccccacca tactactacg gtgactccgt tgaattcaac   2100

tgttccgagt ccttcactat gattggtcac agatccatca catgtatcca cggtgtttgg   2160
```

-continued

```
actcaattgc cacagtgtgt tgctatcgac aagttgaaga agtgtaaatc atccaacctt   2220
atcatcttgg aggaacactt gaagaacaag aaagagttcg accacaactc caacatcaga   2280
tacagatgta gaggtaaaga gggatggatc cacactgttt gtatcaacgg tagatgggac   2340
cctgaagtta actgttccat ggctcagatt cagttgtgtc caccaccacc acaaattcca   2400
aactcccaca acatgactac tactttgaac tacagagatg gtgaaaaggt ttccgttttg   2460
tgtcaagaga actacttgat ccaagagggt gaagagatca catgtaagga cggtagatgg   2520
cagtccatcc ctttgtgtgt tgagaagatc ccatgttccc aaccacctca aattgagcac   2580
ggtactatca actcttccag atcctctcaa gagtcttacg ctcacggtac taagttgtcc   2640
tacacttgtg agggaggttt cagaatctct gaggaaaacg agactacttg ttacatggga   2700
aagtggtcat ctccaccaca atgtgaagga ttgccttgta agtctccacc agagatttct   2760
cacggtgttg ttgctcacat gtccgactct taccaatacg gagaagaggt tacctacaag   2820
tgtttcgagg gtttcggtat tgatggtcca gctatcgcta agtgtttggg agaaaagtgg   2880
tcccatcctc catcctgtat caagactgat tgtttgtcct tgccatcctt cgaaaacgct   2940
atcccaatgg gagaaaagaa ggacgtttac aaggctggtg aacaagttac ttatacttgt   3000
gctacttact acaagatgga cggtgcttcc aacgttactt gtatcaactc cagatggact   3060
ggtagaccaa cttgtagaga cacttcctgt gttaacccac caactgttca gaacgcttac   3120
atcgtttcca gacagatgtc taagtaccca tccggagaac gtgttagata ccaatgtaga   3180
tccccatacg agatgttcgg tgacgaagag gttatgtgtt tgaacggtaa ttggactgaa   3240
ccaccacagt gtaaggactc cactggtaag tgtggtccac ctccaccaat tgacaacggt   3300
gacatcactt ctttcccttt gtccgtttac gctccagctt cttccgttga gtaccagtgt   3360
cagaacttgt accagttgga gggtaacaag agaatcactt gtagaaacgg acaatggagt   3420
gagccaccaa agtgtttgca cccatgtgtt atctccagag aaatcatgga aaactacaac   3480
attgctttga gatggactgc taaacagaag ttgtactcca gaactggtga atccgttgag   3540
ttcgtttgta agagaggtta cagattgtcc tccagatccc acactttgag aactacatgt   3600
tgggacggaa aattggagta cccaacttgt gctaagagat agtag                   3645
```

<210> SEQ ID NO 3
<211> LENGTH: 3733
<212> TYPE: DNA
<213> ORGANISM: Artificial
<220> FEATURE:
<223> OTHER INFORMATION: Codon optimised human hactor H variant

<400> SEQUENCE: 3

```
ggcgcgccgg atccaaaaat gagattgttg gctaagatca tctgtttgat gttgtgggct     60
atctgtgttg ctgaggactg taacgaattg ccaccgcgga gaaacactga gattttgact    120
ggttcctggt ccgatcaaac ttacccagag ggtactcagg ctatctacaa gtgtagacca    180
ggttacagat ccttgggtaa catcatcatg gtttgtagaa agggtgagtg ggttgctttg    240
aacccattga gaaagtgtca gaaaagacca tgtggtcacc caggtgatac tccattcggt    300
actttcactt tgactggtgg taacgttttc gagtacggtg ttaaggctgt ttacacttgt    360
aacgagggtt accagttgtt gggtgagatc aactacagag agtgtgatac tgacggttgg    420
actaacgaca ttccaatctg tgaggttgtt aagtgtttgc cagttactgc tccagagaac    480
ggtaagattg tttcctccgc tatggaacca gatagagagt accacttcgg tcaggctgtt    540
agattcgttt gtaactccgg ttacaagatt gaaggtgacg aagagatgca ctgttctgat    600
```

-continued

```
gacggtttct ggtccaaaga aaagccaaag tgtgttgaga tttcctgtaa gtccccagac    660
gttattaacg gttccccaat ctcccaaaag atcatctaca aagagaacga gagattccag    720
tacaagtgta acatgggtta cgagtactct gaaagaggtg acgctgtttg tactgaatct    780
ggttggagac cattgccatc ctgtgaagag aagtcctgtg acaacccata cattccaaac    840
ggtgactact ccccattgag aatcaagcac agaactggtg acgagatcac ttaccagtgt    900
agaaacggtt tctacccagc tactagaggt aacactgcta agtgtacttc cactggttgg    960
attccagctc caagatgtac tttgaagcca tgtgactacc cagatatcaa gcacggtggt   1020
ttgtaccacg agaacatgag aagaccatac ttcccagttg ctgttggaaa gtactactcc   1080
tactactgtg acgaacactt cgaaactcca tctggttctt actgggacca catccactgt   1140
actcaagatg gttggtcccc agctgttcca tgtttgagaa aatgttactt cccatacttg   1200
gagaacggtt acaaccagaa ctacggtaga aagttcgttc agggaaagtc cattgacgtt   1260
gcttgtcatc caggttacgc tttgccaaag gctcagacta ctgttacttg tatggaaaac   1320
ggttggtccc ctactcctag atgtatcaga gttaagactt gttccaagtc ctccatcgac   1380
attgagaacg gtttcatttc cgagtcccag tacacttacg ctttgaaaga gaaggctaag   1440
taccagtgta aattgggata cgttactgct gacggtgaaa cttccggttc catcacttgt   1500
ggtaaggatg gttggtctgc tcaaccaact tgtatcaagt cttgtgacat cccagttttc   1560
atgaacgcta gaactaagaa cgacttcaca tggttcaagt tgaacgacac tttggactac   1620
gaatgtcacg acggttacga atctaacact ggttccacta ctggttccat cgtttgtggt   1680
tacaacggtt ggtctgactt gccaatctgt tacgagagag agtgcgagtt gccaaagatc   1740
gacgttcatt tggttccaga cagaaagaag gaccagtaca aggttggtga ggttttgaag   1800
ttctcctgta agccaggttt cactatcgtt ggtccaaact ccgttcagtg ttaccatttc   1860
ggtttgtccc cagacttgcc tatttgtaaa gagcaggttc agtcttgcgg tccaccacca   1920
gaattgttga acggtaacgt taaagaaaag actaaagaag agtacggtca ctctgaggtt   1980
gttgagtact actgtaaccc aagattcttg atgaagggtc caaacaagat ccaatgtgtt   2040
gacggtgagt ggactacttt gccagtttgt atcgttgaag agtccacttg tggtgacatt   2100
ccagaattgg aacacggttg ggctcaattg tcatccccac catactacta cggtgactcc   2160
gttgagttca actgttccga gtccttcact atgattggtc acagatccat cacatgtatc   2220
cacggtgttt ggactcaatt gccacagtgt gttgctatcg acaagttgaa gaagtgtaaa   2280
tcctccaact tgatcatctt ggaggaacac ttgaagaaca agaaagagtt cgaccacaac   2340
tccaacatca gatacagatg tagaggtaaa gagggttgga ttcacactgt ttgtatcaac   2400
ggtagatggg accctgaagt taactgttcc atggctcaga ttcagttgtg tccaccacct   2460
ccacaaattc caaactccca caacatgact actactttga actacagaga tggtgagaag   2520
gtttccgttt tgtgtcaaga gaactacttg atccaagagg gtgaggaaat cacttgtaag   2580
gacggtagat ggcaatccat cccattgtgt gttgagaaga tcccatgttc ccaaccacca   2640
caaattgagc acggtactat caactcttcc agatcctctc aagagtctta cgctcacggt   2700
actaagttgt cctacacttg tgagggtggt ttcagaatct ctgaggaaaa cgagactact   2760
tgttacatgg gaaagtggtc ctctccacca caatgtgaag gtttgccttg taagtctcca   2820
ccagagattt ctcacggtgt tgttgctcac atgtccgact cttaccaata cggtgaagag   2880
gttacttaca agtgtttcga gggtttcggt attgatggtc cagctatcgc taagtgtttg   2940
```

-continued

```
ggtgaaaagt ggtcccatcc tccatcctgt atcaagactg actgtttgtc cttgccatct   3000

ttcgagaacg ctatcccaat gggtgaaaag aaggacgttt acaaggctgg tgaacaggtt   3060

acatacactt gtgctactta ctacaagatg gacggtgctt ccaacgttac ttgtatcaac   3120

tccagatgga ctggtagacc aacttgtaga gacacttcct gtgttaaccc accaactgtt   3180

cagaacgctt acatcgtttc cagacagatg tctaagtacc catccggtga gagagttaga   3240

taccaatgta gatccccata cgagatgttc ggtgacgaag aggttatgtg tttgaacggt   3300

aattggactg aaccaccaca gtgtaaggac tccactggta agtgtggtcc acctccacca   3360

attgacaacg gtgacatcac ttctttccca ttgtccgttt acgctccagc ttcttccgtt   3420

gagtaccagt gtcagaactt gtaccagttg gagggtaaca agagaatcac ttgtagaaac   3480

ggacaatggt ctgagccacc aaagtgtttg cacccatgtg ttatctccag agaaatcatg   3540

gaaaactaca acattgcttt gagatggact gctaagcaga agttgtactc cagaacaggt   3600

gagtctgttg agtttgtttg taagagaggt tacagattgt cctccagatc ccacactttg   3660

agaactacat gttgggacgg aaagttggag tacccaactt gtgctaagag ataatgagcg   3720

gccgcttaat taa                                                      3733
```

<210> SEQ ID NO 4
<211> LENGTH: 3733
<212> TYPE: DNA
<213> ORGANISM: Artificial
<220> FEATURE:
<223> OTHER INFORMATION: Codon optimised human hactor H variant

<400> SEQUENCE: 4

```
ggcgcgccgg atccaaaaat gagattgttg gctaagatca tctgtttgat gttgtgggct     60

atctgtgttg ctgaggactg taacgaattg ccaccgcgga gaaacactga gattttgact    120

ggttcctggt ccgatcaaac ttacccagag ggtactcagg ctatctacaa gtgtagacca    180

ggttacagat ccttgggtaa catcatcatg gtttgtagaa agggtgagtg ggttgctttg    240

aacccattga gaaagtgtca gaaaagacca tgtggtcacc caggtgatac tccattcggt    300

actttcactt tgactggtgg taacgttttc gagtacggtg ttaaggctgt ttacacttgt    360

aacgagggtt accagttgtt gggtgagatc aactacagag agtgtgatac tgacggttgg    420

actaacgaca ttccaatctg tgaggttgtt aagtgtttgc cagttactgc tccagagaac    480

ggtaagattg tttcctccgc tatggaacca gatagagagt accacttcgg tcaggctgtt    540

agattcgttt gtaactccgg ttacaagatt gaaggtgacg aagagatgca ctgttctgat    600

gacggtttct ggtccaaaga aaagccaaag tgtgttgaga tttcctgtaa gtccccagac    660

gttattaacg gttccccaat ctcccaaaag atcatctaca aagagaacga gagattccag    720

tacaagtgta acatgggtta cgagtactct gaaagaggtg acgctgtttg tactgaatct    780

ggttggagac cattgccatc ctgtgaagag aagtcctgtg acaacccata cattccaaac    840

ggtgactact ccccattgag aatcaagcac agaactggtg acgagatcac ttaccagtgt    900

agaaacggtt tctacccagc tactagaggt aacactgcta agtgtacttc cactggttgg    960

attccagctc caagatgtac tttgaagcca tgtgactacc cagatatcaa gcacggtggt   1020

ttgtaccacg agaacatgag aagaccatac ttcccagttg ctgttggaaa gtactactcc   1080

tactactgtg acgaacactt cgaaactcca tctggttctt actgggacca catccactgt   1140

actcaagatg gttggtcccc agctgttcca tgtttgagaa aatgttactt cccatacttg   1200

gagaacggtt acaaccagaa ctacggtaga aagttcgttc agggaaagtc cattgacgtt   1260
```

-continued

```
gcttgtcatc caggttacgc tttgccaaag gctcagacta ctgttacttg tatggaaaac   1320
ggttggtccc ctactcctag atgtatcaga gttaagactt gttccaagtc ctccatcgac   1380
attgagaacg gtttcatttc cgagtcccag tacacttacg ctttgaaaga gaaggctaag   1440
taccagtgta aattgggata cgttactgct gacggtgaaa cttccggttc catcacttgt   1500
ggtaaggatg gttggtctgc tcaaccaact tgtatcaagt cttgtgacat cccagttttc   1560
atgaacgcta gaactaagaa cgacttcaca tggttcaagt tgcaagacac tttggactac   1620
gaatgtcacg acggttacga atctaacact ggttccacta ctggttccat cgtttgtggt   1680
tacaacggtt ggtctgactt gccaatctgt tacgagagag agtgcgagtt gccaaagatc   1740
gacgttcatt tggttccaga cagaaagaag gaccagtaca aggttggtga ggttttgaag   1800
ttctcctgta agccaggttt cactatcgtt ggtccaaact ccgttcagtg ttaccatttc   1860
ggtttgtccc cagacttgcc tatttgtaaa gagcaggttc agtcttgcgg tccaccacca   1920
gaattgttga acggtaacgt taaagaaaag actaaagaag agtacggtca ctctgaggtt   1980
gttgagtact actgtaaccc aagattcttg atgaagggtc caaacaagat ccaatgtgtt   2040
gacggtgagt ggactacttt gccagtttgt atcgttgaag agtccacttg tggtgacatt   2100
ccagaattgg aacacggttg ggctcaattg tcatccccac catactacta cggtgactcc   2160
gttgagttcc aatgttccga gtccttcact atgattggtc acagatccat cacatgtatc   2220
cacggtgttt ggactcaatt gccacagtgt gttgctatcg acaagttgaa gaagtgtaaa   2280
tcctccaact tgatcatctt ggaggaacac ttgaagaaca agaaagagtt cgaccacaac   2340
tccaacatca gatacagatg tagaggtaaa gagggttgga ttcacactgt ttgtatcaac   2400
ggtagatggg accctgaagt tcaatgttcc atggctcaga ttcagttgtg tccaccacct   2460
ccacaaattc caaactccca ccaaatgact actactttga actacagaga tggtgagaag   2520
gtttccgttt tgtgtcaaga gaactacttg atccaagagg gtgaggaaat cacttgtaag   2580
gacggtagat ggcaatccat cccattgtgt gttgagaaga tcccatgttc ccaaccacca   2640
caaattgagc acggtactat ccaatcttcc agatcctctc aagagtctta cgctcacggt   2700
actaagttgt cctacacttg tgagggtggt ttcagaatct ctgaggaaca agagactact   2760
tgttacatgg gaaagtggtc ctctccacca caatgtgaag gtttgccttg taagtctcca   2820
ccagagattt ctcacggtgt tgttgctcac atgtccgact cttaccaata cggtgaagag   2880
gttacttaca agtgtttcga gggtttcggt attgatggtc cagctatcgc taagtgtttg   2940
ggtgaaaagt ggtcccatcc tccatcctgt atcaagactg actgtttgtc cttgccatct   3000
ttcgagaacg ctatcccaat gggtgaaaag aaggacgttt acaaggctgg tgaacaggtt   3060
acatacactt gtgctactta ctacaagatg gacggtgctt cccaagttac ttgtatcaac   3120
tccagatgga ctggtagacc aacttgtaga gacacttcct gtgttaaccc accaactgtt   3180
cagaacgctt acatcgtttc cagacagatg tctaagtacc catccggtga gagagttaga   3240
taccaatgta gatccccata cgagatgttc ggtgacgaag aggttatgtg tttgaacggt   3300
caatggactg aaccaccaca gtgtaaggac tccactggta agtgtggtcc acctccacca   3360
attgacaacg gtgacatcac ttctttccca ttgtccgttt acgctccagc ttcttccgtt   3420
gagtaccagt gtcagaactt gtaccagttg gagggtaaca agagaatcac ttgtagaaac   3480
ggacaatggt ctgagccacc aaagtgtttg cacccatgtg ttatctccag agaaatcatg   3540
gaaaactaca acattgcttt gagatggact gctaagcaga agttgtactc cagaacaggt   3600
```

```
gagtctgttg agtttgtttg taagagaggt tacagattgt cctccagatc ccacactttg   3660

agaactacat gttgggacgg aaagttggag tacccaactt gtgctaagag ataatgagcg   3720

gccgcttaat taa                                                      3733
```

<210> SEQ ID NO 5
<211> LENGTH: 3733
<212> TYPE: DNA
<213> ORGANISM: Artificial
<220> FEATURE:
<223> OTHER INFORMATION: Codon optimised human hactor H variant

<400> SEQUENCE: 5

```
ggcgcgccgg atccaaaaat gagattgttg gctaagatca tctgtttgat gttgtgggct     60

atctgtgttg ctgaggactg taacgaattg ccaccgcgga gaaacactga gattttgact    120

ggttcctggt ccgatcaaac ttacccagag ggtactcagg ctatctacaa gtgtagacca    180

ggttacagat ccttgggtaa catcatcatg gtttgtagaa agggtgagtg ggttgctttg    240

aacccattga gaaagtgtca gaaaagacca tgtggtcacc caggtgatac tccattcggt    300

actttcactt tgactggtgg taacgttttc gagtacggtg ttaaggctgt ttacacttgt    360

aacgagggtt accagttgtt gggtgagatc aactacagag agtgtgatac tgacggttgg    420

actaacgaca ttccaatctg tgaggttgtt aagtgtttgc cagttactgc tccagagaac    480

ggtaagattg tttcctccgc tatggaacca gatagagagt accacttcgg tcaggctgtt    540

agattcgttt gtaactccgg ttacaagatt gaaggtgacg aagagatgca ctgttctgat    600

gacggtttct ggtccaaaga aaagccaaag tgtgttgaga tttcctgtaa gtccccagac    660

gttattaacg gttccccaat ctcccaaaag atcatctaca aagagaacga gagattccag    720

tacaagtgta acatgggtta cgagtactct gaaagaggtg acgctgtttg tactgaatct    780

ggttggagac cattgccatc ctgtgaagag aagtcctgtg acaacccata cattccaaac    840

ggtgactact ccccattgag aatcaagcac agaactggtg acgagatcac ttaccagtgt    900

agaaacggtt tctacccagc tactagaggt aacactgcta agtgtacttc cactggttgg    960

attccagctc caagatgtac tttgaagcca tgtgactacc cagatatcaa gcacggtggt   1020

ttgtaccacg agaacatgag aagaccatac ttcccagttg ctgttggaaa gtactactcc   1080

tactactgtg acgaacactt cgaaactcca tctggttctt actgggacca catccactgt   1140

actcaagatg gttggtcccc agctgttcca tgtttgagaa aatgttactt cccatacttg   1200

gagaacggtt acaaccagaa ctacggtaga aagttcgttc agggaaagtc cattgacgtt   1260

gcttgtcatc caggttacgc tttgccaaag gctcagacta ctgttacttg tatggaaaac   1320

ggttggtccc ctactcctag atgtatcaga gttaagactt gttccaagtc ctccatcgac   1380

attgagaacg gtttcatttc cgagtcccag tacacttacg ctttgaaaga gaaggctaag   1440

taccagtgta aattgggata cgttactgct gacggtgaaa cttccggttc catcacttgt   1500

ggtaaggatg gttggtctgc tcaaccaact tgtatcaagt cttgtgacat cccagttttc   1560

atgaacgcta gaactaagaa cgacttcaca tggttcaagt tgcaagacac tttggactac   1620

gaatgtcacg acggttacga atctaacact ggttccacta ctggttccat cgtttgtggt   1680

tacaacggtt ggtctgactt gccaatctgt tacgagagag agtgcgagtt gccaaagatc   1740

gacgttcatt tggttccaga cagaaagaag gaccagtaca aggttggtga ggttttgaag   1800

ttctcctgta agccaggttt cactatcgtt ggtccaaact ccgttcagtg ttaccatttc   1860

ggtttgtccc cagacttgcc tatttgtaaa gagcaggttc agtcttgcgg tccaccacca   1920
```

```
gaattgttga acggtaacgt taaagaaaag actaaagaag agtacggtca ctctgaggtt   1980

gttgagtact actgtaaccc aagattcttg atgaagggtc caaacaagat ccaatgtgtt   2040

gacggtgagt ggactacttt gccagtttgt atcgttgaag agtccacttg tggtgacatt   2100

ccagaattgg aacacggttg ggctcaattg tcatccccac catactacta cggtgactcc   2160

gttgagttcc aatgttccga gtccttcact atgattggtc acagatccat cacatgtatc   2220

cacggtgttt ggactcaatt gccacagtgt gttgctatcg acaagttgaa gaagtgtaaa   2280

tcctccaact tgatcatctt ggaggaacac ttgaagaaca agaaagagtt cgaccacaac   2340

tccaacatca gatacagatg tagaggtaaa gagggttgga ttcacactgt ttgtatcaac   2400

ggtagatggg accctgaagt tcaatgttcc atggctcaga ttcagttgtg tccaccacct   2460

ccacaaattc caaactccca ccaaatgact actactttga actacagaga tggtgagaag   2520

gtttccgttt tgtgtcaaga gaactacttg atccaagagg gtgaggaaat cacttgtaag   2580

gacggtagat ggcaatccat cccattgtgt gttgagaaga tcccatgttc ccaaccacca   2640

caaattgagc acggtactat ccaatctagt agatcctctc aagagtctta cgctcacggt   2700

actaagttgt cctacacttg tgagggtggt ttcagaatct ctgaggaata ggagactact   2760

tgttacatgg gaaagtggtc ctctccacca caatgtgaag gtttgccttg taagtctcca   2820

ccagagattt ctcacggtgt tgttgctcac atgtccgact cttaccaata cggtgaagag   2880

gttacttaca agtgtttcga gggtttcggt attgatggtc cagctatcgc taagtgtttg   2940

ggtgaaaagt ggtcccatcc tccatcctgt atcaagactg actgtttgtc cttgccatct   3000

ttcgagaacg ctatcccaat gggtgaaaag aaggacgttt acaaggctgg tgaacaggtt   3060

acatacactt gtgctactta ctacaagatg gacggtgctt cccaagttac ttgtatcaac   3120

tccagatgga ctggtagacc aacttgtaga gacacttcct gtgttaaccc accaactgtt   3180

cagaacgctt acatcgtttc cagacagatg tctaagtacc catccggtga gagagttaga   3240

taccaatgta gatccccata cgagatgttc ggtgacgaag aggttatgtg tttgaacggt   3300

caatggactg aaccaccaca gtgtaaggac tccactggta agtgtggtcc acctccacca   3360

attgacaacg gtgacatcac ttctttccca ttgtccgttt acgctccagc ttcttccgtt   3420

gagtaccagt gtcagaactt gtaccagttg gagggtaaca agagaatcac ttgtagaaac   3480

ggacaatggt ctgagccacc aaagtgtttg cacccatgtg ttatctccag agaaatcatg   3540

gaaaactaca acattgcttt gagatggact gctaagcaga agttgtactc cagaacaggt   3600

gagtctgttg agtttgtttg taagagaggt tacagattgt cctccagatc ccacactttg   3660

agaactacat gttgggacgg aaagttggag tacccaactt gtgctaagag ataatgagcg   3720

gccgcttaat taa                                                      3733
```

<210> SEQ ID NO 6
<211> LENGTH: 3676
<212> TYPE: DNA
<213> ORGANISM: Artificial
<220> FEATURE:
<223> OTHER INFORMATION: Codon optimised human hactor H variant

<400> SEQUENCE: 6

```
ggcgcgcctg caggtgagga ctgtaacgaa ttgccaccgc ggagaaacac tgagattttg     60

actggttcct ggtccgatca aacttaccca gagggtactc aggctatcta caagtgtaga    120

ccaggttaca gatccttggg taacatcatc atggtttgta gaaagggtga gtgggttgct    180
```

-continued

```
ttgaacccat tgagaaagtg tcagaaaaga ccatgtggtc acccaggtga tactccattc    240
ggtactttca ctttgactgg tggtaacgtt ttcgagtacg gtgttaaggc tgtttacact    300
tgtaacgagg gttaccagtt gttgggtgag atcaactaca gagagtgtga tactgacggt    360
tggactaacg acattccaat ctgtgaggtt gttaagtgtt tgccagttac tgctccagag    420
aacggtaaga ttgtttcctc cgctatggaa ccagatagag agtaccactt cggtcaggct    480
gttagattcg tttgtaactc cggttacaag attgaaggtg acgaagagat gcactgttct    540
gatgacggtt tctggtccaa agaaaagcca aagtgtgttg agatttcctg taagtcccca    600
gacgttatta acggttcccc aatctcccaa aagatcatct acaaagagaa cgagagattc    660
cagtacaagt gtaacatggg ttacgagtac tctgaaagag gtgacgctgt ttgtactgaa    720
tctggttgga gaccattgcc atcctgtgaa gagaagtcct gtgacaaccc atacattcca    780
aacggtgact actccccatt gagaatcaag cacagaactg gtgacgagat cacttaccag    840
tgtagaaacg gtttctaccc agctactaga ggtaacactg ctaagtgtac ttccactggt    900
tggattccag ctccaagatg tactttgaag ccatgtgact acccagatat caagcacggt    960
ggtttgtacc acgagaacat gagaagacca tacttcccag ttgctgttgg aaagtactac   1020
tcctactact gtgacgaaca cttcgaaact ccatctggtt cttactggga ccacatccac   1080
tgtactcaag atggttggtc cccagctgtt ccatgtttga gaaaatgtta cttcccatac   1140
ttggagaacg gttacaacca gaactacggt agaaagttcg ttcagggaaa gtccattgac   1200
gttgcttgtc atccaggtta cgctttgcca aaggctcaga ctactgttac ttgtatggaa   1260
aacggttggt cccctactcc tagatgtatc agagttaaga cttgttccaa gtcctccatc   1320
gacattgaga acggtttcat ttccgagtcc cagtacactt acgctttgaa agagaaggct   1380
aagtaccagt gtaaattggg atacgttact gctgacggtg aaacttccgg ttccatcact   1440
tgtggtaagg atggttggtc tgctcaacca acttgtatca agtcttgtga catcccagtt   1500
ttcatgaacg ctagaactaa gaacgacttc acatggttca agttgaacga cactttggac   1560
tacgaatgtc acgacggtta cgaatctaac actggttcca ctactggttc catcgtttgt   1620
ggttacaacg gttggtctga cttgccaatc tgttacgaga gagagtgcga gttgccaaag   1680
atcgacgttc atttggttcc agacagaaag aaggaccagt acaaggttgg tgaggttttg   1740
aagttctcct gtaagccagg tttcactatc gttggtccaa actccgttca gtgttaccat   1800
ttcggtttgt ccccagactt gcctatttgt aaagagcagg ttcagtcttg cggtccacca   1860
ccagaattgt tgaacggtaa cgttaaagaa aagactaaag aagagtacgg tcactctgag   1920
gttgttgagt actactgtaa cccaagattc ttgatgaagg gtccaaacaa gatccaatgt   1980
gttgacggtg agtggactac tttgccagtt tgtatcgttg aagagtccac ttgtggtgac   2040
attccagaat tggaacacgg ttgggctcaa ttgtcatccc caccatacta ctacggtgac   2100
tccgttgagt tctagtgttc cgagtccttc actatgattg gtcacagatc catcacatgt   2160
atccacggtg tttggactca attgccacag tgtgttgcta tcgacaagtt gaagaagtgt   2220
aaatcctcca acttgatcat cttggaggaa cacttgaaga acaagaaaga gttcgaccac   2280
aactccaaca tcagatacag atgtagaggt aaagagggtt ggattcacac tgtttgtatc   2340
aacggtagat gggaccctga agttaactgt tccatggctc agattcagtt gtgtccacca   2400
cctccacaaa ttccaaactc ccacaacatg actactactt tgaactacag agatggtgag   2460
aaggtttccg ttttgtgtca agagaactac ttgatccaag agggtgagga aatcacttgt   2520
aaggacggta gatggcaatc catcccattg tgtgttgaga agatcccatg ttcccaacca   2580
```

ccacaaattg agcacggtac tatcaactct tccagatcct ctcaagagtc ttacgctcac 2640
ggtactaagt tgtcctacac ttgtgagggt ggtttcagaa tctctgagga ataggagact 2700
acttgttaca tgggaaagtg gtcctctcca ccacaatgtg aaggtttgcc ttgtaagtct 2760
ccaccagaga tttctcacgg tgttgttgct cacatgtccg actcttacca atacggtgaa 2820
gaggttactt acaagtgttt cgagggtttc ggtattgatg gtccagctat cgctaagtgt 2880
ttgggtgaaa agtggtccca tcctccatcc tgtatcaaga ctgactgttt gtccttgcca 2940
tctttcgaga acgctatccc aatgggtgaa aagaaggacg tttacaaggc tggtgaacag 3000
gttacataca cttgtgctac ttactacaag atggacggtg cttccaacgt tacttgtatc 3060
aactccagat ggactggtag accaacttgt agagacactt cctgtgttaa cccaccaact 3120
gttcagaacg cttacatcgt ttccagacag atgtctaagt acccatccgg tgagagagtt 3180
agataccaat gtagatcccc atacgagatg ttcggtgacg aagaggttat gtgtttgaac 3240
ggtaattgga ctgaaccacc acagtgtaag gactccactg gtaagtgtgg tccacctcca 3300
ccaattgaca acggtgacat cacttctttc ccattgtccg tttacgctcc agcttcttcc 3360
gttgagtacc agtgtcagaa cttgtaccag ttggagggta acaagagaat cacttgtaga 3420
aacggacaat ggtctgagcc accaaagtgt ttgcacccat gtgttatctc cagagaaatc 3480
atggaaaact acaacattgc tttgagatgg actgctaagc agaagttgta ctccagaaca 3540
ggtgagtctg ttgagtttgt ttgtaagaga ggttacagat tgtcctccag atcccacact 3600
ttgagaacta catgttggga cggaaagttg gagtacccaa cttgtgctaa gagataatga 3660
gcggccgctt aattaa 3676

<210> SEQ ID NO 7
<211> LENGTH: 3934
<212> TYPE: DNA
<213> ORGANISM: Artificial
<220> FEATURE:
<223> OTHER INFORMATION: Codon optimised human hactor H variant

<400> SEQUENCE: 7
ggcgcgccgg atccaaaaat gagattccca tccatcttca ctgctgtttt gttcgctgct 60
tcttctgctt tggctgctcc agttaacact actactgagg acgagactgc tcaaattcca 120
gctgaggctg ttattggtta ctctgacttg gaaggtgatt tcgacgttgc tgttttgcca 180
ttctccaact ccactaacaa cggtttgttg ttcatcaaca ctactatcgc ttccattgct 240
gctaaagaag agggagtttc cctcgagaag agagaggact gtaacgaatt gccaccgcgg 300
agaaacactg agattttgac tggttcctgg tccgatcaaa cttacccaga gggtactcag 360
gctatctaca agtgtagacc aggttacaga tccttgggta acgttatcat ggtttgtaga 420
aagggtgagt gggttgcttt gaacccattg agaaagtgtc agaaaagacc atgtggtcac 480
ccaggtgata ctccattcgg tactttcact ttgactggtg gtaacgtttt cgagtacggt 540
gttaaggctg tttacacttg taacgagggt taccagttgt tgggtgagat caactacaga 600
gagtgtgata ctgacggttg gactaacgac attccaatct gtgaggttgt taagtgtttg 660
ccagttactg ctccagagaa cggtaagatt gtttcctccg ctatggaacc agatagagag 720
taccacttcg gtcaggctgt tagattcgtt tgtaactccg gttacaagat tgaaggtgac 780
gaagagatgc actgttctga tgacggtttc tggtccaaag aaaagccaaa gtgtgttgag 840
atttcctgta agtccccaga cgttattaac ggttccccaa tctcccaaaa gatcatctac 900

-continued

```
aaagagaacg agagattcca gtacaagtgt aacatgggtt acgagtactc tgaaagaggt    960
gacgctgttt gtactgaatc tggttggaga ccattgccat cctgtgaaga gaagtcctgt   1020
gacaacccat acattccaaa cggtgactac tccccattga gaatcaagca cagaactggt   1080
gacgagatca cttaccagtg tagaaacggt ttctacccag ctactagagg taacactgct   1140
aagtgtactt ccactggttg gattccagct ccaagatgta ctttgaagcc atgtgactac   1200
ccagatatca agcacggtgg tttgtaccac gagaacatga gaagaccata cttcccagtt   1260
gctgttggaa agtactactc ctactactgt gacgaacact tcgaaactcc atctggttct   1320
tactgggacc acatccactg tactcaagat ggttggtccc cagctgttcc atgtttgaga   1380
aaatgttact tcccatactt ggagaacggt tacaaccaga accatggtag aaagttcgtt   1440
cagggaaagt ccattgacgt tgcttgtcat ccaggttacg ctttgccaaa ggctcagact   1500
actgttactt gtatggaaaa cggttggtcc cctactccta gatgtatcag agttaagact   1560
tgttccaagt cctccatcga cattgagaac ggtttcattt ccgagtccca gtacacttac   1620
gctttgaaag agaaggctaa gtaccagtgt aaattgggat acgttactgc tgacggtgaa   1680
acttccggtt ccatcacttg tggtaaggat ggttggtctg ctcaaccaac ttgtatcaag   1740
tcttgtgaca tcccagtttt catgaacgct agaactaaga acgacttcac atggttcaag   1800
ttgaacgaca ctttggacta cgaatgtcac gacggttacg aatctaacac tggttccact   1860
actggttcca tcgtttgtgg ttacaacggt tggtctgact tgccaatctg ttacgagaga   1920
gagtgcgagt tgccaaagat cgacgttcat ttggttccag acagaaagaa ggaccagtac   1980
aaggttggtg aggttttgaa gttctcctgt aagccaggtt tcactatcgt tggtccaaac   2040
tccgttcagt gttaccattt cggtttgtcc ccagacttgc ctatttgtaa agagcaggtt   2100
cagtcttgcg gtccaccacc agaattgttg aacggtaacg ttaaagaaaa gactaaagaa   2160
gagtacggtc actctgaggt tgttgagtac tactgtaacc caagattctt gatgaagggt   2220
ccaaacaaga tccaatgtgt tgacggtgag tggactactt tgccagtttg tatcgttgaa   2280
gagtccactt gtggtgacat tccagaattg gaacacggtt gggctcaatt gtcatcccca   2340
ccatactact acggtgactc cgttgagttc aactgttccg agtccttcac tatgattggt   2400
cacagatcca tcacatgtat ccacggtgtt tggactcaat tgccacagtg tgttgctatc   2460
gacaagttga agaagtgtaa atcctccaac ttgatcatct tggaggaaca cttgaagaac   2520
aagaaagagt tcgaccacaa ctccaacatc agatacagat gtagaggtaa agagggttgg   2580
attcacactg tttgtatcaa cggtagatgg gaccctgaag ttaactgttc catggctcag   2640
attcagttgt gtccaccacc tccacaaatt ccaaactccc acaacatgac tactactttg   2700
aactacagag atggtgagaa ggtttccgtt ttgtgtcaag agaactactt gatccaagag   2760
ggtgaggaaa tcacttgtaa ggacggtaga tggcaatcca tcccattgtg tgttgagaag   2820
atcccatgtt cccaaccacc acaaattgag cacggtacta tcaactcttc cagatcctct   2880
caagagtctt acgctcacgg tactaagttg tcctacactt gtgagggtgg tttcagaatc   2940
tctgaggaaa acgagactac ttgttacatg ggaaagtggt cctctccacc acaatgtgaa   3000
ggtttgcctt gtaagtctcc accagagatt tctcacggtg ttgttgctca catgtccgac   3060
tcttaccaat acggtgaaga ggttacttac aagtgtttcg agggtttcgg tattgatggt   3120
ccagctatcg ctaagtgttt gggtgaaaag tggtcccatc ctccatcctg tatcaagact   3180
gactgtttgt ccttgccatc tttcgagaac gctatcccaa tgggtgaaaa gaaggacgtt   3240
tacaaggctg gtgaacaggt tacatacact tgtgctactt actacaagat ggacggtgct   3300
```

-continued tccaacgtta cttgtatcaa ctccagatgg actggtagac caacttgtag agacacttcc 3360
tgtgttaacc caccaactgt tcagaacgct tacatcgttt ccagacagat gtctaagtac 3420
ccatccggtg agagagttag ataccaatgt agatccccat acgagatgtt cggtgacgaa 3480
gaggttatgt gtttgaacgg taattggact gaaccaccac agtgtaagga ctccactggt 3540
aagtgtggtc cacctccacc aattgacaac ggtgacatca cttctttccc attgtccgtt 3600
tacgctccag cttcttccgt tgagtaccag tgtcagaact tgtaccagtt ggagggtaac 3660
aagagaatca cttgtagaaa cggacaatgg tctgagccac caaagtgttt gcacccatgt 3720
gttatctcca gagaaatcat ggaaaactac aacattgctt tgagatggac tgctaagcag 3780
aagttgtact ccagaacagg tgagtctgtt gagtttgttt gtaagagagg ttacagattg 3840
tcctccagat cccacacttt gagaactaca tgttgggacg gaaagttgga gtacccaact 3900
tgtgctaaga gataatgagc ggccgcttaa ttaa 3934

<210> SEQ ID NO 8
<211> LENGTH: 2848
<212> TYPE: DNA
<213> ORGANISM: Artificial
<220> FEATURE:
<223> OTHER INFORMATION: Codon optimised human hactor H variant

<400> SEQUENCE: 8
ggcgcgccgg atccaaaaat gagattccca tccatcttca ctgctgtttt gttcgctgct 60
tcttctgctt tggctgctcc agttaacact actactgagg acgagactgc tcaaattcca 120
gctgaggctg ttattggtta ctctgacttg gaaggtgatt tcgacgttgc tgttttgcca 180
ttctccaact ccactaacaa cggtttgttg ttcatcaaca ctactatcgc ttccattgct 240
gctaaagaag agggagtttc cctcgagaag agagaggact gtaacgaatt gccaccgcgg 300
agaaacactg agattttgac tggttcctgg tccgatcaaa cttacccaga gggtactcag 360
gctatctaca agtgtagacc aggttacaga tccttgggta acattatcat ggtttgtaga 420
aagggtgagt gggttgcttt gaacccattg agaaagtgtc agaaaagacc atgtggtcac 480
ccaggtgata ctccattcgg tactttcact ttgactggtg gtaacgtttt cgagtacggt 540
gttaaggctg tttacacttg taacgagggt taccagttgt tgggtgagat caactacaga 600
gagtgtgata ctgacggttg gactaacgac attccaatct gtgaggttgt taagtgtttg 660
ccagttactg ctccagagaa cggtaagatt gtttcctccg ctatggaacc agatagagag 720
taccacttcg gtcaggctgt tagattcgtt tgtaactccg gttacaagat tgaaggtgac 780
gaagagatgc actgttctga tgacggtttc tggtccaaag aaaagccaaa gtgtgttgag 840
atttcctgta agtccccaga cgttattaac ggttccccaa tctcccaaaa gatcatctac 900
aaagagaacg agagattcca gtacaagtgt aacatgggtt acgagtactc tgaaagaggt 960
gacgctgttt gtactgaatc tggttggaga ccattgccat cctgtgaaga gaagtcctgt 1020
gacaacccat acattccaaa cggtgactac tccccattga gaatcaagca cagaactggt 1080
gacgagatca cttaccagtg tagaaacggt ttctacccag ctactagagg taacactgct 1140
aagtgtactt ccactggttg gattccagct ccaagatgta ctttgaagcc atgtgactac 1200
ccagatatca agcacggtgg tttgtaccac gagaacatga gaagaccata cttcccagtt 1260
gctgttggaa agtactactc ctactactgt gacgaacact tcgaaactcc atctggttct 1320
tactgggacc acatccactg tactcaagat ggttggtccc cagctgttcc atgtttgaga 1380

-continued

```
aaatgttact tcccatactt ggagaacggt tacaaccaga actacggtag aaagttcgtt   1440
cagggaaagt ccattgacgt tgcttgtcat ccaggttacg ctttgccaaa ggctcagact   1500
actgttactt gtatggaaaa cggttggtcc cctactccta gatgtatcag agttaagact   1560
tgttccaagt cctccatcga cattgagaac ggtttcattt ccgagtccca gtacacttac   1620
gctttgaaag agaaggctaa gtaccagtgt aaattgggat acgttactgc tgacggtgaa   1680
acttccggtt ccatcacttg tggtaaggat ggttggtctg ctcaaccaac ttgtatcaag   1740
tcttgtgaca tcccagtttt catgaacgct agaactaaga acgacttcac atggttcaag   1800
ttgaacgaca ctttggacta cgaatgtcac gacggttacg aatctaacac tggttccact   1860
actggttcca tcgtttgtgg ttacaacggt tggtctgact tgccaatctg ttacgagttg   1920
ccttgtaagt ctccaccaga gatttctcac ggtgttgttg ctcacatgtc cgactcttac   1980
caatacggtg aagaggttac ttacaagtgt ttcgagggtt tcggtattga tggtccagct   2040
atcgctaagt gtttgggtga aaagtggtcc catcctccat cctgtatcaa gactgactgt   2100
ttgtccttgc catctttcga gaacgctatc ccaatgggtg aaaagaagga cgtttacaag   2160
gctggtgaac aggttacata cacttgtgct acttactaca agatggacgg tgcttccaac   2220
gttacttgta tcaactccag atggactggt agaccaactt gtagagacac ttcctgtgtt   2280
aacccaccaa ctgttcagaa cgcttacatc gtttccagac agatgtctaa gtacccatcc   2340
ggtgagagag ttagatacca atgtagatcc ccatacgaga tgttcggtga cgaagaggtt   2400
atgtgtttga acggtaattg gactgaacca ccacagtgta aggactccac tggtaagtgt   2460
ggtccacctc caccaattga caacggtgac atcacttctt tcccattgtc cgtttacgct   2520
ccagcttctt ccgttgagta ccagtgtcag aacttgtacc agttggaggg taacaagaga   2580
atcacttgta gaaacggaca atggtctgag ccaccaaagt gtttgcaccc atgtgttatc   2640
tccagagaaa tcatggaaaa ctacaacatt gctttgagat ggactgctaa gcagaagttg   2700
tactccagaa caggtgagtc tgttgagttt gtttgtaaga gaggttacag attgtcctcc   2760
agatcccaca ctttgagaac tacatgttgg gacggaaagt tggagtaccc aacttgtgct   2820
aagagataat gagcggccgc ttaattaa                                      2848
```

<210> SEQ ID NO 9
<211> LENGTH: 3742
<212> TYPE: DNA
<213> ORGANISM: Artificial
<220> FEATURE:
<223> OTHER INFORMATION: Codon optimised mouse hactor H variant

<400> SEQUENCE: 9

```
ggcgcgccgg atccaaaaat gagattgtcc gctagaatca tctggttgat cttgtggact     60
gtttgtgctg ctgaggattg taaaggtcca ccaccgcggg aaaactccga gattttgtct    120
ggttcttggt ccgaacaatt gtacccagag ggtactcaag ctacttacaa gtgtagacca    180
ggttacagaa ctttgggtac tatcgttaag gtttgtaaga acggaaagtg ggttgcttct    240
aacccatcca gaatctgtag aaagaaacca tgtggtcacc caggtgatac tccattcggt    300
tccttcagat tggctgttgg ttcccaattc gagttcggtg ctaaggttgt ttacacttgt    360
gacgacggtt accaattgtt gggtgagatc gactacagag aatgtggtgc tgacggttgg    420
attaacgaca tcccattgtg tgaggttgtt aagtgtttgc cagttactga gttggagaac    480
ggtagaattg tttctggtgc tgctgaaact gaccaagagt actacttcgg acaggttgtt    540
agattcgagt gtaactccgg tttcaagatc gaaggtcaca aagagattca ctgttccgag    600
```

-continued

```
aacggtttgt ggtctaacga gaagccaaga tgtgttgaga ttttgtgtac tccaccaaga    660
gttgaaaacg gtgacggtat caacgttaag ccagtttaca aagagaacga gagataccac    720
tacaagtgta agcacggtta cgttccaaaa gaaagaggtg acgctgtttg tactggttct    780
ggttggtcct ctcaaccatt ctgtgaagag aagagatgtt ccccaccata catcttgaac    840
ggtatctaca ctccacacag aatcattcac agatccgacg acgagattag atacgaatgt    900
aactacggat tctacccagt tactggttcc actgtttcca agtgtactcc aactggttgg    960
attccagttc caagatgtac tttgaagcca tgtgagttcc cacaattcaa gtacggtaga   1020
ttgtactacg aagagtcctt gagaccaaac ttcccagttt ccatcggtaa caagtactcc   1080
tacaagtgtg acaacggttt ctctccacca tctggttact cttgggacta cttgagatgt   1140
actgctcaag gttgggaacc agaggttcca tgtgttagaa agtgtgtttt ccactacgtt   1200
gagaacggtg attctgctta ctgggagaag gtttacgttc aaggtcagtc cttgaaggtt   1260
cagtgttaca acggttactc cttgcaaaac ggtcaggaca ctatgacttg tactgagaac   1320
ggttggtcac caccaccaaa gtgtatcaga atcaagactt gttccgcttc cgacattcac   1380
atcgacaacg gattcttgtc tgagtcctcc tccatttacg ctttgaacag agagacttcc   1440
tacagatgta agcagggata cgttacaaac actggtgaga tttccggttc catcacttgt   1500
ttgcagaatg gttggtcccc acagccatct tgtattaagt cctgtgacat gccagttttc   1560
gagaactcca tcactaagaa cactagaaca tggttcaagt tgaacgacaa gttggactac   1620
gagtgtttgg ttggtttcga gaacgagtac aagcacacta agggttccat cacatgtact   1680
tactacggtt ggtctgacac tccatcctgt tacgaaagag agtgttccgt tccaactttg   1740
gacagaaagt tggttgtttc cccaagaaaa gagaagtaca gagttggaga cttgttggag   1800
ttctcttgtc actctggtca tagagttggt ccagactccg ttcaatgtta ccactttgga   1860
tggtccccag gttttccaac ttgtaagggt caggttgctt cttgtgctcc accattggag   1920
attttgaacg gtgagatcaa cggtgctaag aaggttgaat actcccacgg tgaagttgtt   1980
aagtacgact gtaagccaag attcttgttg aagggtccaa acaagatcca atgtgttgac   2040
ggtaactgga ctactttgcc agtttgtatc gaggaagaaa gaacttgcgg agacatccca   2100
gaattggaac acggttccgc taagtgttct gttccaccat accaccatgg tgattccgtt   2160
gagttcatct gtgaggaaaa cttcactatg atcggtcacg gttccgtttc ttgtatttcc   2220
ggtaagtgga ctcagttgcc aaagtgtgtt gctactgacc agttggagaa gtgtagagtt   2280
ttgaagtcca ctggtatcga ggctatcaag ccaaagttga ctgagttcac tcacaactcc   2340
actatggact acaaatgtag agacaagcaa gagtacgaga gatccatctg tatcaacggt   2400
aaatgggacc cagaaccaaa ctgtacttcc aagacttctt gtccaccacc accacaaatt   2460
ccaaacactc aggttatcga gactactgtt aagtacttgg acggtgagaa gttgtccgtt   2520
ttgtgtcagg acaactactt gactcaagac tccgaagaga tggtttgtaa ggacggtaga   2580
tggcaatctt tgccaagatg tatcgagaag atcccatgtt ctcagccacc aactattgag   2640
cacggttcca ttaacttgcc aagatcctcc gaagaaagaa gagactccat cgaatcctct   2700
tctcacgaac acggtactac tttctcttac gtttgtgatg acggtttcag aatcccagaa   2760
gagaacagaa tcacttgtta catgggaaag tggtccactc cacctagatg tgttggtttg   2820
ccatgtggtc caccaccttc tattccattg ggtactgttt ctttggagtt ggagtcctac   2880
caacacggtg aagaggttac ttaccactgt tccactggtt tcggtattga tggtccagct   2940
```

-continued

```
ttcattatct gtgagggtgg taagtggtct gatccaccta agtgtattaa gactgactgt   3000

gacgttttgc caactgttaa gaacgctatc atcagaggta agtccaagaa gtcctacaga   3060

actggagagc aggttacttt cagatgtcag tccccatacc aaatgaacgg ttccgacact   3120

gttacttgtg ttaactccag atggatcggt caaccagttt gtaaggataa ctcctgtgtt   3180

gatccaccac atgttccaaa cgctactatc gttactagaa ctaagaacaa gtacttgcat   3240

ggtgacagag ttagatatga gtgtaacaag ccattggagt tgttcggtca agttgaggtt   3300

atgtgtgaga acggtatctg gactgagaag ccaaagtgta gagactccac tggtaagtgt   3360

ggtcctccac caccaattga caacggtgac atcacttctt tgtccttgcc agtttacgaa   3420

cctttgtcct ccgttgagta ccaatgtcag aagtactact tgttgaaagg taagaaaact   3480

atcacttgta ctaatggtaa atggtccgag ccaccaactt gtttgcacgc ttgtgttatc   3540

ccagagaaca tcatggaatc ccacaacatc atcttgaagt ggagacacac tgagaagatt   3600

tactctcact ccggtgagga cattgagttc ggttgtaagt acggttacta caaggctaga   3660

gactctccac cattcagaac taagtgtatc aacggaacta tcaactaccc aacttgtgtt   3720

taatgagcgg ccgcttaatt aa                                             3742
```

<210> SEQ ID NO 10
<211> LENGTH: 3943
<212> TYPE: DNA
<213> ORGANISM: Artificial
<220> FEATURE:
<223> OTHER INFORMATION: Codon optimised mouse hactor H variant

<400> SEQUENCE: 10

```
ggcgcgccgg atccaaaaat gagattccca tccatcttca ctgctgtttt gttcgctgct     60

tcttctgctt tggctgctcc agttaacact actactgagg acgagactgc tcaaattcca    120

gctgaggctg ttattggtta ctctgacttg gaaggtgatt tcgacgttgc tgttttgcca    180

ttctccaact ccactaacaa cggtttgttg ttcatcaaca ctactatcgc ttccattgct    240

gctaaagaag agggagtttc cctcgagaag agagaggatt gtaaaggtcc accaccgcgg    300

gaaaactccg agattttgtc tggttcttgg tccgaacaat tgtacccaga gggtactcaa    360

gctacttaca agtgtagacc aggttacaga actttgggta ctatcgttaa ggtttgtaag    420

aacggaaagt gggttgcttc tcaaccatcc agaatctgta gaaagaaacc atgtggtcac    480

ccaggtgata ctccattcgg ttccttcaga ttggctgttg gttcccaatt cgagttcggt    540

gctaaggttg tttacacttg tgacgacggt taccaattgt tgggtgagat cgactacaga    600

gaatgtggtg ctgacggttg gattaacgac atcccattgt gtgaggttgt taagtgtttg    660

ccagttactg agttggagaa cggtagaatt gtttctggtg ctgctgaaac tgaccaagag    720

tactacttcg gacaggttgt tagattcgag tgtaactccg gtttcaagat cgaaggtcac    780

aaagagattc actgttccga gaacggtttg tggtctaacg agaagccaag atgtgttgag    840

attttgtgta ctccaccaag agttgaaaac ggtgacggta tcaacgttaa gccagtttac    900

aaagagaacg agagatacca ctacaagtgt aagcacggtt acgttccaaa agaaagaggt    960

gacgctgttt gtactggttc tggttggtcc tctcaaccat tctgtgaaga gaagagatgt   1020

tccccaccat acatcttgaa cggtatctac actccacaca gaatcattca cagatccgac   1080

gacgagatta gatacgaatg taactacgga ttctacccag ttactggttc cactgtttcc   1140

aagtgtactc caactggttg gattccagtt ccaagatgta ctttgaagcc atgtgagttc   1200

ccacaattca agtacggtag attgtactac gaagagtcct tgagaccaaa cttcccagtt   1260
```

-continued

```
tccatcggta acaagtactc ctacaagtgt gacaacggtt tctctccacc atctggttac   1320
tcttgggact acttgagatg tactgctcaa ggttgggaac cagaggttcc atgtgttaga   1380
aagtgtgttt tccactacgt tgagaacggt gattctgctt actgggagaa ggtttacgtt   1440
caaggtcagt ccttgaaggt tcagtgttac aacggttact ccttgcaaaa cggtcaggac   1500
actatgactt gtactgagaa cggttggtca ccaccaccaa agtgtatcag aatcaagact   1560
tgttccgctt ccgacattca catcgacaac ggattcttgt ctgagtcctc ctccatttac   1620
gctttgaaca gagagacttc ctacagatgt aagcagggat acgttacaaa cactggtgag   1680
atttccggtt ccatcacttg tttgcagaat ggttggtccc cacagccatc ttgtattaag   1740
tcctgtgaca tgccagtttt cgagaactcc atcactaaga acactagaac atggttcaag   1800
ttgaacgaca agttggacta cgagtgtttg gttggtttcg agaacgagta caagcacact   1860
aagggttcca tcacatgtac ttactacggt tggtctgaca ctccatcctg ttacgaaaga   1920
gagtgttccg ttccaacttt ggacagaaag ttggttgttt ccccaagaaa agagaagtac   1980
agagttggag acttgttgga gttctcttgt cactctggtc atagagttgg tccagactcc   2040
gttcaatgtt accactttgg atggtcccca ggttttccaa cttgtaaggg tcaggttgct   2100
tcttgtgctc caccattgga gattttgaac ggtgagatca acggtgctaa gaaggttgaa   2160
tactcccacg gtgaagttgt taagtacgac tgtaagccaa gattcttgtt gaagggtcca   2220
aacaagatcc aatgtgttga cggtcaatgg actactttgc cagtttgtat cgaggaagaa   2280
agaacttgcg gagacatccc agaattggaa cacggttccg ctaagtgttc tgttccacca   2340
taccaccatg gtgattccgt tgagttcatc tgtgaggaac aattcactat gatcggtcac   2400
ggttccgttt cttgtatttc cggtaagtgg actcagttgc caaagtgtgt tgctactgac   2460
cagttggaga agtgtagagt tttgaagtcc actggtatcg aggctatcaa gccaaagttg   2520
actgagttca ctcaccagtc cactatggac tacaaatgta gagacaagca agagtacgag   2580
agatccatct gtatcaacgg taaatgggac ccagaaccac aatgtacttc caagacttct   2640
tgtccaccac caccacaaat tccaaacact caggttatcg agactactgt taagtacttg   2700
gacggtgaga agttgtccgt tttgtgtcag gacaactact tgactcaaga ctccgaagag   2760
atggtttgta aggacggtag atggcaatct ttgccaagat gtatcgagaa gatcccatgt   2820
tctcagccac caactattga gcacggttcc attaacttgc caagatcctc cgaagaaaga   2880
agagactcca tcgaatcctc ttctcacgaa cacggtacta ctttctctta cgtttgtgat   2940
gacggtttca gaatcccaga agagaacaga atcacttgtt acatgggaaa gtggtccact   3000
ccacctagat gtgttggttt gccatgtggt ccaccacctt ctattccatt gggtactgtt   3060
tctttggagt tggagtccta ccaacacggt gaagaggtta cttaccactg ttccactggt   3120
ttcggtattg atggtccagc tttcattatc tgtgagggtg gtaagtggtc tgatccacct   3180
aagtgtatta agactgactg tgacgttttg ccaactgtta agaacgctat catcagaggt   3240
aagtccaaga agtcctacag aactggagag caggttactt tcagatgtca gtccccatac   3300
caaatgcaag gttccgacac tgttacttgt gttaactcca gatggatcgg tcaaccagtt   3360
tgtaaggata actcctgtgt tgatccacca catgttccac aagctactat cgttactaga   3420
actaagaaca agtacttgca tggtgacaga gttagatatg agtgtaacaa gccattggag   3480
ttgttcggtc aagttgaggt tatgtgtgag aacggtatct ggactgagaa gccaaagtgt   3540
agagactcca ctggtaagtg tggtcctcca ccaccaattg acaacggtga catcacttct   3600
```

-continued

```
ttgtccttgc cagtttacga acctttgtcc tccgttgagt accaatgtca gaagtactac   3660

ttgttgaaag gtaagaaaac tatcacttgt actaatggta aatggtccga gccaccaact   3720

tgtttgcacg cttgtgttat cccagagaac atcatggaat cccacaacat catcttgaag   3780

tggagacaca ctgagaagat ttactctcac tccggtgagg acattgagtt cggttgtaag   3840

tacggttact acaaggctag agactctcca ccattcagaa ctaagtgtat ccaaggaact   3900

atcaactacc caacttgtgt ttaatgagcg gccgcttaat taa                     3943
```

```
<210> SEQ ID NO 11
<211> LENGTH: 3742
<212> TYPE: DNA
<213> ORGANISM: Artificial
<220> FEATURE:
<223> OTHER INFORMATION: Codon optimised mouse hactor H variant

<400> SEQUENCE: 11

ggcgcgccgg atccaaaaat gagattgtcc gctagaatca tctggttgat cttgtggact     60

gtttgtgctg ctgaggattg taaaggtcca ccaccgcggg aaaactccga gattttgtct    120

ggttcttggt ccgaacaatt gtacccagag ggtactcaag ctacttacaa gtgtagacca    180

ggttacagaa ctttgggtac tatcgttaag gtttgtaaga acggaaagtg ggttgcttct    240

caaccatcca gaatctgtag aaagaaacca tgtggtcacc caggtgatac tccattcggt    300

tccttcagat tggctgttgg ttcccaattc gagttcggtg ctaaggttgt ttacacttgt    360

gacgacggtt accaattgtt gggtgagatc gactacagag aatgtggtgc tgacggttgg    420

attaacgaca tcccattgtg tgaggttgtt aagtgtttgc cagttactga gttggagaac    480

ggtagaattg tttctggtgc tgctgaaact gaccaagagt actacttcgg acaggttgtt    540

agattcgagt gtaactccgg tttcaagatc gaaggtcaca aagagattca ctgttccgag    600

aacggtttgt ggtctaacga gaagccaaga tgtgttgaga ttttgtgtac tccaccaaga    660

gttgaaaacg gtgacggtat caacgttaag ccagtttaca aagagaacga gagataccac    720

tacaagtgta agcacggtta cgttccaaaa gaaagaggtg acgctgtttg tactggttct    780

ggttggtcct ctcaaccatt ctgtgaagag aagagatgtt ccccaccata catcttgaac    840

ggtatctaca ctccacacag aatcattcac agatccgacg acgagattag atacgaatgt    900

aactacggat tctacccagt tactggttcc actgtttcca agtgtactcc aactggttgg    960

attccagttc caagatgtac tttgaagcca tgtgagttcc cacaattcaa gtacggtaga   1020

ttgtactacg aagagtcctt gagaccaaac ttcccagttt ccatcggtaa caagtactcc   1080

tacaagtgtg acaacggttt ctctccacca tctggttact cttgggacta cttgagatgt   1140

actgctcaag gttgggaacc agaggttcca tgtgttagaa agtgtgtttt ccactacgtt   1200

gagaacggtg attctgctta ctgggagaag gtttacgttc aaggtcagtc cttgaaggtt   1260

cagtgttaca acggttactc cttgcaaaac ggtcaggaca ctatgacttg tactgagaac   1320

ggttggtcac caccaccaaa gtgtatcaga atcaagactt gttccgcttc cgacattcac   1380

atcgacaacg gattcttgtc tgagtcctcc tccatttacg ctttgaacag agagacttcc   1440

tacagatgta agcagggata cgttacaaac actggtgaga tttccggttc catcacttgt   1500

ttgcagaatg gttggtcccc acagccatct tgtattaagt cctgtgacat gccagttttc   1560

gagaactcca tcactaagaa cactagaaca tggttcaagt tgaacgacaa gttggactac   1620

gagtgtttgg ttggtttcga gaacgagtac aagcacacta agggttccat cacatgtact   1680

tactacggtt ggtctgacac tccatcctgt tacgaaagag agtgttccgt tccaactttg   1740
```

-continued

```
gacagaaagt tggttgtttc cccaagaaaa gagaagtaca gagttggaga cttgttggag   1800
ttctcttgtc actctggtca tagagttggt ccagactccg ttcaatgtta ccactttgga   1860
tggtccccag gttttccaac ttgtaagggt caggttgctt cttgtgctcc accattggag   1920
attttgaacg gtgagatcaa cggtgctaag aaggttgaat actcccacgg tgaagttgtt   1980
aagtacgact gtaagccaag attcttgttg aagggtccaa acaagatcca atgtgttgac   2040
ggtcaatgga ctactttgcc agtttgtatc gaggaagaaa gaacttgcgg agacatccca   2100
gaattggaac acggttccgc taagtgttct gttccaccat accaccatgg tgattccgtt   2160
gagttcatct gtgaggagta gttcactatg atcggtcacg gttccgtttc ttgtatttcc   2220
ggtaagtgga ctcagttgcc aaagtgtgtt gctactgacc agttggagaa gtgtagagtt   2280
ttgaagtcca ctggtatcga ggctatcaag ccaaagttga ctgagttcac tcaccagtct   2340
actatggact acaaatgtag agacaagcaa gagtacgaga gatccatctg tatcaacggt   2400
aaatgggacc cagaaccaca atgtacttcc aagacttctt gtccaccacc accacaaatt   2460
ccaaacactc aggttatcga gactactgtt aagtacttgg acggtgagaa gttgtccgtt   2520
ttgtgtcagg acaactactt gactcaagac tccgaagaga tggtttgtaa ggacggtaga   2580
tggcaatctt tgccaagatg tatcgagaag atcccatgtt ctcagccacc aactattgag   2640
cacggttcca ttaacttgcc aagatcctcc gaagaaagaa gagactccat cgaatcctct   2700
tctcacgaac acggtactac tttctcttac gtttgtgatg acggtttcag aatcccagaa   2760
gagaacagaa tcacttgtta catgggaaag tggtccactc cacctagatg tgttggtttg   2820
ccatgtggtc caccaccttc tattccattg ggtactgttt ctttggagtt ggagtcctac   2880
caacacggtg aagaggttac ttaccactgt tccactggtt tcggtattga tggtccagct   2940
ttcattatct gtgagggtgg taagtggtct gatccaccta agtgtattaa gactgactgt   3000
gacgttttgc caactgttaa gaacgctatc atcagaggta agtccaagaa gtcctacaga   3060
actggagagc aggttacttt cagatgtcag tccccatacc aaatgcaagg ttccgacact   3120
gttacttgtg ttaactccag atggatcggt caaccagttt gtaaggataa ctcctgtgtt   3180
gatccaccac atgttccaca agctactatc gttactagaa ctaagaacaa gtacttgcat   3240
ggtgacagag ttagatatga gtgtaacaag ccattggagt tgttcggtca agttgaggtt   3300
atgtgtgaga acggtatctg gactgagaag ccaaagtgta gagactccac tggtaagtgt   3360
ggtcctccac caccaattga caacggtgac atcacttctt tgtccttgcc agtttacgaa   3420
cctttgtcct ccgttgagta ccaatgtcag aagtactact tgttgaaagg taagaaaact   3480
atcacttgta ctaatggtaa atggtccgag ccaccaactt gtttgcacgc ttgtgttatc   3540
ccagagaaca tcatggaatc ccacaacatc atcttgaagt ggagacacac tgagaagatt   3600
tactctcact ccggtgagga cattgagttc ggttgtaagt acggttacta caaggctaga   3660
gactctccac cattcagaac taagtgtatc caaggaacta tcaactaccc aacttgtgtt   3720
taatgagcgg ccgcttaatt aa                                            3742
```

<210> SEQ ID NO 12
<211> LENGTH: 3742
<212> TYPE: DNA
<213> ORGANISM: Artificial
<220> FEATURE:
<223> OTHER INFORMATION: Codon optimised mouse hactor H variant

<400> SEQUENCE: 12

```
ggcgcgccgg atccaaaaat gagattgtcc gctagaatca tctggttgat cttgtggact     60
gtttgtgctg ctgaggattg taaaggtcca ccaccgcggg aaaactccga gattttgtct    120
ggttcttggt ccgaacaatt gtacccagag ggtactcaag ctacttacaa gtgtagacca    180
ggttacagaa ctttgggtac tatcgttaag gtttgtaaga acggaaagtg ggttgcttct    240
caaccatcca gaatctgtag aaagaaacca tgtggtcacc caggtgatac tccattcggt    300
tccttcagat tggctgttgg ttcccaattc gagttcggtg ctaaggttgt ttacacttgt    360
gacgacggtt accaattgtt gggtgagatc gactacagag aatgtggtgc tgacggttgg    420
attaacgaca tcccattgtg tgaggttgtt aagtgtttgc cagttactga gttggagaac    480
ggtagaattg tttctggtgc tgctgaaact gaccaagagt actacttcgg acaggttgtt    540
agattcgagt gtaactccgg tttcaagatc gaaggtcaca aagagattca ctgttccgag    600
aacggtttgt ggtctaacga gaagccaaga tgtgttgaga ttttgtgtac tccaccaaga    660
gttgaaaacg gtgacggtat caacgttaag ccagtttaca aagagaacga gagataccac    720
tacaagtgta agcacggtta cgttccaaaa gaaagaggtg acgctgtttg tactggttct    780
ggttggtcct ctcaaccatt ctgtgaagag aagagatgtt ccccaccata catcttgaac    840
ggtatctaca ctccacacag aatcattcac agatccgacg acgagattag atacgaatgt    900
aactacggat tctacccagt tactggttcc actgtttcca agtgtactcc aactggttgg    960
attccagttc caagatgtac tttgaagcca tgtgagttcc cacaattcaa gtacggtaga   1020
ttgtactacg aagagtcctt gagaccaaac ttcccagttt ccatcggtaa caagtactcc   1080
tacaagtgtg acaacggttt ctctccacca tctggttact cttgggacta cttgagatgt   1140
actgctcaag gttgggaacc agaggttcca tgtgttagaa agtgtgtttt ccactacgtt   1200
gagaacggtg attctgctta ctgggagaag gtttacgttc aaggtcagtc cttgaaggtt   1260
cagtgttaca acggttactc cttgcaaaac ggtcaggaca ctatgacttg tactgagaac   1320
ggttggtcac caccaccaaa gtgtatcaga atcaagactt gttccgcttc cgacattcac   1380
atcgacaacg gattcttgtc tgagtcctcc tccatttacg ctttgaacag agagacttcc   1440
tacagatgta agcagggata cgttacaaac actggtgaga tttccggttc catcacttgt   1500
ttgcagaatg gttggtcccc acagccatct tgtattaagt cctgtgacat gccagttttc   1560
gagaactcca tcactaagaa cactagaaca tggttcaagt tgaacgacaa gttggactac   1620
gagtgtttgg ttggtttcga gaacgagtac aagcacacta agggttccat cacatgtact   1680
tactacggtt ggtctgacac tccatcctgt tacgaaagag agtgttccgt tccaactttg   1740
gacagaaagt tggttgtttc cccaagaaaa gagaagtaca gagttggaga cttgttggag   1800
ttctcttgtc actctggtca tagagttggt ccagactccg ttcaatgtta ccactttgga   1860
tggtccccag gttttccaac ttgtaagggt caggttgctt cttgtgctcc accattggag   1920
attttgaacg gtgagatcaa cggtgctaag aaggttgaat actcccacgg tgaagttgtt   1980
aagtacgact gtaagccaag attcttgttg aagggtccaa acaagatcca atgtgttgac   2040
ggtcaatgga ctactttgcc agtttgtatc gaggaagaaa gaacttgcgg agacatccca   2100
gaattggaac acggttccgc taagtgttct gttccaccat accaccatgg tgattccgtt   2160
gagttcatct gtgaggagta gttcactatg atcggtcacg gttccgtttc ttgtatttcc   2220
ggtaagtgga ctcagttgcc aaagtgtgtt gctactgacc agttggagaa gtgtagagtt   2280
ttgaagtcca ctggtatcga ggctatcaag ccaaagttga ctgagttcac tcaccagtcc   2340
actatggact acaaatgtag agacaagcaa gagtacgaga gatccatctg tatcaacggt   2400
```

aaatgggacc cagaaccaca atgtacttcc aagacttctt gtccaccacc accacaaatt 2460
ccaaacactc aggttatcga gactactgtt aagtacttgg acggtgagaa gttgtccgtt 2520
ttgtgtcagg acaactactt gactcaagac tccgaagaga tggtttgtaa ggacggtaga 2580
tggcaatctt tgccaagatg tatcgagaag atcccatgtt ctcagccacc aactattgag 2640
cacggttcca ttaacttgcc aagatcctcc gaagaaagaa gagactccat cgaatcctct 2700
tctcacgaac acggtactac tttctcttac gtttgtgatg acggtttcag aatcccagaa 2760
gagaacagaa tcacttgtta catgggaaag tggtccactc cacctagatg tgttggtttg 2820
ccatgtggtc caccaccttc tattccattg ggtactgttt ctttggagtt ggagtcctac 2880
caacacggtg aagaggttac ttaccactgt tccactggtt tcggtattga tggtccagct 2940
ttcattatct gtgagggtgg taagtggtct gatccaccta agtgtattaa gactgactgt 3000
gacgttttgc caactgttaa gaacgctatc atcagaggta agtccaagaa gtcctacaga 3060
actggagagc aggttacttt cagatgtcag tccccatacc aaatgtaggg ttccgacact 3120
gttacttgtg ttaactccag atggatcggt caaccagttt gtaaggataa ctcctgtgtt 3180
gatccaccac atgttccaca agctactatc gttactagaa ctaagaacaa gtacttgcat 3240
ggtgacagag ttagatatga gtgtaacaag ccattggagt tgttcggtca agttgaggtt 3300
atgtgtgaga acggtatctg gactgagaag ccaaagtgta gagactccac tggtaagtgt 3360
ggtcctccac caccaattga caacggtgac atcacttctt tgtccttgcc agtttacgaa 3420
cctttgtcct ccgttgagta ccaatgtcag aagtactact tgttgaaagg taagaaaact 3480
atcacttgta ctaatggtaa atggtccgag ccaccaactt gtttgcacgc ttgtgttatc 3540
ccagagaaca tcatggaatc ccacaacatc atcttgaagt ggagacacac tgagaagatt 3600
tactctcact ccggtgagga cattgagttc ggttgtaagt acggttacta caaggctaga 3660
gactctccac cattcagaac taagtgtatc caaggaacta tcaactaccc aacttgtgtt 3720
taatgagcgg ccgcttaatt aa 3742

<210> SEQ ID NO 13
<211> LENGTH: 3733
<212> TYPE: DNA
<213> ORGANISM: Artificial
<220> FEATURE:
<223> OTHER INFORMATION: Codon optimised human hactor H variant

<400> SEQUENCE: 13
ggcgcgccgg atccaaaaat gagattgttg gctaagatca tctgtttgat gttgtgggct 60
atctgtgttg ctgaggactg taacgaattg ccaccgcgga gaaacactga gattttgact 120
ggttcctggt ccgatcaaac ttacccagag ggtactcagg ctatctacaa gtgtagacca 180
ggttacagat ccttgggtaa catcatcatg gtttgtagaa agggtgagtg ggttgctttg 240
aacccattga gaaagtgtca gaaaagacca tgtggtcacc caggtgatac tccattcggt 300
actttcactt tgactggtgg taacgttttc gagtacggtg ttaaggctgt ttacacttgt 360
aacgagggtt accagttgtt gggtgagatc aactacagag agtgtgatac tgacggttgg 420
actaacgaca ttccaatctg tgaggttgtt aagtgtttgc cagttactgc tccagagaac 480
ggtaagattg tttcctccgc tatggaacca gatagagagt accacttcgg tcaggctgtt 540
agattcgttt gtaactccgg ttacaagatt gaaggtgacg aagagatgca ctgttctgat 600
gacggtttct ggtccaaaga aaagccaaag tgtgttgaga tttcctgtaa gtccccagac 660

-continued

```
gttattaacg gttccccaat ctcccaaaag atcatctaca aagagaacga gagattccag    720
tacaagtgta acatgggtta cgagtactct gaaagaggtg acgctgtttg tactgaatct    780
ggttggagac cattgccatc ctgtgaagag aagtcctgtg acaacccata cattccaaac    840
ggtgactact ccccattgag aatcaagcac agaactggtg acgagatcac ttaccagtgt    900
agaaacggtt tctacccagc tactagaggt aacactgcta agtgtacttc cactggttgg    960
attccagctc caagatgtac tttgaagcca tgtgactacc cagatatcaa gcacggtggt   1020
ttgtaccacg agaacatgag aagaccatac ttcccagttg ctgttggaaa gtactactcc   1080
tactactgtg acgaacactt cgaaactcca tctggttctt actgggacca catccactgt   1140
actcaagatg gttggtcccc agctgttcca tgtttgagaa aatgttactt cccatacttg   1200
gagaacggtt acaaccagaa ctacggtaga aagttcgttc agggaaagtc cattgacgtt   1260
gcttgtcatc caggttacgc tttgccaaag gctcagacta ctgttacttg tatggaaaac   1320
ggttggtccc ctactcctag atgtatcaga gttaagactt gttccaagtc ctccatcgac   1380
attgagaacg gtttcatttc cgagtcccag tacacttacg ctttgaaaga gaaggctaag   1440
taccagtgta aattgggata cgttactgct gacggtgaaa cttccggttc catcacttgt   1500
ggtaaggatg gttggtctgc tcaaccaact tgtatcaagt cttgtgacat cccagttttc   1560
atgaacgcta gaactaagaa cgacttcaca tggttcaagt tgaacgacac tttggactac   1620
gaatgtcacg acggttacga atctaacact ggttccacta ctggttccat cgtttgtggt   1680
tacaacggtt ggtctgactt gccaatctgt tacgagagag agtgcgagtt gccaaagatc   1740
gacgttcatt tggttccaga cagaaagaag gaccagtaca aggttggtga ggttttgaag   1800
ttctcctgta agccaggttt cactatcgtt ggtccaaact ccgttcagtg ttaccatttc   1860
ggtttgtccc cagacttgcc tatttgtaaa gagcaggttc agtcttgcgg tccaccacca   1920
gaattgttga acggtaacgt taaagaaaag actaaagaag agtacggtca ctctgaggtt   1980
gttgagtact actgtaaccc aagattcttg atgaagggtc caaacaagat ccaatgtgtt   2040
gacggtgagt ggactacttt gccagtttgt atcgttgaag agtccacttg tggtgacatt   2100
ccagaattgg aacacggttg ggctcaattg tcatccccac catactacta cggtgactcc   2160
gttgagttca actgttccga gtccttcact atgattggtc acagatccat cacatgtatc   2220
cacggtgttt ggactcaatt gccacagtgt gttgctatcg acaagttgca acaatgtcaa   2280
tcctccaact tgatcatctt ggaggaacac ttgaagaaca agcaagagtt cgaccacaac   2340
tccaacatcc aataccaatg tcaaggtcaa gagggttgga ttcacactgt ttgtatcaac   2400
ggtcaatggg accctgaagt taactgttcc atggctcaga ttcagttgtg tccaccacct   2460
ccacaaattc caaactccca caacatgact actactttga actacagaga tggtgagaag   2520
gtttccgttt tgtgtcaaga gaactacttg atccaagagg gtgaggaaat cacttgtaag   2580
gacggtagat ggcaatccat cccattgtgt gttgagaaga tcccatgttc ccaaccacca   2640
caaattgagc acggtactat caactcttcc agatcctctc aagagtctta cgctcacggt   2700
actaagttgt cctacacttg tgagggtggt ttcagaatct ctgaggaaaa cgagactact   2760
tgttacatgg gaaagtggtc ctctccacca caatgtgaag gtttgccttg taagtctcca   2820
ccagagattt ctcacggtgt tgttgctcac atgtccgact cttaccaata cggtgaagag   2880
gttacttaca agtgtttcga gggtttcggt attgatggtc cagctatcgc taagtgtttg   2940
ggtgaaaagt ggtcccatcc tccatcctgt atcaagactg actgtttgtc cttgccatct   3000
ttcgagaacg ctatcccaat gggtgaaaag aaggacgttt acaaggctgg tgaacaggtt   3060
```

-continued

```
acatacactt gtgctactta ctacaagatg gacggtgctt ccaacgttac ttgtatcaac   3120

tccagatgga ctggtagacc aacttgtaga gacacttcct gtgttaaccc accaactgtt   3180

cagaacgctt acatcgtttc cagacagatg tctaagtacc catccggtga gagagttaga   3240

taccaatgta gatccccata cgagatgttc ggtgacgaag aggttatgtg tttgaacggt   3300

aattggactg aaccaccaca gtgtaaggac tccactggta agtgtggtcc acctccacca   3360

attgacaacg gtgacatcac ttctttccca ttgtccgttt acgctccagc ttcttccgtt   3420

gagtaccagt gtcagaactt gtaccagttg gagggtaaca agagaatcac ttgtagaaac   3480

ggacaatggt ctgagccacc aaagtgtttg cacccatgtg ttatctccag agaaatcatg   3540

gaaaactaca acattgcttt gagatggact gctaagcaga agttgtactc cagaacaggt   3600

gagtctgttg agtttgtttg taagagaggt tacagattgt cctccagatc ccacactttg   3660

agaactacat gttgggacgg aaagttggag tacccaactt gtgctaagag ataatgagcg   3720

gccgcttaat taa                                                      3733
```